United States Patent
Nicholas et al.

(10) Patent No.: US 11,884,932 B2
(45) Date of Patent: *Jan. 30, 2024

(54) IN VITRO PRODUCTION OF MEDIAL GANGLIONIC EMINENCE PRECURSOR CELLS

(71) Applicant: The Regents of the University of California, Oakland, CA (US)

(72) Inventors: Cory R. Nicholas, San Francisco, CA (US); John L. Rubenstein, San Francisco, CA (US); Arnold R. Kriegstein, Mill Valley, CA (US); Arturo Alvarez-Buylla, Woodside, CA (US)

(73) Assignee: The Regents of the University of California, Oakland, CA (US)

( * ) Notice: Subject to any disclaimer, the term of this patent is extended or adjusted under 35 U.S.C. 154(b) by 701 days.

This patent is subject to a terminal disclaimer.

(21) Appl. No.: 16/938,079

(22) Filed: Jul. 24, 2020

(65) Prior Publication Data

US 2021/0040443 A1 Feb. 11, 2021

Related U.S. Application Data

(63) Continuation of application No. 16/126,594, filed on Sep. 10, 2018, now Pat. No. 10,760,048, which is a continuation of application No. 14/763,397, filed as application No. PCT/US2014/029734 on Mar. 14, 2014, now Pat. No. 10,100,279.

(60) Provisional application No. 61/783,594, filed on Mar. 14, 2013.

(51) Int. Cl.
*C12N 5/079* (2010.01)
*C12N 5/0793* (2010.01)
*C12N 15/63* (2006.01)

(52) U.S. Cl.
CPC ......... *C12N 5/0618* (2013.01); *C12N 5/0619* (2013.01); *C12N 15/63* (2013.01); *C12N 2500/90* (2013.01); *C12N 2501/13* (2013.01); *C12N 2501/41* (2013.01); *C12N 2501/727* (2013.01); *C12N 2501/999* (2013.01); *C12N 2506/02* (2013.01); *C12N 2506/45* (2013.01)

(58) Field of Classification Search
CPC .... C12N 5/0618; C12N 5/0619; C12N 15/63; C12N 2500/90; C12N 2501/13; C12N 2501/41; C12N 2501/727; C12N 2501/999; C12N 2506/02; C12N 2506/45
USPC ................ 435/368, 377, 384, 455
See application file for complete search history.

(56) References Cited

U.S. PATENT DOCUMENTS

| | | | |
|---|---|---|---|
| 7,011,828 B2 | 3/2006 | Reubinoff et al. | |
| 7,186,557 B2 | 3/2007 | Marko | |
| 7,632,681 B2 | 12/2009 | Kopyov | |
| 7,820,439 B2 | 10/2010 | Alam et al. | |
| 8,178,349 B2 | 5/2012 | Terskikh et al. | |
| 8,252,586 B2 | 8/2012 | Carpenter et al. | |
| 9,952,216 B2 | 4/2018 | Visel | |
| 10,100,279 B2* | 10/2018 | Nicholas | C12N 5/0618 |
| 10,760,048 B2* | 9/2020 | Nicholas | C12N 5/0618 |
| 2002/0009743 A1 | 1/2002 | Carpenter | |
| 2002/0019046 A1 | 2/2002 | Carpenter et al. | |
| 2004/0224887 A1 | 11/2004 | Jessel et al. | |
| 2005/0095702 A1 | 5/2005 | Alam et al. | |
| 2005/0244964 A1 | 11/2005 | Davidson | |
| 2006/0073587 A1 | 4/2006 | Stice et al. | |
| 2006/0148083 A1 | 7/2006 | Yu et al. | |
| 2006/0183221 A1 | 8/2006 | Schulz | |
| 2008/0044901 A1 | 2/2008 | Sasai et al. | |
| 2009/0257987 A1 | 10/2009 | Offen et al. | |
| 2010/0166720 A1 | 7/2010 | Vanderhaeghen et al. | |
| 2010/0255580 A1 | 10/2010 | Rezania | |
| 2010/0267073 A1 | 10/2010 | Przedborski et al. | |
| 2012/0040393 A1 | 2/2012 | Zhang et al. | |
| 2012/0094381 A1 | 4/2012 | Chambers et al. | |
| 2012/0148549 A1* | 6/2012 | Anderson | A61P 25/00 435/325 |
| 2012/0190108 A1 | 7/2012 | Poole | |
| 2012/0237484 A1 | 9/2012 | Bissonnette et al. | |

FOREIGN PATENT DOCUMENTS

| | | |
|---|---|---|
| CN | 102559593 | 7/2012 |
| EP | 2028268 | 2/2009 |
| JP | 2010-536357 | 12/2010 |
| JP | 2012524525 | 10/2012 |
| KR | 101182758 | 9/2012 |
| WO | WO 2008068589 | 6/2008 |
| WO | WO 2009147400 | 12/2009 |
| WO | WO 2010141622 | 12/2010 |
| WO | WO 2012013936 | 2/2012 |

OTHER PUBLICATIONS

Watanabe et al. (2007) Nat. Biotech., vol. 25(6), 681-686.*
Bragdon et al. (2011) "Bone Morphogenetic Proteins: A critical review" Cellular Signalling, 23:609-620.
Aubry et al. "Striatal progenitors derived from human ES cells mature into DARPP32 neurons in vitro and in quinolinic acid-lesioned rats," PNAS (2008) 105(43):16707-16712.
Besser "Expression of Nodal, Lefty-A, and Lefty-B in Undifferentiated Human Embryonic Stem Cells Requires Activation of Smad2/3*" J Biol Chem (2004) 279: 45076-84.

(Continued)

*Primary Examiner* — Anne Marie S Wehbe
(74) *Attorney, Agent, or Firm* — Shweta Chandra; Bozicevic, Field & Francis LLP

(57) ABSTRACT

Methods and systems for generating MGE precursor cells in vitro as well as compositions of enriched MGE precursor cells are provided. The methods and systems provide efficient production of MGE precursors. The methods and systems disclosed herein provide functional MGE precursors which differentiate into functional GABAergic interneurons.

27 Claims, 39 Drawing Sheets

Specification includes a Sequence Listing.

(56) References Cited

OTHER PUBLICATIONS

Bissonnette et al. "The Controlled Generation of Functional Basal Forebrain Cholinergic Neurons from Human Embryonic Stem Cells," Stem Cells (2011) 29:802-811.
Borghese et al. (2010) "Inhibition of Notch Signaling in Human Embryonic Stem Cell-Derived Neural Stem Cells Delays G1/S Phase Transition and Accelerates Neuronal Differentiation In Vitro and In Vivo" Stem Cells, 28:955-964.
Brewer "Optimized Survival of Hippocampal Neurons in B27-Supplemented Neurobasalm, a New Serum-free Medium Combination" J Neurosci Res (1993); 35:567-76.
Brewer et al. "Neurobasa™ Medium/B27 Supplement: A New Serum-Free Medium Combination for Survival of Neurons," Focus (1994) 16(1):6-9.
Chemically defined Medium, Wikipedia, Downloaded Apr. 2016.
Chen et al."NS21: Re-defined and Modified Supplement 827 for Neuronal Cultures", J Neurosci Methods. Jun. 30, 2008; 171(2): 239-247.
Chambers et al. "Highly efficient neural conversion of human ES and iPS cells by dual inhibition of SMAD signaling," Nat Biotechnol (2009) 27(3):275-280.
Esfandiari et al. "Glycogen Synthase Kinase-3 Inhibition Promotes Proliferation and Neuronal Differentiation of Human-Induced Pluripotent Stem Cell-Derived Neural Progenitors" Stem Cell Develop 2012;21 :3233-43.
Germain et al. "Derivation and isolation of NKX2.1-positive basal forebrain progenitors from human embryonic stem cells", Stem Cells Dev. 2013, 22(10):1477-1489.
Goulburn et al. "A Targeted NKX2.1 Hesc Reporter Line Enables Identification of Human Basal Forebrain Derivatives," Stem Cells (2011) 29(3):462-473.
Goulburn et al. "Generating GABAergic cerebral cortical interneurons from mouse and human embryonic stem cells," Stem Cell Research (2012) 8:416-426.
Gu et al. "The effect of B27 supplement on promoting in vitro propagation of Her2/neu-transformed mammary tumorspheres," Journal of Biotech Research (2011) 3:7-18.
Kim et al. "Investigating synapse formation and function using human pluripotent stem cell-derived neurons," PNAS (2011) 108(7):3005-3010.

Li et al. "Coordination of sonic hedgehog and Wnt signaling determines ventral and dorsal telencephalic neuron types from human embryonic stem cells," Development (2009) 136(23):4055-4063.
Liu et al. "Medial ganglionic eminence-like cells derived from human embryonic stem cells correct learning and memory deficits," Nature Biotechnology (2013) 31(5):440-447.
Liu et al. "Directed differentiation of forebrain GABA interneurons from human pluripotent stem cells," Nature Protocols (2013) 8(9):1670-1679.
Maroof et al. "Prosective Isolation of Cortical Interneuron Precursors from Mouse Embryonic Stem Cells," Journal of Neuroscience (2010) 30(13):4667-4675.
Maroof et al. "Directed Differentiation and Functional Maturation of Cortical Interneurons from Human Embryonic Stem Cells," Cell Stem Cell (2013) 12(5):559-572.
N2 supplement, Thermo Fisher Sci, 2016.
Nat et al. Stem Cell Dev 2012;21 :1016-46, Epub Feb. 8, 2012.
Perrier et al. "Derivation of midbrain dopamine neurons from human embryonic stem cells" PNAS 2004;1 01 :12543-8.
Potter et al. (2009) "Generation of Cre-transgenic mice using D1x1/D1x2 enhancers and their characterization in GABAergic interneurons" Mol. Cell. Neurosci., 40(2):167-186.
Qian et al. "Timing of CNS Cell Generation: A Programmed Sequence of Neuron and Glial Cell Production from Isolated Murine Cortical Stem Cells," Neuron (2000) 28:69-80.
Shi et al. "Human cerebral cortex development from pluripotent stem cells to functional excitatory synapses," Nature Neuroscience (2012) 15(3):477-486.
Sugahara et al. "Involvement of Hedgehog and FGF signaling in the lamprey telencephalon: evolution of regionalization and dorsoventral patterning of the vertebrate forebrain" Development 2011; 138, 1217-1226.
Watanabe et al. "A ROCK inhibitor permits survival of dissociated human embryonic stem cells," Nature Biotechnology (2007) 25(6):681-686.
Wu et al. "Integrative genomic and functional analyses reveal neuronal subtype differentiation bias in human embryonic stem cell lines," PNAS (2007) 104(34):13821-13826.
Zhang et al. "In Vitro differentiation of transplantable neural precursors from human embryonic stem cells," Nature Biotechnology (2001) 13:1129-1133.

* cited by examiner

H

I

J

FIG. 15
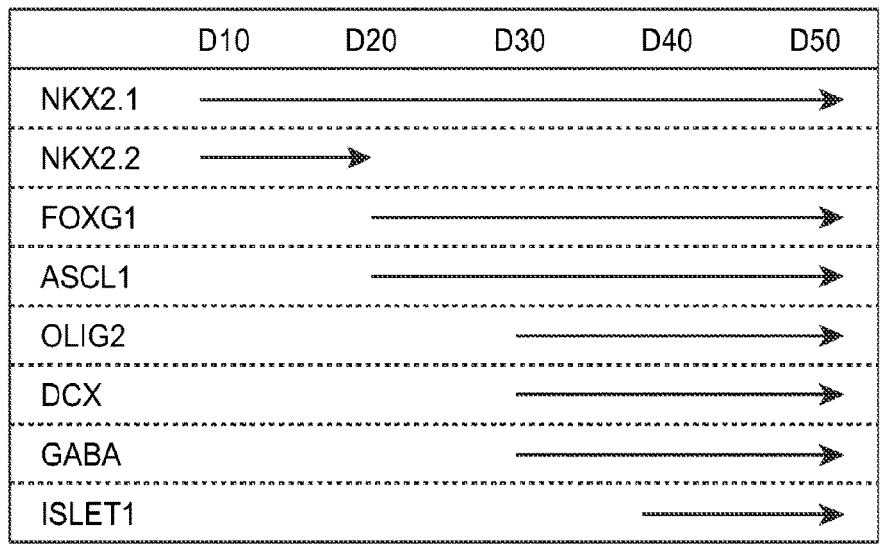
FIG. 16
| Protocol [a] | Mice Injected [b] | Mice with Tumor [c] | % Incidence |
|---|---|---|---|
| Untreated | 12 | 12 | 100 |
| Low Density | 12 | 6 | 50 |
| DAPT | 9 | 3 | 33 |
| PSANCAM - | 4 | 3 | 75 |
| PSANCAM + | 6 | 0 | 0 |
a) All treatments include FACS sort for NKX2.1-GFP+ cells
b) Mice contained surviving human cells
c) HNA + KI67+ injection cores persisted ≥ 4 months after injection
FIG. 17
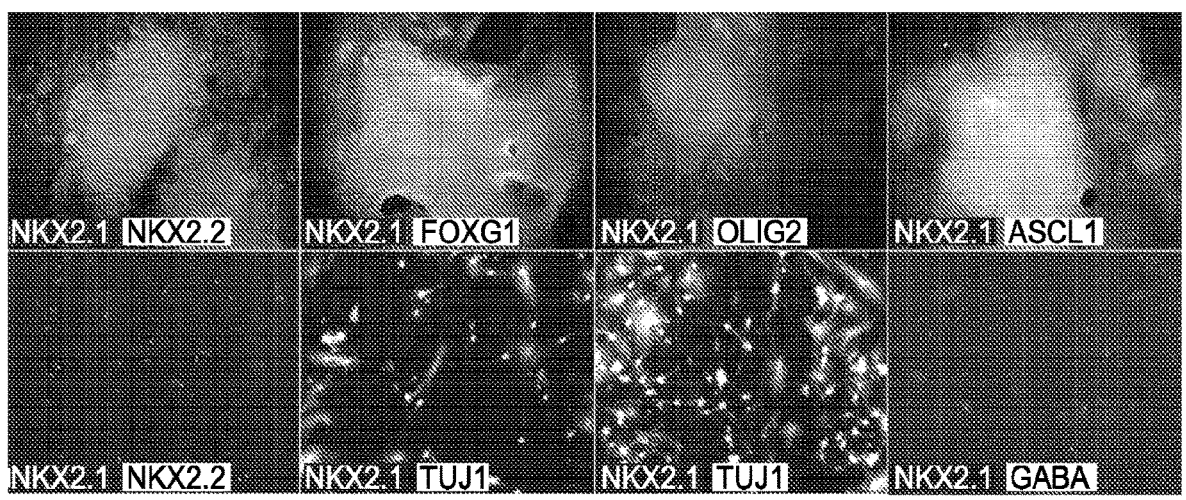

SEQUENCE LISTING

<160> NUMBER OF SEQ ID NOS: 28

<210> SEQ ID NO 1
<211> LENGTH: 20
<212> TYPE: DNA

```
<213> ORGANISM: Artificial sequence
<220> FEATURE:
<223> OTHER INFORMATION: Synthetic Oligonucleotide

<400> SEQUENCE: 1
gtcctgtcgc ccaccatctc                                                    20

<210> SEQ ID NO 2
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 2
ccctcccaac gccactgac                                                     19

<210> SEQ ID NO 3
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 3
tcagagatgt cccgactcct g                                                  21

<210> SEQ ID NO 4
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 4
gccgcttcta tccttgtcgt aa                                                 22

<210> SEQ ID NO 5
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 5
gcctcaacaa cgtcccttac t                                                  21

<210> SEQ ID NO 6
<211> LENGTH: 23
<212> TYPE: DNA
<213> ORGANISM: Artificial sequence
<220> FEATURE:
<223> OTHER INFORMATION: Synthetic Oligonucleotide

<400> SEQUENCE: 6
tcactatccg aatttcaggc tca                                                23

<210> SEQ ID NO 7
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 7
agaagaacgg caagtacgag a                                                  21
```

```
<210> SEQ ID NO 8
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 8
tgttgaggga cagattgtgg c                                              21

<210> SEQ ID NO 9
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 9
cgaggactct ggacagtaga gg                                             22

<210> SEQ ID NO 10
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 10
gatcttgagc cccagttttc tg                                             22

<210> SEQ ID NO 11
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 11
ggtggtctcc tctgacttca ac                                             22

<210> SEQ ID NO 12
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 12
ttcgttgtca taccaggaaa tg                                             22

<210> SEQ ID NO 13
<211> LENGTH: 23
<212> TYPE: DNA
<213> ORGANISM: Artificial sequence
<220> FEATURE:
<223> OTHER INFORMATION: Synthetic Oligonucleotide

<400> SEQUENCE: 13
tctgcaagat ggactacttc agc                                            23

<210> SEQ ID NO 14
<211> LENGTH: 21
<212> TYPE: DNA
<213> ORGANISM: Artificial sequence
<220> FEATURE:
```

<223> OTHER INFORMATION: Synthetic Oligonucleotide

<400> SEQUENCE: 14
cttgggttga ctgtcctgtt c                                              21

<210> SEQ ID NO 15
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 15
agactcgctc gctcatttgt                                                20

<210> SEQ ID NO 16
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 16
ctccatgccc actttcttgt                                                20

<210> SEQ ID NO 17
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 17
cgctgcgaca ctacatcaac                                                20

<210> SEQ ID NO 18
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 18
cagggtcttc aagccgagtt                                                20

<210> SEQ ID NO 19
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 19
agctcctcaa atcgcatcc                                                 19

<210> SEQ ID NO 20
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 20
atagtcgtcg cagctttcg                                                 19

```
<210> SEQ ID NO 21
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 21
gcaaaacccg gaggaggagt c                                              21

<210> SEQ ID NO 22
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 22
ccacatcggc ctgtgtatat c                                              21

<210> SEQ ID NO 23
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 23
aaagagtgcg gatgatgtga ag                                             22

<210> SEQ ID NO 24
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 24
accccaattt tgccgtccc                                                 19

<210> SEQ ID NO 25
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 25
gctgctgtct gaacccaac                                                 19

<210> SEQ ID NO 26
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 26
cgttctcggg gtgccatag                                                 19

<210> SEQ ID NO 27
<211> LENGTH: 18
<212> TYPE: DNA
<213> ORGANISM: Artificial sequence
<220> FEATURE:
<223> OTHER INFORMATION: Synthetic Oligonucleotide
```

```
<400> SEQUENCE: 27
gcaactacgt gggcgact                                                    18

<210> SEQ ID NO 28
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 28
cgaggcacgt acttgtgaga                                                  20
```

IN VITRO PRODUCTION OF MEDIAL GANGLIONIC EMINENCE PRECURSOR CELLS

CROSS REFERENCE

This application claims the benefit of U.S. Provisional Patent Application No. 61/783,594 filed Mar. 14, 2013, which application is incorporated herein by reference in their entirety.

STATEMENT REGARDING FEDERALLY SPONSORED RESEARCH

This invention was made with government support under Grant No. MH081880 awarded by the US National Institutes of Health. The government has certain rights in the invention. This invention was made with support under Grant Nos. RC1-00346 and RB2-01602 awarded by California Institute for Regenerative Medicine.

INTRODUCTION

Inhibitory interneurons account for about 20% of neurons in the cerebral cortex. Deficiencies of interneurons are implicated in several neurological disorders. Most cortical interneurons originate in the medial ganglionic eminence (MGE) of the developing ventral telencephalon region of the brain.

Mouse MGE transplants were shown to ameliorate multiple rodent models of neurological disorders, suggesting human MGE cells may represent a unique therapeutic candidate.

However, in vitro methods for efficient generation of cells having characteristics of cells of the MGE are not available.

As such, there is a need for method for efficiently generating MGE precursor cells in vitro and for cell populations enriched in MGE precursor cells.

SUMMARY

Methods and systems for generating MGE precursor cells in vitro as well as compositions of enriched MGE precursor cells are provided. The methods and systems provide efficient production of functional MGE precursors, which differentiate into functional GABAergic interneurons.

A method of producing medial ganglionic eminence (MGE) precursor cells from primate pluripotent stem (pPS) cells is provided.

In certain embodiments, the method includes culturing the pPS cells in a serum free medium containing an activator of sonic hedgehog pathway and a neural inducing supplement to generate the MGE precursor cells. The pPS cell may be cultured in an adherent culture or in a suspension culture.

In certain embodiments, the method includes culturing the pPS cells in a serum free medium containing an activator of sonic hedgehog pathway and a neural inducing supplement to generate embryoid bodies (EBs), wherein the EBs comprise the MGE precursor cells.

In certain cases, the neural inducing supplement may be B27. In certain cases, the neural inducing supplement may be NS21.

In certain embodiments, the pPS cells may be human pluripotent stem (hPS) cells. The hPS cells may be human embryonic stem (hES) cells or induced pluripotent stem (iPS) cells.

In certain embodiments, the pPS cells may be induced to differentiate prior to culturing the pPS cells in the serum free medium comprising the activator of sonic hedgehog pathway and the neural inducing supplement. For example, the pPS cells may be induced to differentiate by overgrowth of the pPS cell culture, or by culturing pPS cells in suspension in culture vessels having a substrate with low adhesion, culturing pPS in absence of feeder layer, or adding a differentiation factor such as FGF before culturing the pPS cells in the serum free medium comprising the activator of sonic hedgehog pathway and the neural inducing supplement.

In certain embodiments, the method may include isolating the EBs; plating the isolated EBs on an adherent substrate to provide adherent EBs; and culturing the adherent EBs.

In certain embodiments, the method may include isolating the EBs; dissociating the EBs mechanically or enzymatically to produce single cells or clusters of cells; plating the dissociated cells on an adherent substrate to provide an adherent monolayer; and culturing the adherent monolayer.

In certain embodiments, the method may include isolating the EBs; dissociating the EBs mechanically or enzymatically to produce single cells or clusters of cells; plating the dissociated cells on a cellular feeder layer to provide an adherent co-culture; and culturing the adherent co-culture.

In certain embodiments, the method may include isolating the EBs, adherent EBs, monolayer, or co-cultures; dissociating the EBs, adherent EBs, monolayer, or co-cultures mechanically or enzymatically to produce single cells; incubating the single cells with an antibody to a cell surface marker for MGE precursor cells; and isolating the precursor cells.

In certain embodiments, the method may include isolating the EBs, adherent EBs, monolayer, co-cultures, dissociated cultures, or isolated precursor cells; and adding a cryoprotectant, such as, antifreeze compounds, e.g., glycols (glycerol, ethylene glycol, propylene glycol), dimethyl sulfoxide (DMSO), or sucrose.

In certain cases, a method of producing medial ganglionic eminence (MGE) precursor cells from primate pluripotent stem (pPS) cells may include culturing the pPS cells in a serum free medium to generate embryoid bodies (EBs), wherein the EBs include the MGE precursor cells, wherein the serum free medium includes an activator of sonic hedgehog pathway, an inhibitor of Rho-associated kinase (ROCK), an inhibitor of SMAD, an inhibitor of Wnt and B27.

The pPS cells are human pluripotent stem (hPS) cells may be human embryonic stem (hES) cells or induced pluripotent stem (iPS) cells.

In certain cases, the method may further include isolating the EBs; plating the isolated EBs on an adherent substrate to provide adherent EBs; and culturing the adherent EBs.

In certain embodiments, the adherent EBs are cultured in a serum free medium comprising an activator of sonic hedgehog pathway, an inhibitor of SMAD, an inhibitor of Wnt, and B27.

In certain embodiments, the adherent EBs are cultured in a serum free medium that does not contain an inhibitor of ROCK.

A method for producing inhibitory interneurons is provided, the method may include isolating the EBs, adherent EBs, monolayer, co-cultures, dissociated cultures, or sorted cells produced as described above; producing a cell suspension of the isolated cells and transplanting cell suspensions into the primate nervous system.

BRIEF DESCRIPTION OF THE DRAWINGS

FIG. 15 provides a summary of marker expression during differentiation from hESCs.

FIG. 16 provides a summary of hESC differentiation protocol optimization, animal transplantation, and tumor incidence.

FIG. 17 depicts MGE precursor cells differentiated in vitro from hESC line ESI17.

DEFINITIONS

Figure 1:
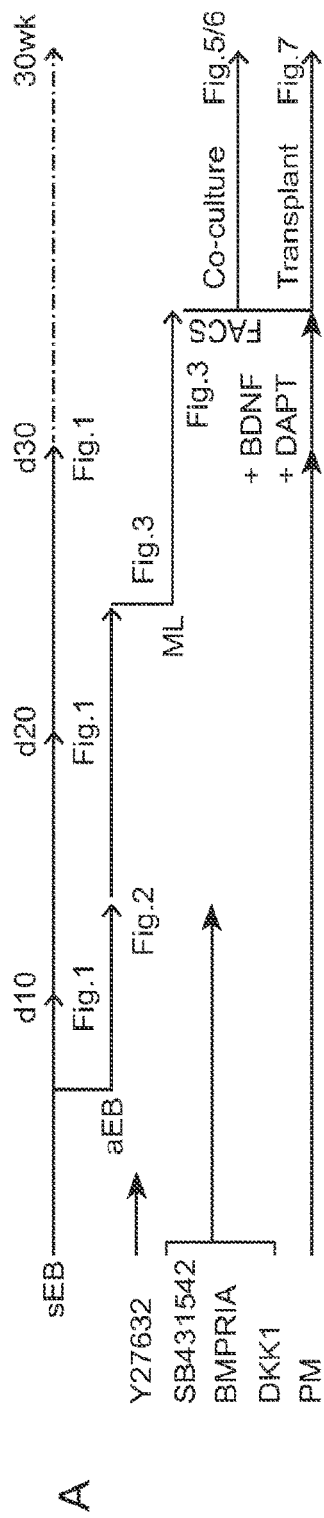
FIG. 1 (panels A-B) illustrate the generation of MGE-like Precursor Cells.
Figure 1:
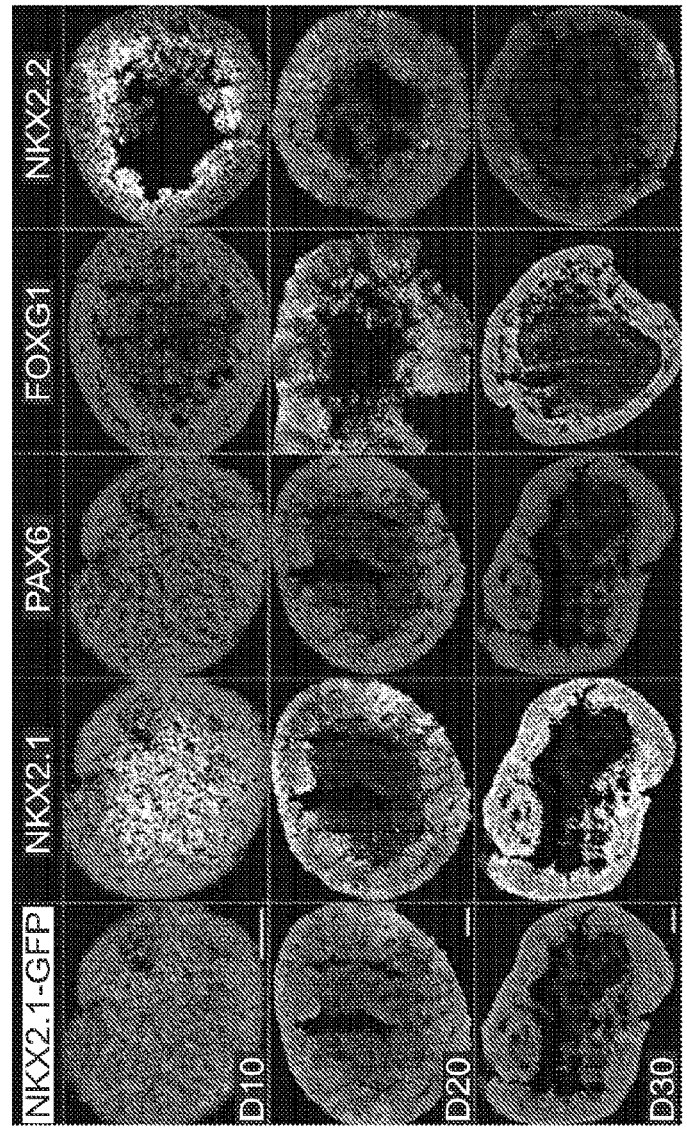

As used herein, "embryoid body", "embryoid bodies", "EBs" or "EB cells" typically refers to a morphological, three-dimensional, or organoid-type structure comprised of a population of undifferentiated and differentiated cells which are derived from pluripotent stem cells (e.g., primate pluripotent stem cells (pPS), embryonic stem (ES) cells, induced pluripotent stem (iPS) cells) that have undergone differentiation, Under culture conditions suitable for EB formation, ES cells proliferate and form small mass of cells that begin to differentiate. In the first phase of differentiation, usually corresponding, to about days 1-4 of differentiation for human cells, the small mass of cells forms a layer of endodermal cells on the outer layer, and is considered a "simple embryoid body." In the second phase, usually corresponding to about days 3-20 post-differentiation for human cells, "complex embryoid bodies" are formed, which are characterized by extensive differentiation of ectodermal and mesodermal cells and derivative tissues. As used herein, the term "embryoid bodies" or "EB" encompasses both simple and complex embryoid bodies unless otherwise required by context. The determination of when embryoid bodies have formed in a culture of ES/iPS cells is routinely made by persons of skill in the art by, for example, visual inspection of the morphology, detection of cell markers. Floating masses of about 20 cells or more (e.g., ES/iPS cells) are considered to be suspension embryoid bodies (sEB). (see. e.g., Schmitt, R., et al. (1991) Genes Dev. 5:728-740; Doetschman, T. C., et al. (1985) J. Embryol. Exp. Morph. 87:27-45). Suspension EBs can be plated onto an adherent substrate to generate adherent EBs (aEB).

As used herein, "medial ganglionic eminence (MGE) precursor cell(s)" or "MGE neural precursor cells," refer to a population of mitotic and post-mitotic cells that express the markers expressed by cells in the MGE region of the developing brain. In general MGE precursor cells express markers such as, homeobox gene Nkx2.1, LIM-homeobox genes Lhx6, Lhx7, or Lhx8. MGE precursor cells are capable of differentiating into interneurons under suitable differentiation conditions.

By "pluripotent stem cell" or "pluripotent cell" it is meant a cell that has the ability under appropriate conditions of producing progeny of several different cell types that are derivatives of all of the three germinal layers (endoderm, mesoderm, and ectoderm). Pluripotent stem cells are capable of forming teratomas. Examples of pluripotent stem cells are embryonic stem (ES) cells, embryonic germ stem (EG) cells, embryonal carcinoma stem (EC) cells, and induced pluripotent stem (iPS) cells. PS cells may be from any organism of interest, including, e.g., human; primate; non-human primate; canine; feline; neurine; equine; porcine; avian; camel; bovine; ovine, and so on.

By "embryonic stem cell" or "ES cell" it is meant a cell that a) can self-renew, b) can differentiate to produce all types of cells in an organism, and c) is derived from a developing organism or is an established ES cell line which was derived from a developing organism. ES cell may be derived from the inner cell mass of the blastula, or from the epiblast, of a developing organism. ES cell may be derived from a blastomere generated by single blastomere biopsy (SBB) involving removal of a single blastomere from the developing organism. In general, SBB provides a non-destructive alternative to inner cell mass isolation. SBB and generation of hES cells from the biopsied blastomere is described in Cell Stem Cell, 2008 Feb. 7; 2(2):113-7. ES cells can be cultured over a long period of time while maintaining the ability to differentiate into all types of cells in an organism. In culture, ES cells typically grow as flat colonies with large nucleo-cytoplasmic ratios, defined borders and prominent nucleoli. In addition, hES cells express SSEA-3, SSEA-4, TRA-1-60, TRA-1-81, and Alkaline Phosphatase, but not SSEA-1. Examples of methods of generating and characterizing ES cells may be found in, for example, U.S. Pat. Nos. 7,029,913, 5,843,780, and 6,200,806, the disclosures of which are incorporated herein by reference. Examples of ES cells include naïve ES cells.

By "embryonic germ stem cell", embryonic germ cell" or "EG cell" it is meant a cell that a) can self-renew, b) can differentiate to produce all types of cells in an organism, and c) is derived from germ cells and germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841: Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPS cell" it is meant a cell that a) can self-renew, b) can differentiate to produce all types of cells in an organism, and c) is derived from a somatic cell. iPS cells have an ES cell-like morphology, growing as flat colonies with large nucleo-cytoplasmic ratios, defined borders and prominent nucleoli. In addition, iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. iPS cells may be generated by providing the cell with "reprogramming factors", i.e., one or more, e.g., a cocktail, of biologically active factors that act on a cell to alter transcription, thereby reprogramming a cell to pluripotency. Examples of methods of generating and characterizing iPS cells may be found in, for example, Application Nos. US20090047263, US20090068742, US20090191159, US20090227032, US20090246875, and US20090304646, the disclosures of which are incorporated herein by reference.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e., ectoderm, mesoderm and endoderm. For example, somatic cells would include both neurons and neural progenitors, the latter of which may be able to self-renew and naturally give rise to all or some cell types of the central nervous system but cannot give rise to cells of the mesoderm or endoderm lineages.

The term "cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time).

By "endoderm" it is meant the germ layer formed during animal embryogenesis that gives rise to the gastrointestinal tract, respiratory tract, endocrine glands and organs, certain structures of the auditory system, and certain structures of the urinary system.

By "mesoderm" it is meant the germ layer formed during animal embryogenesis that gives rise to muscles, cartilage, bones, dermis, the reproductive system, adipose tissue, connective tissues of the gut, peritoneum, certain structures of the urinary system, mesothelium, notochord, and spleen.

By "ectoderm" it is meant the germ layer formed during animal embryogenesis that gives rise to the nervous system, tooth enamel, epidermis, hair, nails, and linings of mucosal tissues.

By "bone morphogenic proteins" or "BMPs" it is meant the family of growth factors that is a subfamily of the transforming growth factor β (TGF β) superfamily. BMPs (e.g. BMP1, BMP2, BMP3, BMP4, BMP5, BMP6, BMP7, BMP8a, BMP8b, BMP9/GDF, BMP10, BMP11/GDF11, BMP12/GDF7, BMP13/GDF6, BMP14/GDF5, BMP15/GDF9B) were first discovered by their ability to induce the formation of bone and cartilage. BMPs interact with specific receptors on the cell surface, referred to as bone morphogenetic protein receptors (BMPRs). Signal transduction through BMPRs results in mobilization of members of the SMAD family of proteins, which in turn modulate transcription of target genes. Inhibitors of BMP signaling, can readily be identified by one of ordinary skill in the art by any of a number of methods, for example competitive binding assays for binding to BMP or BMP receptors, functional assays, e.g., measuring enhancement of activity of downstream signaling proteins such as relocalisation of SMADs, such as, BR-Smad to the nucleus and transcriptional activation of downstream gene targets as known in the art.

By "transforming growth factor betas", "TGF-βs", and "TGFBs" it is meant the TGFB secreted proteins belonging to the subfamily of the transforming growth factor β (TGFβ) superfamily. TGFBs (TGFB1, TGFB2, TGFB3) are multifunctional peptides that regulate proliferation, differentiation, adhesion, and migration and in many cell types. The mature peptides may be found as homodimers or as heterodimers with other TGFB family members. TGFBs interact with transforming growth factor beta receptors (TGF-βRs, or TGFBRs) on the cell surface, which binding activates MAP kinase-, Akt-, Rho- and Rac/cdc42-directed signal transduction pathways, the reorganization of the cellular architecture and nuclear localization of SMAD proteins, and the modulation of target gene transcription. Inhibitors of TGFB signaling, can be readily be identified by one of ordinary skill in the art by any of a number of methods, for example competitive binding assays for binding to TGFB or TGFB receptors, or functional assays, e.g. measuring suppression of activity of downstream signaling proteins such as MAPK, Akt, Rho, Rac, and SMADs, e.g., AR-Smad, etc., as well known in the art.

By "Wnts" it is meant the family of highly conserved secreted signaling molecules which play key roles in both embryogenesis and mature tissues. The human Wnt gene family has at least 19 members (Wnt-1, Wnt-2, Wnt-2B/Wnt-13, Wnt-3, Wnt3a, Wnt-4, Wnt-5A, Wnt-5B, Wnt-6, Wnt-7A, Wnt-7B, Wnt-8A, Wnt-8B, Wnt-9A/Wnt-14, Wnt-9B/Wnt-15, Wnt-10A, Wnt-10B, Wnt-11, Wnt-16). Wnt proteins modulate cell activity by binding to Wnt receptor complexes that include a polypeptide from the Frizzled (Fz) family of proteins and a polypeptide of the low-density lipoprotein receptor (LDLR)-related protein (LRP) family of proteins. Once activated by Wnt binding, the Wnt receptor complex will activate one or more intracellular signaling cascades. These include the canonical Wnt signaling pathway; the Wnt/planar cell polarity (Wnt/PCP) pathway; and the Wnt-calcium (Wnt/Ca2+) pathway.

By culturing under "non-adherent conditions" it is meant culturing under conditions that suppress the adhesion of cells to the vessel in which they are cultured, e.g., the bottom of a tissue culture plate or flask. In some instances, the cells are naturally non-adherent, i.e., they will not adhere to a surface unless the surface is coated with a matrix composition, e.g., fibronectin, laminin, poly-ornithin, poly-lysine, collagen IV, matrigel, and polycarbonate membranes. In some instances, cells may be maintained in a non-adherent state by agitating the culture.

By culturing under "adherent conditions" it is meant culturing under conditions that promote the adhesion of cells to the container in which they are cultured, e.g. the bottom of a tissue culture plate or flask. In some instances, cells may be induced to adhere to the container simply by keeping the culture stationary. In some instances, the wall of the container to which it is desirable to promote adhesion may be coated with a composition to which the cells may adhere, e.g., fibronectin, laminin, poly-ornithin, poly-lysine, collagen IV, matrigel, and polycarbonate membranes.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual", "subject", "host", and "patient" are used interchangeably herein and refer to any mammalian subject for whom diagnosis, treatment, or therapy is desired, particularly humans.

The term "medium" in context of cell culture or the phrase "cell culture medium" or "cell medium" refer to a cellular growth medium suitable for culturing of a cell population of interest. Examples of cell culture medium include Minimum Essential Medium (MEM), Eagle's Medium, Dulbecco's Modified Eagle Medium (DMEM), Dulbecco's Modified Eagle Medium: Nutrient Mixture F-12 (DMEM/F12), F10 Nutrient Mixture, Ham's F10 Nutrient Mix, Ham's F12 Nutrient Mixture, Medium 199, RPMI, RPMI 1640, reduced serum medium, basal medium (BME), DMEM/F12 (1:1), Neurobasal medium, and the like, and combinations thereof. The medium or cell culture medium may be modified by adding one or more factors, such as, supplements, differentiation factors, anti-apoptotic agents.

The term "isolated" in context of cells or cell population refers to cells that are in an environment other than their native environment, such as, apart from tissue of an organism.

The phrase "differentiation factor(s)" as used herein refers to the agent(s) that are included in the medium for culturing cells of the present disclosure, which agent(s) promote the differentiation of the cells from a first cell type to a second cell type, where the second cell type is differentiated compared to the first cell type.

In the context of cell ontogeny, the adjective "differentiated" is a relative term. A "differentiated cell" is a cell that has progressed further down the developmental pathway than the cell it is being compared with. Thus, pluripotent embryonic stem cells can differentiate to lineage-restricted precursor cells. These in turn can be differentiated further to cells further down the pathway, or to an end-stage differentiated cell, such as GABAergic interneuron.

"Feeder cells" or "feeders" are terms used to describe cells of one type that are co-cultured with cells of another type, to provide an environment in which the cells of the second type can grow. pPS cell populations are said to be "essentially free" of feeder cells if the cells have been grown through at least one round after splitting in which fresh feeder cells are not added to support the growth of pPS cells.

As used herein, "expression" and grammatical equivalents thereof, in the context of a marker, refers to production of the marker as well as level or amount of the marker. For example, expression of a marker or presence of a marker in a cell or a cell is positive for a marker, refers to expression of the marker at a level that is similar to a positive control level. The positive control level may be determined by the level of the marker expressed by a cell known to have the cell fate associated with the marker. Similarly, absence of expression of a marker or a cell is negative for a marker, refers to expression of the marker at a level that is similar to a negative control level. The negative control level may be determined by the level of the marker expressed by a cell known to not have the cell fate associated with the marker. As such, absence of a marker does not simply imply an undetectable level of expression of the marker, in certain cases, a cell may express the marker but the expression may be low compared to a positive control or may be at a level similar to that of a negative control.

As used herein, "marker" refers to any molecule that can be measured or detected. For example, a marker can include, without limitations, a nucleic acid, such as, a transcript of a gene, a polypeptide product of a gene, a glycoprotein, a carbohydrate, a glycolipid, a lipid, a lipoprotein, a carbohydrate, or a small molecule (for example, a molecule having a molecular weight of less than 10,000 amu).

A "variant" polypeptide means a biologically active polypeptide as defined below having at least 70%, 75%, 80%, 85%, 90%, 95%, 98%, or 99% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, at least about 95%, or at least about 99%. The variant polypeptides can be naturally or non-naturally glycosylated, i.e., the polypeptide has a glycosylation pattern that differs from the glycosylation pattern found in the corresponding naturally occurring protein. The variant polypeptides can have post-translational modifications not found on the natural polypeptide.

The terms 'enriching" or "enriched" are used interchangeably herein and mean that the yield (fraction) of cells of one type is increased by at least 10% over the fraction of cells of that type in the starting culture or preparation.

A "growth environment" is an environment in which cells of interest will proliferate, differentiate, or mature in vitro.

Features of the environment include the medium in which the cells are cultured, any growth factors or differentiation-inducing factors that may be present, and a supporting structure (such as a substrate on a solid surface) if present.

DETAILED DESCRIPTION

As noted above, methods and systems for generating MGE precursor cells in vitro as well as compositions of enriched MGE precursor cells are provided. The methods and systems provide efficient production of functional MGE precursors, which differentiate into functional GABAergic interneurons.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a SMAD inhibitor" includes a plurality of such inhibitors and reference to "the ROCK inhibitor" includes reference to one or more ROCK inhibitor and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Method for Generating MGE Precursor Cells

In certain embodiments, a method of producing medial ganglionic eminence (MGE) precursor cells from primate pluripotent stem (pPS) cells is provided.

In general, the pPS are maintained in an undifferentiated state till the method for production of MGE precursor cells is commenced.

The method may include culturing the pPS cells in a serum free medium comprising an activator of sonic hedgehog pathway and a neural inducing supplement to generate the MGE precursor cells. The pPS cells may be cultured as an adherent culture or a suspension culture.

In certain embodiments, at the start of the method for production of MGE precursor cells, pPS are plated cells into a cell culture container with an adherent substrate that facilitate the attachment of the pPS cells and the cells are contacted with serum free medium comprising an activator of sonic hedgehog pathway and a neural inducing supplement to generate the MGE precursor cells.

In certain embodiments, the method may include culturing the pPS cells in a serum free medium comprising an activator of sonic hedgehog pathway and a neural inducing supplement to generate embryoid bodies (EBs), wherein the EBs comprise the MGE precursor cells.

In certain embodiments, at the start of the method for production of MGE precursor cells, pPS may be plated cells in suspension in culture containers having a substrate with low adhesion properties that allows suspension embryoid bodies to form. In an exemplary method, confluent monolayer cultures of pPS cells are harvested and then plated in non-adherent cell culture plates, keeping the cells in suspension.

In certain cases, CollagenaseIV/Dispase may be used for preferential selection for pPS colonies. The colonies may be trypsinized to single cells and plated into low-attachment round-bottom plates to form suspension EB.

In certain cases, the process of differentiation can be induced by causing the pPS cells to differentiate, e.g., to form embryoid bodies or aggregates: for example, by overgrowth of a donor pPS cell culture, or by culturing pPS cells in suspension in culture vessels having a substrate with low adhesion properties that allows embryoid bodies to form, or culturing pPS in absence of feeder layer. In an exemplary method, confluent monolayer cultures of pPS cells are harvested and then plated in non-adherent cell culture plates, keeping the cells in suspension, and providing regular feeding with nutrient medium.

Alternatively or in addition, the differentiation process can be initiated by culturing with certain factors that prevent the cells from maintaining the undifferentiated phenotype. The initial differentiation factors need not limit differentiation into the MGE precursor cell lineage, but should be inclusive of MGE precursor cell or their precursors within the range of cell types in the differentiated population.

At some stage, the culture can be directed more specifically into the MGE precursor cell lineage. This can be done by including in the culture medium a factor that more specifically promotes the generation and proliferation of MGE precursor cell. Exemplary factors that promote the formation and/or growth of MGE precursor cells include neural inducing supplements as provided herein, activators of shh signaling, inhibitors of BMP-signaling, inhibitors of TGF-β signaling, Wnt inhibitors, and anti-apoptotic agents, and in some cases can include activator(s) of FGF signaling.

Exemplary methods for generating MGE precursor cells are described below.

In certain cases, the method may include a step of generation of sEB following by a step of generation of aEB. In other cases, the step of generation of sEB may be replaced by an adherent culture.

Generation of Suspension Embryoid Bodies (sEB)

In an exemplary method, culturing pPS cells in suspension in culture vessels having a substrate with low adhesion properties that allows suspension embryoid bodies to form may be carried out in the presence of an activator of shh and a neural inducing supplement, such as B27 or NS21. The pPS cells may be cultured in suspension in absence of a feeder layer for 0 day-9 days before an activator of shh and/or neural inducing supplement is added to the culture medium, for example, the pPS cells may be cultured in suspension for at least 0 hr, 1 hr, 3 hrs, 6 hrs, 12 hrs, 18 hrs, 24 hrs, 36 hrs, 48 hrs, 2 days, 3 days, 4 days, 5 days, 6 days, 7 days, 8 days, or 9 days before an activator of shh and/or neural inducing supplement is added to the culture medium. Accordingly, the pPS are induced to form sEBs in the presence of a neural inducing supplement as described herein and an activator of shh signaling.

The pPS cell may be cultured in suspension to form sEB for a period of at least 1 day, e.g., 1-100 days, 1-60 days, 1-50 days, 2-100 days, 2-50 days, 3-100 days, 4-100 days, 5-10 days, or 7-10 days, or 25-100 days in the presence of a neural inducing supplement as described herein and an activator of shh signaling. In cases, where the pPS cell may be cultured in suspension to form sEB for a period of less than 9 days, an activator of shh and/or neural inducing supplement may be added to the culture medium within 0-8 days from the start of the culture of pPS cells to form sEB.

In certain embodiments, the pPS are plated in suspension, in culture containers having a substrate with low adhesion properties, in a cell culture medium that includes a neural inducing supplement as provided herein and an activator of shh signaling.

In addition to a neural inducing supplement as provided herein and an activator of shh signaling, the culture medium for culturing pPS cells in suspension to form sEBs may contain one or more of an anti-apoptotic agent, SMAD inhibitor (e.g., TGE-β inhibitors, BMP inhibitors, Activin inhibitor, Nodal inhibitor, or growth differentiation factor (GDF) signaling pathway inhibitor), and Wnt inhibitor.

In certain cases, the method for producing MOTE precursor cells from pPS cells may include culturing the pPS cells in a medium that includes an anti-apoptotic agent, e.g., a ROCK inhibitor, for about 1 hr-35 days, e.g., at least 1 hr, at least 3 hrs, at least 10 hrs, at least 24 hrs, at least 36 hrs, at least 48 hrs, at least 2 days, at least 3 days, such as, 4 days, 5 days, 6 days, 7 days, 8 days, 9 days, 15 days, 20 days, 25 days, or 35 days. An exemplary method may include plating the pPS cells in suspension in a medium containing an anti-apoptotic agent, culturing the pPS cells for a period of 1 hr-35 days in the presence of the anti-apoptotic agent. In certain cases, the anti-apoptotic agent may be present from the start of culturing of pPS cells in suspension and may be removed after 1 hr-35 days, such as 1 day to 7 days, e.g. 1 days, 2 days, 3 days, 4 days, 5 days, 6 days, or 7 days.

In certain cases, the anti-apoptotic agent may be present transiently during differentiation of the pPS into MGE cells, e.g., the anti-apoptotic agent may be present in the culture medium on day 1 when the pPS cells are exposed to the neural inducing supplement as provided herein and an activator of shh signaling. The differentiation of the pPS cell may be carried out in the presence of neural inducing supplement as provided herein, an activator of shh signaling, and an anti-apoptotic agent for 1 hr to 35 days are noted above, after which the culturing may be continued in the absence of the anti-apoptotic agent.

In certain cases, the method for producing MGE precursor cells from pPS cells may include culturing the pPS cells in a medium that includes one or more inhibitors of wnt. Although the Wnt signal inhibitor may be added to the medium already at the start of cultivation of pPS cells, it may be added to the medium after several days of cultivation (for example, at a time within 10 days of cultivation). In certain cases, the Wnt signal inhibitor is added to the medium at a time within 5 days of start of culturing of pPS cells in suspension, such as, within 0 days, 1 day, or 3 days. The wnt inhibitor may be present throughout the step of generation of sEB or may be present for a period of 5 days-10 days, e.g., 5 days, 6 days, 7 days, 8 days, 9 days, or 10 days, after which the culture may be continued in absence of the writ inhibitor (s).

In certain cases, the method for producing MGE precursor cells from pPS cells may include culturing the pPS cells in a medium that includes one or more inhibitors of SMAD. Although the SMAD signal inhibitor may be added to the medium already at the start of cultivation of pPS cells, it may be added to the medium after several days of cultivation (for example, at a time within 10 days of cultivation). In certain cases, the one or more SMAD signal inhibitors are added to the medium at a time within 5 days of start of culturing of pPS cells in suspension, such as, within 0 days, 1 day, or 3 days. The wnt inhibitor may be present throughout the step of generation of sEB or may be present for a period of 5 days-10 days.

In certain cases, the pPS are differentiated in the presence of shh activator, neural inducing supplement as provided herein, and SMAD inhibitor(s) for a period of 5 to 15 days (e.g., 5-10 days, such as, 5 days, 6 days, 7 days, 8 days, 9 days, 10 days, 12 days) after which the differentiation may be continued in absence of the SMAD inhibitor(s).

In certain embodiments, the method of producing medial ganglionic eminence (MGE) precursor cells from primate pluripotent stem (pPS) cells may include culturing the pPS cells in a serum free medium to generate sEBs, wherein the sEBs include the MGE precursor cells, wherein the serum free medium includes an activator of sonic hedgehog pathway, an anti-apoptotic agent, an inhibitor of SMAD, an inhibitor of Wnt and B27. The sEB produced by the methods described herein include a population of MGE precursor cells.

In certain embodiments, the method of producing medial ganglionic eminence (MGE) precursor cells from primate pluripotent stem (pPS) cells may include culturing the pPS cells in a serum free medium as suspension culture to generate the MGE precursor cells, wherein the serum free medium includes an activator of sonic hedgehog pathway, an anti-apoptotic agent, an inhibitor of SMAD, an inhibitor of Wnt and B27. In certain cases, the sEB may be dissociated and plated as a monolayer to generate a monolayer that includes MGE precursor cells.

In certain cases, the sEBs may be dissociated and plated as a monolayer after about 5 days from the beginning of the differentiation of pPS cells. For example, the sEBs may dissociated and plated as a monolayer within 1-100 days after formation of the sEB, e.g., 1-75 days, 1-50 days, 1-30 days, 1-10 days. In exemplary cases, sEB may be dissociated and plated as a monolayer after about 10 days of formation of the sEB, e.g., 10-50 days, 10-40 days, 10-30 days, 10-20 days, 10 days, 12 days, etc. The differentiation factors as well as additives, supplements, or factors, used as well as the timing of addition/removal of the same may be as disclosed above.

In certain embodiments, the method of producing medial ganglionic eminence (MGE) precursor cells from primate pluripotent stem (pPS) cells may include culturing the pPS cells in a serum free medium as an adherent culture to generate the MGE precursor cells, wherein the serum free medium includes an activator of sonic hedgehog pathway, an anti-apoptotic agent, an inhibitor of SMAD, an inhibitor of Wnt and B27.

In general, the MGE precursor cells produced by the method described herein express a marker of MGE precursor cells, such as, NKX2.1.

In certain cases, the PS cells at the start of the culturing to generate MGE precursor cells are present at a cell density of $10^3$ to $10^7$ cells/ml.

The medium used in the suspension culture can be prepared using any basal medium. The medium may be BME medium, BGJb medium, CMRL 1066 medium, Glasgow MEM medium, Improved MEM Zinc Option medium, IMDM medium, Medium 199 medium, Eagle's MEM medium, DMEM medium, Ham's medium, RPMI 1640 medium, Fischer's medium, Neurobasal medium, and a mixed medium thereof and the like. The medium may be modified by addition of additives, supplements, or factors, as disclosed herein.

A cell culture container with an adherent substrate may be used in methods of culturing the pPS as an adherent culture. The differentiation factors as well as additives, supplements, or factors, used as well as the timing of addition/removal of the same may be as disclosed above.

Generation of Adherent Embryoid Bodies (aEB)

In certain cases, the sEBs generated by the above described methods may be plated into a cell culture container with an adherent substrate that facilitate the attachment of the sEB to form adherent EBs. In general, the sEB may be plated onto a cell culture container with an adherent substrate in a culture medium containing a neural inducing supplement as provided herein and an activator of shh signaling.

In embodiments where the pPS cells are cultured as an adhesion culture, as noted above, the method may further culturing the pPS cells in the serum free medium comprising the activator of sonic hedgehog pathway and the neural inducing supplement to generate aEBs, which aEBs include MGE precursor cells.

The sEB replated and cultured in adhesion culture to form aEB may be cultured for a period of 1-100 days. In exemplary methods, the replating of sEB may involve the steps of dissociating the EBs mechanically or enzymatically to produce single cells or clusters of cells, plating the dissociated cells on an adherent substrate to provide an adherent monolayer; and culturing the adherent monolayer to generate aEBs. In certain methods, the sEBs are not dissociated before further culturing in adherent conditions.

In certain embodiments, the method for generating MGE precursor cells from pPS cells may include culturing the pPS cells in a serum free medium comprising an activator of sonic hedgehog pathway and a neural inducing supplement to generate sEBs and plating of the sEBs on a cell culture container with an adherent substrate and culturing the plated sEBs on the adherent substrate in the serum free medium comprising the activator of sonic hedgehog pathway and the neural inducing supplement to generate aEBs, which aEBs include MGE precursor cells.

In certain cases, the aEBs may be dissociated and replated as a monolayer, which monolayer may be cultured in a serum free medium that includes the activator of sonic hedgehog pathway and the neural inducing supplement to generate MGE precursor cells.

The cell culture medium for culturing of the adhesion culture to generate aEB from the sEB may also include one or more of factors such as, an anti-apoptotic agent, an inhibitor of SMAD, and an inhibitor of Wnt. The factors may be present at the start of the adhesion culture or may be added within 5 days of initiation of the adhesion culture, such as, 0 hr, 1 hr, 3 hr, 10 hr, 1 day, 2 days, or 3 days from the initiation of the adhesion culture. The factors may be removed from the adhesion culture after 1 day to 20 days of culturing.

In certain embodiments, the method for generating MGE precursor cells from pPS cells may include culturing the cells of the sEBs obtained by the methods described herein in an adhesion culture in a medium that includes activator of sonic hedgehog pathway, a neural inducing supplement, Wnt and SMAD inhibitors, for a period of 4-20 days, followed by culturing the adhesion culture for 8-20 days in a medium that includes activator of sonic hedgehog pathway and a neural inducing supplement but does not include Wnt and SMAD inhibitors.

The aEBs generated by the methods described herein include a population of MGE precursor cells. In general, the MGE precursor cells present in the aEBs produced by the method described herein express NKX2.1 and FOXG1. In certain cases, the MGE precursor cells produced by the methods disclosed herein may express one or more markers of MGE precursor cells, such as, NKX2.1, LHX6, LHX7/8, FOXG1, OLIG2, DLX1/2, and ASCL1.

In certain embodiments, the MGE precursor cells produced by the methods described herein may also include a population of cells differentiated from the MGE precursor cells, such as, interneurons, e.g., GABAergic interneurons.

In general, the methods described herein result in generation of MGE precursor cells at a high efficiency, resulting in cell cultures where at least 50% (e.g. 65%, 70%, 75%, 80%, 85%, 90%, or 95%) of the cells in the cell culture are MGE precursor cells.

As such, the method may include culturing pPS cells in a serum free culture medium comprising activator of sonic hedgehog pathway and a neural inducing supplement for a period of 10-100 days (e.g. 5-50 days) to generate MGE precursor cells, wherein the pPS cells are cultured in adherent or suspension culture, wherein the pPS cells are induced to differentiate prior to culturing in the presence of activator of sonic hedgehog pathway and a neural inducing supplement. As such, the pPS cells may include differentiated cells, such as EBs, prior to culturing OS cells in a serum free culture medium comprising activator of sonic hedgehog pathway and a neural inducing supplement. In certain cases, the serum free culture medium may additionally include an anti-apoptotic agent, an inhibitor of SMAD, and an inhibitor of Wnt.

In certain cases, the aEBs obtained from the sEB may be replated in a suspension culture to form sEBs or dissociated and replated as a monolayer in adherent culture.

Culturing of pPS cells as an adherent culture in a method for generating MGE precursor cells is further described below.

Adherent Culture for Generation of MGE Precursor Cells

As noted above, in certain embodiments, at the start of the method for production of MGE precursor cells, pPS are plated cells into a cell culture container with an adherent substrate that facilitate the attachment of the pPS cells and the cells are contacted with serum free medium comprising an activator of sonic hedgehog pathway and a neural inducing supplement to generate the MGE precursor cells.

In certain cases, the MGE precursor cells generated in the adherent culture may be present in the aEBs.

In some cases, the aEB produced by the subject culture method may be dissociated and replated as a monolayer and cultured in a serum free medium comprising an activator of sonic hedgehog pathway and a neural inducing supplement to generate the MGE precursor cells. The aEB may be maintained in the of supplements and factors as described herein for a period of time of 1-100 days before being replated in a suspension culture and cultured further as sEB or before being dissociated and replated as a monolayer in an adherent culture. In certain cases, the period of time may be 1-75 days, 1-50 days, 1-30 days, 1-10 days, e.g., 10-50 days, 10-40 days, 10-30 days, 10-20 days, 5 days, 10 days, 20 days, or 30 days.

Adherent substrates known in the art as well as those described herein may be used for culturing the pPS as an adherent culture in a method for generating MGE precursor cells.

The pPS cells may be grown as an adherent culture for a period of time before contacting with serum free medium comprising an activator of sonic hedgehog pathway and a neural inducing supplement. In certain cases the pPS cells may be induced to differentiate by overgrowth of a donor pPS cell culture, or culturing pPS in absence of feeder layer, or culturing pPS cells in presence of FGF, or the like. Alternatively or in addition, the differentiation process can be initiated by culturing with certain factors that prevent the cells from maintaining the undifferentiated phenotype. The initial differentiation factors need not limit differentiation into the MGE precursor cell lineage, but should be inclusive of MGE precursor cell or their precursors within the range of cell types in the differentiated population.

At some stage, the culture can be directed more specifically into the MGE precursor cell lineage. This can be done by including in the culture medium a factor that more specifically promotes the generation and proliferation of MGE precursor cell. Exemplary factors that promote the formation and/or growth of MGE precursor cells include neural inducing supplements as provided herein, activators of shh signaling, inhibitors of BMP-signaling, inhibitors of TGF-β signaling, Wnt inhibitors, and anti-apoptotic agents, and in some cases can include activator(s) of FGF signaling.

Exemplary methods for generating MGE precursor cells are described below.

The pPS cells may be cultured in adherent conditions for 0 day-9 days before an activator of shh and/or neural inducing supplement is added to the culture medium, for example, the pPS cells may be cultured in adherent conditions for at least 0 hr, 1 hr, 3 hrs, 6 hrs, 12 hrs, 18 hrs, 24 hrs, 36 hrs, 48 hrs, 2 days, 3 days, 4 days, 5 days, 6 days, 7 days, 8 days, or 9 days before an activator of shh and/or neural inducing supplement is added to the culture medium. In certain embodiments, the pPS are differentiated in absence of a feeder cell layer.

In cases, where the pPS cell may be cultured in adherent conditions in a culture medium containing an activator of shh and/or neural inducing supplement for a period of 1-100 days from the start of the culture of pPS cells to form MGE precursor cells.

In addition to a neural inducing supplement as provided herein and an activator of shh signaling, the culture medium for culturing pPS cells in adherent conditions may contain one or more of an anti-apoptotic agent, SMAD inhibitor (e.g., TGF-β inhibitors, BMP inhibitors, Activin inhibitor, Nodal inhibitor, or GDF signaling pathway inhibitor), and Wnt inhibitor.

The timing of addition and removal of differentiation factors may be as described for the aEB formation above.

In certain cases, the method for producing MGE precursor cells from pPS cells may include culturing the pPS cells in a medium that includes an anti-apoptotic agent, e.g., a ROCK inhibitor, for about 1 hr-35 days, e.g., at least 1 hr, at least 3 hrs, at least 10 hrs, at least 24 hrs, at least 36 hrs, at least 48 hrs, at least 2 days, at least 3 days, such as, 4 days, 5 days, 6 days, 7 days, 8 days, 9 days, 15 days, 20 days, 25 days, or 35 days. An exemplary method may include plating the pPS cells in adherent culture in a medium containing an anti-apoptotic agent, culturing the pPS cells for a period of 1 hr-35 days in the presence of the anti-apoptotic agent. In certain cases, the anti-apoptotic agent may be present from the start of culturing of pPS cells for generation of MGE precursor cells and may be removed after 1 hr-35 days, such as 1 day to 7 days.

In certain cases, the method for producing MGE precursor cells from pPS cells may include culturing the pPS cells in a medium that includes one or more inhibitors of wnt. Although the Wnt signal inhibitor may be added to the medium already at the start of culturing of pPS cells, it may be added to the medium after several days of cultivation (for example, at a time within 10 days of culturing). In certain cases, the Wnt signal inhibitor is added to the medium at a time within 5 days of start of culturing of pPS cells in adherent condition, such as, within 0 days, 1 day, or 3 days. The wnt inhibitor may be present throughout the culturing or may be present for a period of 5 days-10 days.

In certain cases, the method for producing MGE precursor cells from pPS cells may include culturing the pPS cells in a medium that includes one or more inhibitors of SMAD. Although the SMAD signal inhibitor may be added to the medium already at the start of culturing of pPS cells, it may be added to the medium after several days of culturing for generation of MGE precursor cells (for example, at a time within 10 days of culturing). In certain cases, the one or more SMAD signal inhibitors are added to the medium at a time within 5 days of start of culturing of pPS cells in adherent condition, such as, within 0 days, 1 day, or 3 days. The wnt inhibitor may be present throughout the culturing to generate MGE precursor cells or may be present for a period of 5 days-10 days.

In certain embodiments, the method of producing medial ganglionic eminence (MGE) precursor cells from primate pluripotent stem (pPS) cells may include culturing the pPS cells in adherent condition to generate MGE precursor cells, wherein the culture medium includes an activator of sonic hedgehog pathway, an anti-apoptotic agent, an inhibitor of SMAD, an inhibitor of Wnt and B27.

In certain cases, the PS cells at the start of the culturing to generate MGE precursor cells are present at a cell density of $10^3$ to $10^7$ cells/ml.

As noted above, a serum free medium may be used in the method of generating MGE precursor cells from pPS cells. A serum-free medium means a medium not containing an unadjusted or unpurified serum, such as, fetal bovine serum, fetal calf serum. The serum-free medium may include a serum replacement, such as, those described herein, e.g., B27 or NS21.

Culture of NICE Precursor Cells

The sEBs and aEBs generated by the methods described herein may be dissociated, enzymatically or mechanically, and cultured as a monolayer on a cell culture vessel with adherent substrate. Accordingly, the IME precursor cells present in the sEB and aEBs may be cultured as a monolayer.

In certain cases, culturing of MGE precursor cells in a monolayer may be carried out for a period of 1-100 days, such as 10 days-15 days.

The culturing of MGE precursor cells in a monolayer may be carried out in a culture medium that contains a neural inducing supplement as provided herein and an activator of shh signaling.

In certain cases, the MGE precursor cells generated by the method described herein may be cultured in a culture medium that promote generation of neurons, such as, inhibitory interneurons, e.g., GABAergic interneurons. Accordingly, sEB, aEB, and monolayer produced from dissociation of sEBs and aEBs generated by the methods described herein and containing MGE precursor cells may be contacted with a culture medium that promotes differentiation of the MGE precursor cells into post mitotic neurons. In certain cases, this culture medium may not include SMAD inhibitors. In addition, in certain cases, this culture medium may include SMAD activators. As such, the culture medium may include SMAD activators in order to increase the population of interneurons present in the MGE precursor cells generated by the protocols described herein. Exemplary SMAD activators include TGFs (e.g., TGFβ3), BMPs (e.g., BMP2, BMP4, BMP8), Activin, Nodal, GDF, and IDE1.

In certain cases, the culture medium to promote differentiation of the MGE precursor cells to interneurons may include a NOTCH inhibitor, BDNG, GDNF, NT3, NT4, camp, vitamin c, serum, matrigel, insulin, IGF, SDF1a, Neuregulin1, TGFβ.

The culturing of MGE precursor cells in a monolayer may lead to proliferation of MGE precursor cells and/or differentiation of MGE precursor cells into cells having a neuronal cell fate. In certain cases, the MGE precursor cells that differentiate into cells having a neuronal cell fate express DLX1/2, TUJ, MAP2, GAD1/2, and GABA, and may express one or more of NKX2.1, ASCL1, LHX6, LHX7/8, DCX, NEUN, and VGAT, and may express subtype markers calbindin, calretinin, somatostatin, and pare albumin.

In certain cases, the MGE precursor cells generated by the method described herein may be co-cultured with a support cell population to induce differentiation of the MGE precursor cells into interneurons, such as, GABAergic interneurons.

Propagation of pPS Cells in an Undifferentiated State pPS cells can be propagated continuously in culture, using culture conditions that promote proliferation without promoting differentiation. Exemplary ES medium is made with 80% DMEM (such as Knockout DMEM "KO DMEM"), 20% of either defined fetal bovine serum (FBS, Hyclone) or serum replacement (e.g., knockout serum replacement (KSR)), 1% non-essential amino acids (NEAA), 1% pen-step-glutamine (1 mM L-glutamine), 0.0008% β-mercaptoethanol, and 10 ng/ml FGF-basic (bFGF).

The pPS cells can be expanded in the undifferentiated state by culturing in an environment that inhibits differentiation. Traditionally, pPS cells are cultured on a layer of feeder cells derived from embryonic or fetal tissue of the mouse. Culture plates are plated with 375,000 irradiated mouse embryonic fibroblasts (mEFs) per well (irradiated. to inhibit proliferation but permit synthesis of factors that support pPS cells), and used 5 h to 10 days after plating. In certain embodiments, human feeder cells may also be used.

pPS cells can be maintained in an undifferentiated state even without feeder cells. The environment for feeder-free cultures includes a suitable culture substrate, particularly an extracellular matrix such as Matrigel® or laminin. The pPS cells are plated at >15,000 cells $cm^{-2}$ (optimally 90,000 $cm^{-2}$ to 170,000 $cm^{-2}$). Feeder-free cultures are supported by a nutrient medium containing factors that support proliferation of the cells without differentiation. Such factors may be introduced into the medium by culturing the medium with cells secreting such factors, such as irradiated (~4,000 rad) primary mouse embryonic fibroblasts, telomerized mouse fibroblasts, or human feeder cells derived from pPS cells. Medium can be conditioned by plating the feeders at a density of ~5-6×$10^4$ $cm^{-2}$ in a serum free medium such as KO DMEM supplemented with 20% serum replacement and 4 to 8 ng/mL bFGF. Medium that has been conditioned for 1-2 days is supplemented with further bFGF, and used to support pPS cell culture for 1-2 days. Features of the feeder-free culture method are further discussed in International Patent Publications WO99/20741 & WO01/51616; and Xu et al., Nat. Biotechnol. 19:971, 2001, which are herein incorporated by reference.

Factors

The methods and compositions of the present disclosure involve the use of various factors, such as, neural inducing supplements, anti-apoptotic agents, differentiation factors, and the like. Examples of neural inducing supplements, anti-apoptotic agents, differentiation factors used in the methods and compositions of the present disclosure are described below.

Neural Inducing Supplement

Exemplary neural inducing supplements include B27, NS21, or an equivalent supplement.

In certain embodiments, the neural inducing supplement may be B27. B-27® Serum-Free Supplement is available from Life Technologies. B27 supplement contains bovine serum albumin, transferrin, insulin, progesterone, corticosterone, triiodo-1-thyronine, retinol acetate, DL tocopherol, DL tocopherol acetate, Biotin, Linoleic acid, Linolenic acid, ethanolamine, Na Selenite, L-carnitine, glutathione reduced, catalase, superoxide dismutase, D-galactose and putrescine. In certain cases, B27-vitamin A may be used.

In certain cases, the neural inducing supplement may be NS21. NS21 is described in Y, Chen et al., J. Neurosci. Methods., 171:239, 2008. Y. Chen et al. showed that NS21 is equivalent to B27 supplement in a neuronal culture. The formulation of NS21 is described in Y. Chen et al. and is reproduced in Table 1 below.

TABLE 1

| | NS1 Formulation Final Concentration | | | |
|---|---|---|---|---|
| | µg/ml | µM | Stock (mg/ml) | For 400 ml NS21 (20 L final medium) |
| Albumin, bovine | 2500 | 37 | Add as powder | 50 g |
| Catalase | 2.5 | 0.010 | Add as powder | 50 mg |
| Glutathione (reduced) | 1.0 | 3.2 | Add as powder | 20 mg |
| Insulin | 4.0 | 0.6 | 10 | 8 ml |
| Superoxidase dismutase | 2.5 | 0.077 | Add as powder | 50 mg |

TABLE 1-continued

NS1 Formulation
Final Concentration

|  | μg/ml | μM | Stock (mg/ml) | For 400 ml NS21 (20 L final medium) |
|---|---|---|---|---|
| Holo transferrin | 5.0 | 0.062 | Add as powder | 100 mg |
| T3 (triiodol-1-thyronin) | 0.002 | 0.0026 | 2.0 | 20 μl |
| L-Carnitine | 2.0 | 1.2 | Add as powder | 40 mg |
| Ethanolamine | 1.0 | 16 | Liquid (1 g/ml) | 20 μl |
| D(+)-galactose | 15 | 83 | Add as powder | 300 mg |
| Putrescine | 16.1 | 183 | Add as powder | 322 mg |
| Sodium Selenite | 0.01435 | 0.083 | 1.0 | 280 μl |
| Ethanolic Stocks | | | | |
| Corticosterone | 0.02 | 0.058 | 2.0 | 0.2 ml |
| Linoleic acid | 1.0 | 3.5 | 100.0 | 0.2 ml |
| Linolenic acid | 1.0 | 3.5 | 100.0 | 0.2 ml |
| Lipoic acid (thioctic acid) | 0.047 | 0.2 | 4.7 | 0.2 ml |
| Progesterone | 0.0063 | 0.020 | 3.2 | 0.04 ml |
| Retinol acetate | 0.1 | 0.2 | 20.0 | 0.1 ml |
| Retinol, all trans (vit. A) | 0.1 | 0.3 | 10.0 | 0.2 ml |
| D, L-alpha-Tocopherol (vit. E) | 1.0 | 2.3 | 100.0 | 0.2 ml |
| D, L-alpha-Tocopherol acetate | 1.0 | 2.1 | 100.0 | 0.2 ml |

In certain cases, the neural inducing supplement may be present in the serum free medium for culturing pPS cells at a concentration ranging from 0.5% to 10%, for example, 0.5%-5%, e.g., 0.5%, 1%, 2%, or 3%.

In certain embodiments, the serum free medium comprising a shh activator and a neural inducing supplement for culturing of pPS to generate EBs does not include KSR or N2 supplement. In certain embodiments, the method of generating MGE precursor cells does not include culturing the pPS cells in a serum free medium comprising bFGF or FGF-2. In certain cases, the pPS cells are cultured in a serum free medium comprising a shh activator and a neural inducing supplement and not containing KSR or N2 supplement or bFGF or FGF-2 for a period of time sufficient to generate sEB or aEB.

In certain cases, the sEBs may be further cultured in a serum free medium comprising a shh activator and a neural inducing supplement and further containing one or more of KSR supplement, N2 supplement, bFGF, and FGF-2 for a period of sufficient to generate aEB.

In certain cases, the pPS cells may be cultured in a serum free medium comprising a shh activator and a neural inducing supplement and further containing one or more of KSR supplement, N2 supplement, bFGF, and FGF-2 for a period of sufficient to generate sEB. The additional supplements may be added at the same time as a shh activator and the neural inducing supplement as described herein or at a later time point, such as, after 5 days-2 weeks, such as, after 1 weeks-2 weeks after exposing the pPS cells to shh activator and the neural inducing supplement as described herein. In certain cases, the KSR supplement and/or N2 supplement may be present added at day 0 of differentiation, or later such as day 5, day 7, day 10, day 14, day 21, after contacting the pPS cells shh activator and the neural inducing supplement as described herein.

In certain embodiments, the cell culture medium used in the methods disclosed herein does not include serum replacements, such as, KSR or N2.

Anti-Apoptotic Agents

In certain embodiments of the methods and compositions described herein, an anti-apoptotic agent may be included in the medium for PS culturing cells.

In certain cases, the anti-apoptotic agent may be an inhibitor of Rho-associated protein kinase (ROCK). In certain cases, the ROCK inhibitor may be Y27632, HA-100, H-1152, (+)-trans-4-(1-aminoethyl)-1-(pyridin-4-ylaminocarbonyl) cyclohexane dihydro-chloride monohydrate (described in WO00078351, WO00057913), imidazopyridine derivatives (described in U.S. Pat. No. 7,348,339), substituted pyrimidine and pyridine derivatives (described in U.S. Pat. No. 6,943,172) and substituted isoquinoline-sulfonyl compounds (described in EP00187371), or GSK429286A, ROCKII inhibitor, or Thiazovivin, or an analog or derivative thereof.

The anti-apoptotic agent may be present at a concentration of 0.1 μM, 0.3 μM, 0.5 μM, 1 μM, at least about 1.3 μM, at least about 1.5 μM, at least about 2 μM, at least about 2.3 μM, at least about 2.5 μM, at least about 2.8 μM, at least about 3 μM, at least about 3.5 μM, at least about 4 μM, at least about 4.5 μM, at least about 5 μM, at least about 10 μM, at least about 20 μM, at least about 30 μM, at least about 40 μM or at least about 50 μM, such as, 0.5 μM-50 μM, 1 μM-25 μM, or 2.5 μM-20 μM.

Inhibitors of SMAD

In certain embodiments of the methods and compositions described herein, an inhibitor of SMAD may be present in the medium for culturing cells. In some embodiments, an inhibitor of SMAD can be present in the medium, used for culturing cells, at a concentration of 10 ng/ml, 200 ng/ml, 300 ng/ml, 400 ng/ml, 500 ng/ml, 1 μg/ml, 1.5 μg/ml, 2 μg/ml, 2.5 μg/ml, or 5 μg/ml for example, at a concentration of 500 ng/ml-3 μg/ml, e.g., 1 μg/ml-3 μg/ml.

The inhibitor of SMAD may be present at a concentration of at least about 0.01 μM, at least about 0.03 μM, at least about 0.1 μM, at least about 0.2 μM, at least about 0.25 μM, at least about 0.3 μM, at least about 1 μM, at least about 1.3 μM, at least about 1.5 μM, at least about 2 μM, at least about 2.3 μM, at least about 2.5 μM, at least about 2.8 μM, at least about 3 μM, at least about 3.5 μM, at least about 4 μM, at least about 4.5 μM, at least about 5 μM, at least about 10 μM, at least about 20 μM, at least about 30 μM, at least about 40 μM or at least about 50 μM, such as, 0.5 μM-50 μM, 1 μM-25 μM, or 5 μM-20 μM.

In certain embodiments, the inhibitor of SMAD may be an inhibitor of TGF-β signaling. For example, the SMAD inhibitor may be an ALK inhibitor, or antibody or a fragment thereof that binds to TGF-β1, TGF-β2, TGF-β3, TGF-β receptor I and/or II. In certain embodiments, the inhibitor of TGF-β signaling may be a small molecule inhibitor. In certain cases, the inhibitor of TGF-β signaling may be LY364947 (SD208), SM16, SB-505124, ALK5 Inhibitor II, SB-431542, LY2157299, LDN-193189, A83-01, (+)-ITD-1, ITD-1 (ethyl 4-([1,1'-biphenyl]-4-yl)-2,7,7-trimethyl-5-oxo-1,4,5,6,7,8-hexahydroquinoline-3-carboxylate), or ITDts.

In certain embodiments, the SMAD inhibitor may be BMPRIA-Fc, Noggin, or derivatives thereof.

In certain embodiments, the SMAD inhibitor may be a BMP pathway inhibitor, such as, dorsomorphin.

In certain embodiments, the SMAD inhibitor may be an Activin inhibitor, Nodal inhibitor, or GDF signaling pathway inhibitor. Exemplary activin inhibitors include SB431542, Follistatin, A8301, DMH1, Dorsomorphin, K02288, and SB505124. In certain cases, inhibitors of Nodal, such as, SB431542, Lefty, or Cerebrus may be used. In certain cases, SB431542, D4476, GW788388, LY364947, RepSox, SB525334, SD208 may be used to inhibit GDF signaling pathway.

In certain embodiments, two or more SMAD inhibitors may be included in the cell culture medium used in the methods described herein.

Activators of Sonic Hedgehog Signaling

In certain embodiments of the methods and compositions described herein, an activator of sonic hedgehog signaling may be present in the medium for culturing cells. The activator of sonic hedgehog signaling may be present at a concentration of at least about 0.01 µM, at least about 0.03 µM, at least about 0.1 µM, at least about 0.2 µM, at least about 0.25 µM, at least about 0.3 µM, at least about 1 µM, at least about 1.3 µM, at least about 1.5 µM, at least about 2 µM, at least about 2.2 µM, at least about 2.5 µM, at least about 2.8 µM, at least about 3 µM, at least about 3.5 µM, at least about 4 µM, at least about 4.5 µM, at least about 5 µM, at least about 10 µM, at least about 20 µM, at least about 30 µM, at least about 40 µM or at least about 50 µM, such as, 0.05 µM-5 µM, 0.01 µM-2.5 µM, 0.05 µM-2 µM, or 0.1 µM-2 µM.

In certain cases, the activator of sonic hedgehog signaling may be shh or a derivative thereof. In certain cases, the activator of sonic hedgehog signaling may be a small molecule, such as, purmorphamine, SAG smoothened agonist, Hh-Ag1.5, or derivatives and analogs thereof.

Wnt Inhibitor

In certain embodiments of the methods and compositions described herein, an inhibitor of Wnt signaling may be present in the medium for culturing cells.

Wnt inhibitors are agents that downregulate expression or activity of wnt. Agents of interest may interact directly with wnt, e.g. drugs, i.e., small molecules, blocking antibodies, etc., or may interact with wnt associated proteins, e.g. Wnt co-receptors LRP5/6 and the transmembrane protein Kremen. A number of wnt inhibitors have been described and are known in the art.

Wnt inhibitors of interest interfere with the interaction between soluble, extracellular Wnt proteins, and the frizzled receptors that are present on the surface of normal cells. Such agents include, without limitation, soluble frizzled polypeptides comprising the wnt binding domains; soluble frizzled related polypeptides; wnt specific antibodies; frizzled specific antibodies; and other molecules capable of blocking extracellular wnt signaling.

Among the known wnt inhibitors are members of the Dickkopf (Dkk) gene family (see Krupnik et al. (1999) Gene 238(2):301-13). Members of the human Dkk gene family include Dkk-1, Dkk-2, Dkk-3, and Dkk-4, and the Dkk-3 related protein Soggy (Sgy).

Other inhibitors of wnt include Wise (Itasaki et al. (2003) Development 130(18):4295-30), which is a secreted protein. The Wise protein physically interacts with the Wnt co-receptor, lipoprotein receptor-related protein 6 (LRP6), and is able to compete with Wnt8 for binding to LRP6.

Inhibitors may also include derivatives, variants, and biologically active fragments of native inhibitors.

In certain cases, the Wnt inhibitor may be a small molecule such as, CKI-7, IWP analogs, IWR analogs, XAV939, 53AH, Wnt-C59.

In certain cases, the Wnt inhibitor may be present in the culture medium at a concentration of 10 ng/ml, 200 ng/ml, 300 ng/ml, 400 ng/ml, 500 ng/ml, 1 µg/ml, 1.5 µg/ml, 2 µg/ml, 2.5 µg/ml, or 5 µg/ml for example, at a concentration of 500 ng/ml-3 µg/ml, e.g., 1 µg/ml-3 µg/ml.

Assessing Generation of Cell Populations

In certain cases, the cell populations cultured according to the methods disclosed herein may be monitored to assess changes in the cells imparted by culturing (e.g., during one or more time points in the culture method disclosed herein) so as to characterize the cell population produced. in certain embodiments, the production of MGE precursor cells (mitotic MGE precursor cells and/or post-mitotic interneurons) may be assessed by determining the expression of markers characteristic of these cell populations.

In certain cases, the expression of certain markers is determined by detecting the presence or absence of the marker transcript or protein expression. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest. In certain processes, the expression of marker genes characteristic of the cell population of interest as well as the lack of significant expression of marker genes characteristic of PS cells and other cell types may be determined.

Monitoring of generation of MGE precursor cells may be by determining expression of NKX2.1 gene. As such, the MGE precursor cells produced by the processes described herein express the NKX2.1 marker gene, thereby producing the NKX2.1 gene product. The MGE precursor cells produced by the methods described herein also express the FOXG1, and may express LHX6, LHX7/8, OLIG2, ASCL1, and DLX2. Furthermore, the MGE precursor cells produced by the methods described herein do not express PAX6.

In some embodiments described herein, the expression of the NKX2.1 marker and/or the FOXG1 marker in MGE precursor cells is at least about 2-fold higher to at least about 10,000-fold higher than the expression of the NKX2.1 marker and/or the FOXG1 marker in non-MGE precursor cells, for example pluripotent stem cells. In other embodiments, the expression of the NKX2.1 marker and/or the FOXG1 marker in MGE precursor cells is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of the NKX2.1 marker and/or the FOXG1 marker in non-MGE precursor cells, for example pluripotent stem cells.

In certain cases, the monitoring of generation of MGE precursor cells (mitotic MGE precursor cells and/or post-mitotic interneurons) may be carried out by performing functional analysis of the cells of interest. For example, MGE precursor cells generated by the methods described herein may be may generate interneurons in vivo or in vitro. In certain cases, MGE precursor cells produced by the methods disclosed herein may generate interneurons that differentiate into inhibitory GABAergic interneurons that can migrate and functionally integrate with neuron in vivo.

In certain cases, the method does not include monitoring of generation of MGE precursor cells.

Enrichment, Isolation and/or Purification of Cell Populations

Cell populations of interest, such as, MGE precursor cells (mitotic MGE precursor cells and/or post-mitotic interneurons) produced by any of the above-described processes can be enriched, isolated and/or purified by using an affinity tag that is specific for such cells. Examples of affinity tags specific for a cell or cell population of interest include antibodies, ligands or other binding agents that are specific to a marker molecule, such as a polypeptide, that is present on the cell surface of the cells of interest but which is not substantially present on other cell types that may be found in a cell culture produced by the methods described herein.

Methods for making antibodies and using them for cell isolation are known in the art and such methods can be implemented for use with the antibodies and cells described herein. In one process, an antibody which binds to a marker expressed by cell population of interest is attached to a magnetic bead and then allowed to bind to the cells of interest in a cell culture which has been enzymatically treated to reduce intercellular and substrate adhesion. The cell/antibody/bead complexes are then exposed to a magnetic field which is used to separate bead-bound definitive endoderm cells from unbound cells. Once the cells of interest are physically separated from other cells in culture, the antibody binding is disrupted and the cells are replated in appropriate tissue culture medium.

Additional methods for obtaining enriched, isolated, or purified cell populations of interest can also be used. For example, in some embodiments, an antibody for a marker expressed by the cells of interest is incubated cell culture containing the cells of interest that has been treated to reduce intercellular and substrate adhesion. The cells are then washed, centrifuged and resuspended. The cell suspension is then incubated with a secondary antibody, such as an FITC-conjugated antibody that is capable of binding to the primary antibody. The cells are then washed, centrifuged and resuspended in buffer. The cell suspension is then analyzed and sorted using a fluorescence activated cell sorter (FACS). Antibody-bound cells are collected separately from cells not bound to the marker specific antibody, thereby resulting in the isolation of cells of interest. If desired, the isolated cell compositions can be further purified by using an alternate affinity-based method or by additional rounds of sorting using the same or different markers that are specific for the cells of interest. In certain cases, the MGE precursor cells may be enriched by sorting the cells based on size.

In certain cases, cells of interest, such as, MGE precursor cells are enriched, isolated and/or purified from other types of cells after the PS cell cultures are induced to differentiate towards the MGE precursor cell lineage. It will be appreciated that the above-described enrichment, isolation and purification procedures can be used with such cultures at any stage of differentiation.

In addition to the above-described procedures, cells of interest, such as, MGE precursor cells may also be isolated by other techniques for cell isolation. Additionally, cells of interest, such as MGE precursor cells, may also be enriched or isolated by methods of serial subculture in growth conditions which promote the selective survival or selective expansion of the cells of interest.

Using the methods described herein, cell populations or cell cultures enriched in cells of interest, such as, MGE precursor cells, by at least about 2- to about 1000-fold as compared to un-enriched cell populations are produced. In some embodiments, MGE precursor cells can be enriched by at least about 5- to about 500-fold as compared to untreated cell populations or cell cultures. In other embodiments, MICE precursor cells can be enriched from at least about 10- to about 200-fold, at least about 20- to about 100-fold, at least about 40- to about 80-fold, or at least about 2- to about 20-fold as compared to undifferentiated cell populations or cell cultures.

Genotypic Features of Cell Populations of the Present Disclosure

When derived from an isolated PS cell, or an established line of PS cells, the cell populations of this disclosure can be characterized as being the progeny of the originating cell or cell line. Accordingly, the cell populations will have the same genome as the cells from which they are derived. This means that over and above any karyotype changes, the chromosomal DNA will be over 90% identical between the PS cells and the cell populations generated therefrom. Cell populations of the present disclosure that have been treated by recombinant methods to introduce a transgene or knock out an endogenous gene are still considered to have the same genome as the line from which they are derived, since all non-manipulated genetic elements are preserved. Cell populations of the present disclosure and PS cells can be identified as having the same genome by standard genetic techniques. Possession of the same genome can also be inferred if the cell populations are obtained from the undifferentiated line through the course of normal mitotic division.

In certain industrial applications, this characteristic is a valuable feature of the cell populations of the present disclosure. In particular, the availability of the originating PS cells provides a further supply of genetically matched differentiated cell populations, since the PS cells can be caused to proliferate and differentiated into more cell populations of the present disclosure as required. Furthermore, the PS cells can be differentiated into other therapeutically important lineages.

The techniques described in this application allow for the production of large cell populations that share the same genome, by expanding the cells before or after differentiation. Populations of $10^8$, $10^{10}$, or $10^{12}$ cells are theoretically possible. Such large populations are usually divided into separate containers suitable for further culture, drug screening, or therapeutic administration.

Certain embodiments of the disclosure include originating cells (such as an undifferentiated PS cell line, or an intermediate population, in combination with one or more populations of differentiated cells bearing characteristics of MGE precursor cells. The populations may either be in the same container, in separate containers in the same facility, or in two different locations. The undifferentiated and differentiated cells may be present simultaneously or at a different time, such as when a culture of undifferentiated cells is caused to differentiate into MGE precursor cells, as described herein.

Compositions Comprising Cell Populations of the Present Disclosure

Cell compositions produced by the above-described methods include cell cultures that contain isolated MGE precursor cells and cell populations enriched in isolated MGE precursor cells.

In some embodiments, cell compositions which include cells of the present disclosure, wherein at least about 50%-80% of the cells in culture are the cells of interest, can be produced. The differentiation methods described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to cells of interest.

In embodiments, in which isolation of cells of interest is employed, for example, by using an affinity reagent that binds to the cells of interest, a substantially pure cell population of interest can be recovered.

Some embodiments described herein relate to cell compositions comprising from at least about 5% cells of interest to at least about 95% cells of interest. In some embodiments, the cell cultures or cell populations comprise mammalian cells. In preferred embodiments, the cell cultures or cell populations comprise human cells. For example, certain specific embodiments relate to cell compositions comprising human cells, wherein from at least about 5% to at least about 95% of the human cells are MGE precursor cells. Other embodiments relate to cell compositions comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the human cells are MGE precursor cells.

In a specific embodiment, a composition comprising human cells, where at least 70% of the human cells are human MGE precursor cells is provided.

In another embodiment, a composition comprising human cells, where at least 80% of the human cells are human MGE precursor cells is provided.

In certain embodiments, the composition may include pluripotent stem cells and/or inhibitory interneurons.

Cell populations of the present disclosure, such as, sEB comprising MGE precursor cells, aEB comprising MGE precursor cells, MGE precursor cells, or neurons generated from MGE precursor cells may be present in a composition comprising one or more of these cell populations.

The cells populations of the present disclosure may be used fresh or stored in art accepted methods, such as, cryopreserved for a period of 1 day to 10 years before being thawed and used.

Cell compositions produced by the above-described methods and compositions thereof may be assessed by using the markers and methods described herein as well as those known in the art.

Cell compositions produced by the above-described methods and compositions thereof may be enriched, isolated or purified using methods described herein as well as those known in the art.

Uses of Populations of the Present Disclosure

Cell Populations for Screening

The cells of the present disclosure can be used to screen for agents (such as, small molecules, peptides, polynucleotides) or environmental conditions (such as, culture conditions or manipulation) that affect the characteristics of MGE precursor cells and/or cells generated therefrom, such as, interneurons.

In one example, MGE precursor cells are used to screen factors that promote maturation into interneurons, or promote proliferation and maintenance of MGE precursor cells in tong-term culture. For example, candidate differentiation factors or growth factors are tested by adding them to cells in different wells, and then determining any phenotypic change that results, according to desirable criteria for further culture and use of the cells. This can lead to improved derivation and culture methods for generating and/or maintaining MGE precursor cells and/or cells generated therefrom.

Other screening methods of the present disclosure relate to the testing of pharmaceutical compounds for a potential adverse effect on MGE precursor cells and/or cells generated therefrom. This type of screening is appropriate not only when the compound is designed to have a pharmacological effect on MGE precursor cells themselves, but also to test for MGE precursor cells-related side-effects of compounds designed for a primary pharmacological effect elsewhere.

Other screening methods relate to the use of MGE precursor cells to measure the effect of small molecule drugs that have the potential to affect MGE precursor cells. To this end, the cells can be combined with test compounds in vitro, and the effect of the compound on MGE precursor cells is determined.

General principles of drug screening are described in U.S. Pat. No. 5,030,015, and in the textbook In vitro Methods in Pharmaceutical Research, Academic Press 1997. Assessment of the activity of candidate pharmaceutical compounds generally involves combining the differentiated cells of this invention with the candidate compound, either alone or in combination with other drugs. The investigator determines any change in the morphology, marker, or functional activity of the cells that is attributable to the compound (compared with untreated cells or cells treated with a negative control compound), and then correlates the effect of the compound with the observed change.

MGE Precursor Cells in Clinical Therapy

Cell populations comprising MGE precursor cells, such as, cell populations enriched in MGE precursor cells, as well as, purified MGE precursor cells produced by the methods described herein may be used in a number of clinical applications.

In certain embodiments, the MGE precursor cells produced using the methods provided herein may be used for treating a subject in need for treatment with MGE precursor cells.

In certain cases, a subject in need for treatment with MGE precursor cells may be a patient having or at risk of developing a neurological disorder characterized by decreased inhibitory interneuron activity. In certain cases, the patient may have reduced inhibitory neuron function and/or elevated excitatory neuron function.

In certain cases, the MGE precursor cells may be transplanted into a target site in the subject that provides appropriate differentiation conditions for the MGE precursor cells to differentiate into interneurons, such as, GABAergic inhibitory interneurons. Cells may be transplanted by any of a number of standard methods in the art for delivering cells to tissue, e.g., injecting them as a suspension in a carrier, such as, a suitable solution or a solid or semi-solid support. Suitable solutions include saline, PBS, L15, DMEM, Iscove's media, etc. Suitable solid supports include beads, a filter such as a mesh filter, a membrane, etc.

In certain cases, the MGE precursor cells may be administered to the nervous system of the subject. In certain cases, the administering may be performed by transplanting the MGE precursor cells into one or more locations in the nervous system of the subject.

In certain embodiments, the MGE precursor cells may be administered into one or more locations in the nervous system of the subject, such as, central nervous system, such as, brain, e.g., cerebellum, cerebral cortex, hippocampus, striatum (e.g., basal ganglia), thalamus, hypothalamus, subthalamic nucleus; and spinal cord.

In certain embodiments, the administering of MGE precursor cells may result in the inhibitory neuron function being restored. In certain cases, the administering may include transplanting the MGE precursor cells in a first portion of the brain of the subject and restoring inhibitory neuron function in a second portion of the brain, distal from the first.

In certain embodiments, the MGE precursor cells may be administered to a subject having or at risk of developing a neurological disorder, such as, seizure disorder, e.g., epilepsy, Huntington's disease, Parkinson's disease, ALS, schizophrenia, Alzheimer's disease, autism, dyskinesia, chronic pain, spasticity, neuropathic pain, multiple sclerosis, traumatic brain injury, diseases of dis-myelination, bi-polar disorder, depression, and cancer.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Materials and Methods:

Cell Culture and FACS-Sorting

HES-3 hESCs were maintained on irradiated mouse embryonic fibroblasts (Millipore) in knockout DMEM with 20% knockout serum replacement, 1% nonessential amino acids (NEAA), 1% pen-strep-glutamine, 0.0008% 2-mercaptoethanol, and 10 ng/mL FGF-basic (Invitrogen), Differentiation was initiated by CollagenaseIV/Dispase (1 mg/mL each; Invitrogen) preferential selection for hESC colonies. Colonies were trypsinized to single cells, and, as described (Eiraku, M., et al. (2008). Cell Stem Cell 3, 519-532), ~10,000 cells/well were plated into low-attachment round-bottom 96-well plates (Corning or NOF) to form one sEB/well in optimized B27+5F; differentiation medium #1, consisting of Neurobasal-A, 2% B27-vitamin A (Invitrogen), and the same supplements in hESC media but without FGF. Also, Y27632 (10 µM), SB3431542 (10 µM), Purmorphamine (1-2 µM) (Stemgent), BMPRIA-Fc (1.5 µg/mL), and DIKK1 (1 µg/mL) (Invitrogen) were added.

On ~d7, Y27632 was removed, and sEBs were plated adherent en-bloc onto matrigel (BD Biosciences) coated plates in medium #1. On ~d14, factors were removed from medium #1 except for Purmorphamine. On ~d25, aEBs were trypsinized and replated as dissociated monolayer onto matrigel or polyornithine/laminin coated plates. DAPT (10 µM) (Tocris) was added from ~d27-d30. After FACS sorting on day ~35, GFP+ cells could be replated (10-25,000 cells/cm2) onto cortical glial cells in medium #1. Glial cells were prepared from newborn mouse cortex, passaged at least 3× with serum to remove mouse neurons, and pre-treated at confluency with Ara-C (5 µM) (Sigma). Every 3-4 days, half of media was replaced with differentiation medium #2: Neurobasal-A, 2% B27+vitamin A, (Invitrogen) and same supplements in medium #1, without factors, except NEAA and Purmorphamine were removed, and BDNF (25 ng/mL) was added (R&D Systems). Media was replaced every 3-4 days.

FACS analysis and sorting was performed on FACS Aria II (BD Biosciences). Cells were gated for live cell DAN exclusion, small scatter size, single cells, NKX2.1-GFP signal, and PSA-NCAM-APC or -PE (Miltenyi Biotech) signal intensity. GFP-negative cells and isotype antibody (Santa Cruz) controls were used. Data was analyzed with Flowjo (Treestar) software. For live cell imaging, differentiation was similar to above, but 5,000 cells/well were plated into Aggrewell-800 plates (Stem Cell Technologies), and sEBs were plated en-bloc on day 4-7. Imaging was performed by time-lapse confocal microscopy with temperature (37° C.) and gas (5% O2, 5% CO2, 90% N2) controls (Leica SP5).

Second trimester human fetal cortex or MGE tissue was dissected, dissociated to single cells with Papain (Worthington Biochemical), plated onto matrigel coated plates (~100,000 cells/cm$^2$) in differentiation medium #2, and treated with Ara-C at confluence. MGE cells cultured for one week, or hESCs sorted on day 35, were replated onto cortical cultures (~10-20,000 cells/cm$^2$).

All experiments conducted on hESCs and human fetal tissue adhered to approved UCSF Stem Cell Research Oversight committee and Committee on Human Research protocols.

Transplantation and Graft Proliferation

Excess medium was removed from sorted cell pellets to create concentrated cell suspensions of 1000 cells/nl. Cells were loaded into a beveled glass micropipette (Wiretrol 5 ul, Drummond Scientific Company) mounted on a stereotactic hydraulic injector. P2 CB.17-SCID pups (Charles River) were anesthetized through hypothermia and positioned in a clay head mold on the injector platform. 10-100,000 cells per injection site were delivered transcranially into the right cerebral cortex using the following coordinates: 0.9 mm from the midline (sagittal sinus), and 2.6 mm from lambda. The depth of injection was 0.45 mm from the skin surface. All transplantation experiments adhered to approved UCSF Institutional Animal Care and Use Committee protocols.

Initially, day 35 monolayer cultures were sorted for NKX2.1-GFP+, without PSANCAM selection, and injected into newborn SCID mouse cortex. However, within 4 months, injected mouse brains (12/12 mice) contained tumor-like overgrowths at the injection site and/or at the pial surface near the injection tract (data not shown). These were not pluripotent cell-derived teratomas; OCT4+ cells or polarized neuroepithelial rosettes were not found. The growths primarily contained NKX2.1-GFP+ neural cells, Tumors were defined as a core of human-specific nuclear antigen (HNA) positive and KI67+ human cells persisting for more than 4 months post-injection (MPI). tumor incidence was a surprise because day 35 cultures contained seemingly few neural progenitor cells expressing KI67, GFAP, or OLIG2 (FIG. 3E). But, focal growths (~1 focus/2500 plated cells, n=3) were occasionally detected in extended co-cultures, consistent with tumor formation in vivo. Therefore, we performed protocol optimization to impede these growths. Low-density monolayer culture promoted neuronal differentiation and lowered tumor incidence to 50% (6/12 mice). Tumor incidence was further reduced to 33% (3/9 mice) by brief addition of DAPT, a gamma secretase inhibitor of Notch signaling, to induce neuronal differentiation prior to injection. In vitro focal growths (n=3) and in vivo tumor incidence were eliminated (0/6 mice) when day 35 cultures were pretreated with DAPT and FACS-sorted for both NKX2.1-GFP+ and PSA-NCAM+ cells prior to co-culture or transplantation, whereas GFP+ and PSA-NCAM-negative cells continued to form foci and tumors (3/4 mice). A summary of injected animals is provided (FIG. 16).

Immunostaining

Cultured cells were fixed in 4% paraformaldehyde for 10-20 min. Mouse brains were fixed overnight-4° C. after trans-cardial perfusion and sectioned (50 μm) by vibratome or sliding microtome. EBs and human tissue were sectioned (25 μm) by cryostat. Cells and sections were stained: 5-10 min antigen retrieval with boiling 0.01M citrate buffer pH=6, 1 hr block with 5% serum and 0.1% triton X100 in PBS, overnight-4° C. primary antibody in block buffer (except triton-free buffer used for GABA antibody), wash 3× in PBS+tritonX100, 2 hr secondary antibody (Invitrogen), wash 4× in PBS+tritoriX100. Primary antibodies are listed in Table 2.

TABLE 2

| Antibodies | | | |
|---|---|---|---|
| Antibody | Company | Catalog# | Dilution |
| ASCL1 | Cosmo Bio | SK-T01-003 | 1-500 |
| CALB | Swant | CB38 | 1-2000 |
| CALR | Swant | 7699 | 1-2000 |
| CHAT | Millipore | AB144P | 1-300 |
| COUPTFII | Perseus Proteomics | PP-H7147-00 | 1-1000 |
| DARPP32 | Santa Cruz | sc-11365 | 1-1000 |

TABLE 2-continued

| Antibodies | | | |
|---|---|---|---|
| Antibody | Company | Catalog# | Dilution |
| DCX | Cell Signaling | 4604S | 1-500 |
| DLX2 | Gift from K. Yoshikawa | | 1-1000 |
| ER81 | Covance | PRB-362C | 1-1000 |
| FOXG1 | Gift from Y. Sasai | | 1-500 |
| GABA | Sigma | A2052 | 1-2000 |
| GFAP | Millipore | MAB3402 | 1-500 |
| GFP | Aves Labs | GFP-1020 | 1-1000 |
| HNA | Millipore | MAB1281 | 1-500 |
| ISLET1 | DSHB | 39.4D5 | 1-200 |
| KI67 | Abcam | ab15580 | 1-500 |
| NCadherin | BD Biosciences | 561554 | 1-50 |
| NEUN | Millipore | MAB377 | 1-150 |
| NEUN | Millipore | MAB377B | 1-150 |
| NKX2.1 | Novacastra | TTF-1-L-CE | 1-150 |
| NKX2.1 | Santa Cruz | sc-13040 | 1-250 |
| NKX2.2 | DSHB | 74.5A5 | 1-100 |
| OLIG2 | Millipore | AB9610 | 1-500 |
| PAX6 | Millipore | AB5409 | 1-250 |
| PV | Sigma | P3088 | 1-4000 |
| PV | Swant | PV-25 | 1-2000 |
| RAX | Gift from Y. Sasai | | 1-500 |
| RFP | Clontech | 632496 | 1-500 |
| RFP | Chromotek | 5f8 | 1-1000 |
| SST | Bachem | T-4103.0050 | 1-500 |
| TBR1 | Abcam | ab31940 | 1-500 |
| TH | Pelfreeze | P40101-0 | 1-1000 |
| TUJ1 | Covance | MMS-435P | 1-1000 |
| VGAT | Synaptic Systems | 131 003 | 1-500 |

Transcript Expression

RNA was prepared from cell pellets with RNEasy kit kit (Qiagen). CDNA was prepared with Superscript III-first strand kit (Invitrogen). Quantitative RTPCR was performed with SYBR green master mix on a real-time PCR system (Applied Biosystems). Reverse-transcriptase negative controls were used. Amplicon specificity was determined by gel-electrophoresis and melt-curve analysis. Primer sequences are listed in Table 3.

TABLE 3

| Primer Sequences | | |
|---|---|---|
| Gene | Strand | Primer Sequence |
| ASCL1 | F | GTCCTGTCGCCCACCATCTC |
| ASCL1 | R | CCCTCCCAACGCCACTGAC |
| CALB2 | F | TCAGAGATGTCCCGACTCCTG |
| CALB2 | R | GCCGCTTCTATCCTTGTCGTAA |
| DLX2 | F | GCCTCAACAACGTCCCTTACT |
| DLX2 | R | TCACTATCCGAATTTCAGGCTCA |
| FOXG1 | F | AGAAGAACGGCAAGTACGAGA |
| FOXG1 | R | TGTTGAGGGACAGATTGTGGC |
| GAD1 | F | CGAGGACTCTGGACAGTAGAGG |
| GAD1 | R | GATCTTGAGCCCCAGTTTTCTG |
| GAPDH | F | GGTGGTCTCCTCTGACTTCAAC |
| GAPDH | R | TTCGTTGTCATACCAGGAAATG |
| LHX6 | F | TCTGCAAGATGGAGTACTTCAGC |
| LHX6 | R | CTTGGGTTGACTGTCCTGTTC |

TABLE 3-continued

Primer Sequences

| Gene | Strand | Primer Sequence |
|---|---|---|
| NKX2.1 | F | AGACTCGCTCGCTCATTTGT |
| NKX2.1 | R | CTCCATGCCCACTTTCTTGT |
| NPY | F | CGCTGCGACACTACATCAAC |
| NPY | R | CAGGGTCTTCAAGCCGAGTT |
| OLIG2 | F | AGCTCCTCAAATCGCATCC |
| OLIG2 | R | ATAGTCGTCGCAGCTTTCG |
| POU5F1 | F | GCAAAACCCGGAGGAGGAGTC |
| POU5F1 | R | CCACATCGGCCTGTGTATATC |
| PVALB | F | AAAGAGTGCGGATGATGTGAAG |
| PVALB | R | ACCCCAATTTTGCCGTCCC |
| SST | F | GCTGCTGTCTGAACCCAAC |
| SST | R | CGTTCTCGGGGTGCCATAG |
| TUBB3 | F | GCAACTACGTGGGCGACT |
| TUBB3 | R | CGAGGCACGTACTTGTGAGA |

For microarray analysis, RNA was submitted to the Southern California Genotyping Consortium for hybridization to lumina Human HT-12 v4.0 expression bead-chip. hESC=one sample and three technical replicates. D20=three independent samples. D35=one sample and two technical replicates. D55=one sample and one technical replicate. Data was analyzed with GenomeStudio (Illumina) software. Probes without signal were validated by confirming hybridization to control human brain reference RNA and/or to samples archived in ArrayExpress.

Electrophysiology and Optical Methods

The patch electrodes were made from borosilicate glass capillaries (B-120-69-15, Sutter Instruments) with a resistance in the range of 5-7 MΩ. The pipettes were tip-filled with internal solution containing (in mM): 125 K-gluconate, 15 KCl, 10 HEPES, 4 $MgCl_2$, 4 $Na_2ATP$, 0.3 $Na_3GTP$, 10 Tris-phosphocreatine, 0.2 EGTA.

For cultured neurons, the bath was constantly perfused with fresh recording medium containing (in mM): 145 NaCl, 3 KCl, 3 CaCl2, 2 MgCl2, 10 HEPES, 8 glucose. Transverse slices (300 μm) were cut on a tissue chopper (Leica VT1200S) and maintained in an incubation chamber with aCST containing (in mM): 110 Choline Cl, 2.5 KCl, 0.5 CaCl2, 7 MgCl2, 1.3 NaH2PO4, 25 NaHCO3, 10 glucose. Slice recording medium contained (in mM): 125 NaCl, 2.5 KCl, 2 CaCl2, 1.3 MgCl2, 1.3 NaH2PO4, 25 NaHCO3, 10 glucose. Recordings were made with an Axon 700B patch-clamp amplifier and 1320A interface (Axon Instruments). Signals were filtered at 2 kHz using amplifier circuitry, sampled at 10 kHz, and analyzed using Clampex 10.2 (Axon Instruments).

Photostimulation was delivered by mercury lamp (75 mW) with a GFP excitation bandpass filter and light pulses were generated by Maste-8 (A.M.P.I.) through a high-speed shutter (UNIBLITZ), the power density of the blue light (Boyden, E. S., et al. (2005). Nat Neurosci 8, 1263-1268) (Nagel, G., et al. (2003). Proc Natl Acad Sci USA 100, 13940-13945) was 8-12 mW·mm−2, measured with a power meter (Coherent Instruments).

Statistical Analyses

Data are presented as mean±s.e.m, FIG. 3E data are represented as mean % of co-expressing/GFP+ cells. FIGS. 4C-H data as mean bead signal intensity. FIG. 5C data as mean % of UbC-RFP+, ChR2-YFP+, or TUJ+ neurons. FIGS. 7D-E data as mean % of HNA+ or UbC-RFP+ human cells. Statistical comparisons used one-way ANOVA with post hoc Bonferroni test for electrophysiology data, and used a twotailed, two-sample unequal variance Student's t-Test for immunostaining data. Cell counts were calculated with Imaris (Bitplane) software using MATLAB plugin. A summary of sample sizes and cell counts for each experiment and marker are listed in Table 4.

TABLE 4

Summary of sample sizes and cell counts for each figure, marker, and stage of differentiation.

| Figure | Marker | Stage | Number of Differentiation Experiments/ Animals | Positive Cells | Total Cells Counted |
|---|---|---|---|---|---|
| 3E | NKX2.1 | 5 wk | 6 | 1103 | 1219 |
| 3E | FOXG1 | 5 wk | 6 | 946 | 1320 |
| 3E | NKX2.2 | 5 wk | 5 | 138 | 1213 |
| 3E | PAX6 | 5 wk | 2 | 0 | 808 |
| 3E | ASCL1 | 5 wk | 2 | 476 | 622 |
| 3E | COUPTFII | 5 wk | 2 | 7 | 848 |
| 3E | OLIG2 | 5 wk | 2 | 21 | 331 |
| 3E | GFAP | 5 wk | 3 | 58 | 786 |
| 3E | KI67 | 5 wk | 3 | 33 | 1044 |
| 3E | TUJ | 5 wk | 9 | 1777 | 2204 |
| 3E | GABA | 5 wk | 7 | 955 | 1292 |
| 3E | DLX2 | 5 wk | 2 | 391 | 472 |
| 3E | DARPP32 | 5 wk | 2 | 0 | 848 |
| 3E | ER81 | 5 wk | 2 | 4 | 954 |
| 3E | ISLET1 | 5 wk | 4 | 139 | 1467 |
| 3E | CHAT | 5 wk | 3 | 2 | 2082 |
| 3E | TH | 5 wk | 3 | 64 | 2082 |
| 3E | TBR1 | 5 wk | 3 | 5 | 1691 |
| 5C | GFP | 5 wk | 5 | 314 | 342 |
| 5C | GFP | 10 wk | 3 | 333 | 376 |
| 5C | GFP | 20 wk | 3 | 416 | 517 |
| 5C | GFP | 30 wk | 3 | 132 | 211 |
| 5C | GABA | 5 wk | Same as 3E - 5 wk | | |
| 5C | GABA | 10 wk | 4 | 801 | 1113 |
| 5C | GABA | 20 wk | 1 | 38 | 56 |
| 5C | GABA | 30 wk | 2 | 140 | 162 |
| 5C | VGAT | 5 wk | 6 | 553 | 1424 |
| 5C | VGAT | 10 wk | 2 | 162 | 211 |
| 5C | VGAT | 20 wk | 3 | 127 | 169 |
| 5C | VGAT | 30 wk | 1 | 16 | 21 |
| 5C | CALB | 5 wk | 5 | 488 | 1639 |

Development of the B27+5F Method

We compared three published protocols (methods #1, #2, and #3) for their ability to induce NKX2.1+ MGE precursor cells from hESCs. The first method (#1) reported hESC-derived NKX2.1+ and FOXG1+ MGE precursor cells at ~13% efficiency (Watanabe, K., et al. (2007). Nat Biotechnol 25, 681-686). This 35-day protocol utilized serum-free (knockout serum replacement (KSR)-early/B27-late) supplemented medias and dual-SMAD inhibition of BMP (via BMPRIA-Fc) and activin/nodal (via SB431542) signaling pathways to direct neural ectoderm-like differentiation, along with WNT pathway inhibition (via DKK1) to specify anterior forebrain-like identity of embryoid bodies (EBs). From day 24-35, inhibitors were removed, and sonic hedgehog (SHH) was added to specify ventroanterior forebrain-like cells. The second method (#2) reported NKX2.1+ and FOXG1+ MGE precursor cells at ~84% efficiency after 28 days in serum-free (KSR/N2) supplemented medias (Li, X.

J., et al. (2009). Development 136, 4055-4063). Dual-SMAD inhibition was not used, but SHH treatment, with or without simultaneous WNT inhibition, was initiated earlier during differentiation (day 10-28). Although these protocols were reported to generate FOXG1+ and NKX2.1+ cells, ventral telencephalic MGE-like versus POA/septum-like identity was not investigated.

In our hands, method #1 (FIG. 8B), method #2 (not shown), and an optimized version of method #1 (FIG. 9A) were unable to generate NKX2.1-GFP+ MGE precursor-like cells. The same was true when SHH was used instead of purmorphamine. However, we found that a hybrid method could generate NKX2.1-GFP+ MGE precursor-like cells at 12% efficiency as quantified by fluorescence activated cell sorting (FACS) (FIG. 8C). This 25-day hybrid method involved dual-SMAD (via SB431542 and BMPRIA-Fc) and WNT (via DKK1) inhibition throughout the protocol and simultaneous Smoothened agonist, purmorphamine, treatment from day 10-25 in serum-free (KSR/B27) supplemented medias. A similar efficiency was achieved in B27/B27 supplemented media (not shown). We assumed that GFP+ cell induction resulted from early (d10) SHH pathway activation, in contrast to late (d24) SHH from method #1, and we hypothesized that even earlier addition of purmorphamine (from day 0-25) would increase the percentage of NKX2.1+ MGE precursor cells. However, this modification resulted in decreased (1.9%) efficiency in KSR/B27 media (FIG. 8D).

However, replacing KSR with B27 supplemented media throughout the 25-day protocol, along with early addition of five factors [Rho-associated protein kinase (ROCK) inhibitor (Y27632), dual-SMAD inhibitors (SB431542 and BMPRIA-Fc), WNT inhibitor (DKK1), and Smoothened agonist (purmorphamine), surprisingly resulted in most cells (70.2%) becoming NKX2.1-GFP+ MGE precursor cells (FIG. 8E). Furthermore, when the inhibitors were removed after two weeks of differentiation, and the protocol extended to day 35, we achieved NKX2.1-GFP+ differentiation efficiencies up to 90.8% by FACS analysis (FIG. 8F). Thus, early activation of the SHH pathway in combination with B27, or lack of KSR, media (B27+5F method) directed efficient ventral forebrain-like differentiation from hESCs.

During this study, a third method (method #3) reported to direct hypothalamic forebrain-like differentiation from HES-3 NKX2.1GFP/w hESCs at 12-14% efficiency in the presence of FGF2 and retinoic acid (Goulburn, A. L. et al. (2011). Stem Cells 29, 462-473). SHH was not used, but the media appeared to induce SHH, and WNT inhibitor, expression in their cultures and promoted a ventro-anterior neural fate despite use of retinoic acid, which can act as a caudalizing agent. After 50 days, some cells expressed FOXG1, but the efficiency and fates of these cells were not determined. In our hands, method #3 generated Nkx2.1-GFP+ cells at ~7% efficiency. In line with hypothalamic-like identity, method #3 generated less NKX2.1+ expression and more NKX2,2+ cells on day 24 compared to the B27+5F method (data not shown).

SHH pathway activation was required for NKX2,1-GFP+ cell derivation. In this study, we used 1-2 µM of purmorphamine or 500 ng/mL of SHH. Although 2-6 µM of purmorphamine slightly increased GFP+ differentiation efficiency in EB cultures, these higher concentrations decreased the viability of later-stage monolayer cultures (not shown). We also investigated whether WNT inhibition was dispensable for hESC-telencephalic-like identity, as suggested previously (Li, X. J., et al. (2009). Development 136, 4055-4063). While GFP+ cell differentiation efficiency was similar, DKK1 WNT inhibitor absence resulted in a decrease in the number of cells expressing telencephalic FOXG1 from 70% to 45% (not shown). In addition to WNTs, FGFs act as important rostra-caudal patterning factors during neural development (Borello, U., et al. (2008). Neural Dev 3, 17) (Mason, I. (2007). Nat Rev Neurosci 8, 583-596) (Ye, W., et al. (1998). Cell 93, 755-766), and FGF8 has been implicated in MGE telencephalic-like development from mouse ESCs (Danjo, T., et al. (2011), J Neurosci 31, 1919-1933), We did not add FGF8 to our cultures, but we did detect FGF8 transcript expression, in agreement with its role downstream of SHH (Gutin, G., et al. (2006), Development 133, 2937-2946) (OhKubo, Y., et al. (2002). Neuroscience 111, 1-17). Addition of an FGF inhibitor (PD173074) from the onset of differentiation (d0-25) caused a decrease in cells expressing FOXG1 (55%), but addition of the same inhibitor on day 14 (d14-25) had no effect on FOXG1 levels (not shown). Therefore, similar to fetal forebrain development, early inhibition of WNT and activation of FGF signaling pathways, along with SHH activation, play roles in patterning the ventral-telencephalic-like identity of hESC-derived cultures.

Cost-effective cell production methods will be preferred over lengthy protocols and expensive recombinant protein-based reagents, and cryopreservation of cells will facilitate future work. Here, we used 3 small molecules (Y27632, SB431542, and purmorphamine) and 2 recombinant proteins (BMPRIA-Fc and DKK1). Several small molecule substitutes now exist for inhibition of BMP and WNT pathways. We found that dorsomorphin (BMP pathway inhibitor) and CK1-7 (WNT pathway inhibitor) could replace the proteins in the B27+5F method (Kim, D. S., et al. (2010). Stem Cell Rev 6, 270-2810) (Osakada, F., et al. (2009). J Cell Sci 122, 3169-3179). Although cell viability was reduced by ~50%, NKX2.1-GFP+ efficiency was comparable (not shown). In addition, ~25% of hESC-derived MGE-like cells were viable after cryopreservation and thawing, and thawed cells matured into neurons with functional properties as confirmed by electrophysiology.

For clinical use, GMP-grade hPSC lines may be required. Accordingly, we examined cGMP-matched hESC. lines (ESI17, ESI35, ESI51, and ESI53 (Biotime)) for their ability to generate NKX2.1+ MGE-like cells. All of the lines were similar to HES-3 NKX2.1+ differentiation efficiency using the B27+5F method (see Example 8). Since the clinical grade lines do not have the NKX2.1 knock-in reporter, future work may be needed to determine acceptable impurity thresholds. Perhaps 75% purity of hESC-derived NKX2.1+ cells will be sufficient, particularly if the remaining impurities represent non-MGE-type GABAergic interneurons. Suggesting this possibility, we observed that most HES3 NKX2.1-GFP-negative neurons expressed GABA, and some expressed TH, but none expressed TBR1 or CHAT excitatory neuronal markers. To obtain a further purified composition of the NKX2.1+ MGE-like cells antibodies to MGE-specific cell markers, DNA plasmids, RNA, or virus to deliver transgenes (selectable marker, fluorescence, antibiotic resistance, gene overexpression/inhibition) that select for MGE cells or interneurons (Potter, G. B., et al. (2009). Mol Cell Neurosci 40, 167-186), or FACS-/magnetic MACS-based purification, or anti-mitotic compounds (such as AraC or MitoC) may be used.

Lentivirus Preparation

Self-inactivating lentiviral plasmids, FUGW-UbC-RFP (RFP dimer2) or pLenti-Synapsin-hChR2(H134R)-EYFP-WPRE (kind gift from Karl Deisseroth), were co-transfected with delta8.9 and VSVG plasmids into 293T cells (ATCC).

Lentiviral particle supernatants were collected, concentrated by ultracentrifugation, and used to transduce cells overnight with 8 μg/mL polybrene (Millipore).

Example 1 hESC-Derived Telencephalic MGE-Like Identity

To facilitate the identification of hPSC-derived NKX2.1+ MGE precursor cells, we used the HES-3 hESC line (HES-3 NKX2.1$^{GFP/w}$) with a GFP knock-in construct inserted into the second exon of NKX2.1 (Goulburn, A. L., et al. (2011). Stem Cells 29, 462-473). NKX2.1 expression marks ventral forebrain-specific identity in the developing nervous system, including telencephalic MGE, pre-optic area (POA), septum, and diencephalic hypothalamus. In combination with dual-SMAD (SB431542 and BMPRIA-Fc) and WNT inhibition (DKK1), we found that early SHH pathway activation (purmorphamine) and B-27 supplementation enabled highly efficient and reproducible ventral forebrain-like differentiation from hESCs. The average NKX2.1-GFP+ efficiency on day 20-30 post-differentiation was 74.9±2.1% (n=25 independent differentiation experiments). We also found that additional hPSC lines, research grade cGMP-matched ESI-17, 35, 51, and 53 (Biotime), and H9 (WiCell), hESC lines, and a human adult melanocyte-derived hiPSC line, differentiated into NKX2.1+ MGE precursor cells at a similar efficiency. The optimized B27+ five factor (B27+5F) method is outlined in FIG. 1A, FIG. 8. MGE precursor cells are also referred to as MGE-like progenitors.

Figure 9:
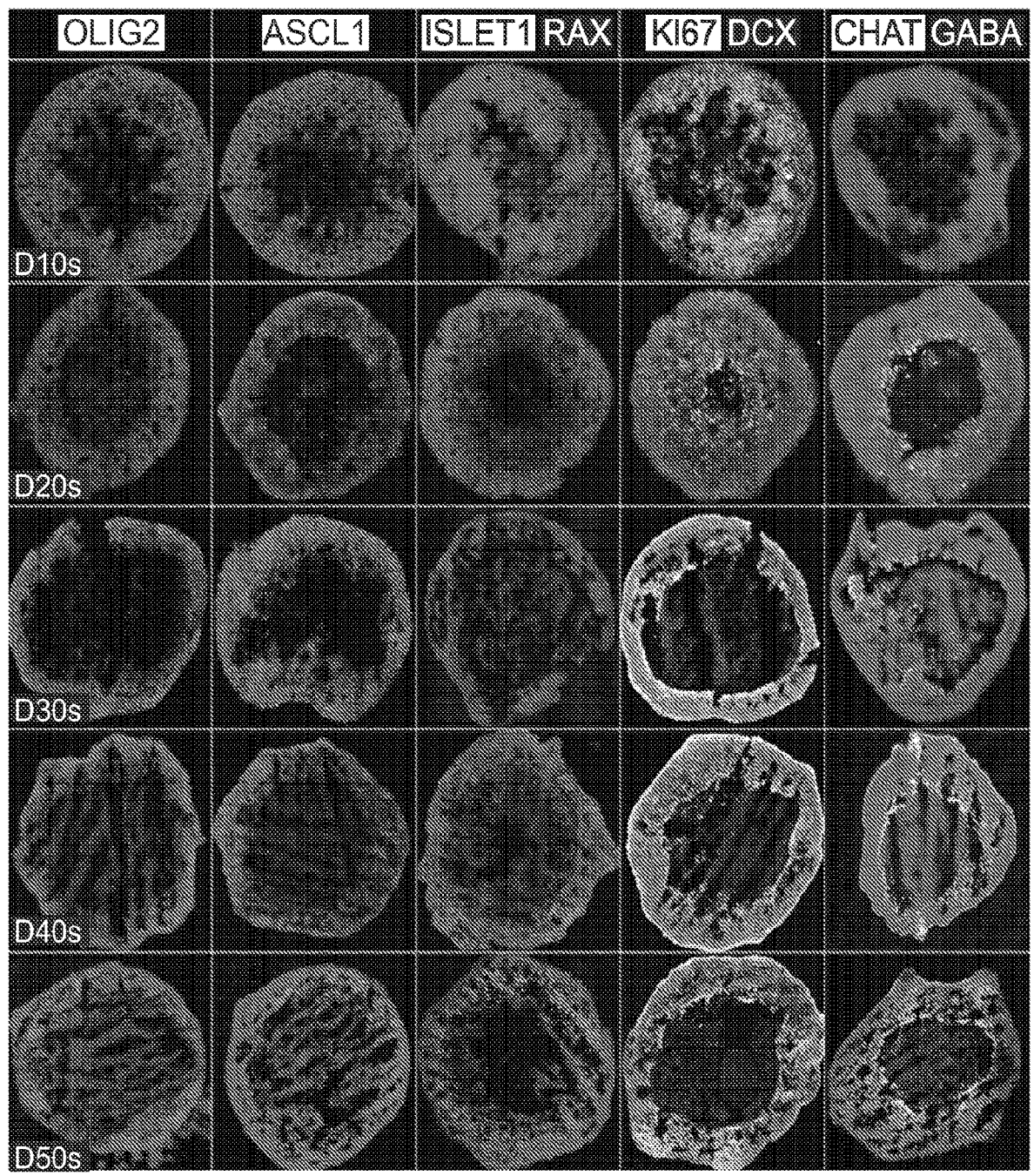
FIG. 9 illustrates hESC-derived cells have telencephalic MGE-like identity and GABAergic neuronal fate.

To determine the regional identity of the NKX2.1-GFP+ cells, we performed a 50-day time course of suspension embryoid body (sEB) differentiation and immunostaining analysis for markers of forebrain development (FIGS. 1B and 9). We detected robust NKX2.1-GFP expression by day 10 of differentiation that colocalized with NKX2.1 protein and was expressed throughout the time course. In contrast, PAX6, a marker of dorsal telencephalic neural progenitors, was not detected. Telencephalon marker, FOXG1, was found in most cells by day 20 and remained highly expressed. In opposition to this trend, NKX2.2 expression, a marker of hypothalamus and more ventrocaudal regions, was primarily only expressed between days 10-20. Additional ventral telencephalic progenitor markers, OLIG2 and ASCL1 (MASH1), were induced by day 20-30 (FIG. 9). ISLET1 is strongly expressed in lateral GE (LGE) and POA, and is expressed in scattered cells within the MGE; it was induced at later (d30-40) time points. By 30 days, the cells expressed the migratory neuronal marker, doublecortin (DCX), and the neurotransmitter, GABA. We did not detect the hypothalamic marker RAX or cholinergic neuron marker CHAT during the time course. Therefore, the hESCderived NKX2.1-GFP+ cells appeared to represent a telencephalic MGE-like progenitor and GABAergic neuronal lineage. A summary of marker expression during sEB culture is provided (FIG. 15).

FIG. 1. hESC-derived Telencephalic MGE like interneuron Precursor Cells (also called MGE precursor cells). (A) Outline of B27+5F method used to generate MGE precursor cells and GABAergic interneurons derived therefrom, and corresponding figures. Abbreviations: sEB=suspension embryoid body; aEB=adherent embryoid body; ML=monolayer; FACS=fluorescence activated cell sorting; Y27632=Rho-associated kinase (ROCK) inhibitor; SB431542=inhibitor of the TGFβ1 activin receptor-like kinases; BMPRIA=Bone Morphogenetic Protein Receptor 1a Fc chimera; DKK1=Dickkopf homolog 1; PM=Purmorphamine; BDNF=Brain-derived Neurotrophic Factor; DAFT=inhibitor of γ-secretase. See also FIG. 8. (B) Sections of sEBs and representative immunofluorescence analysis showing NKX2.1-GFP, PAX6, FOXG1, and NKX2.2 expression. Blue: DAPI. Scale Bar: 100 μm. See also FIG. 9 and FIG. 15.

Figure 8:
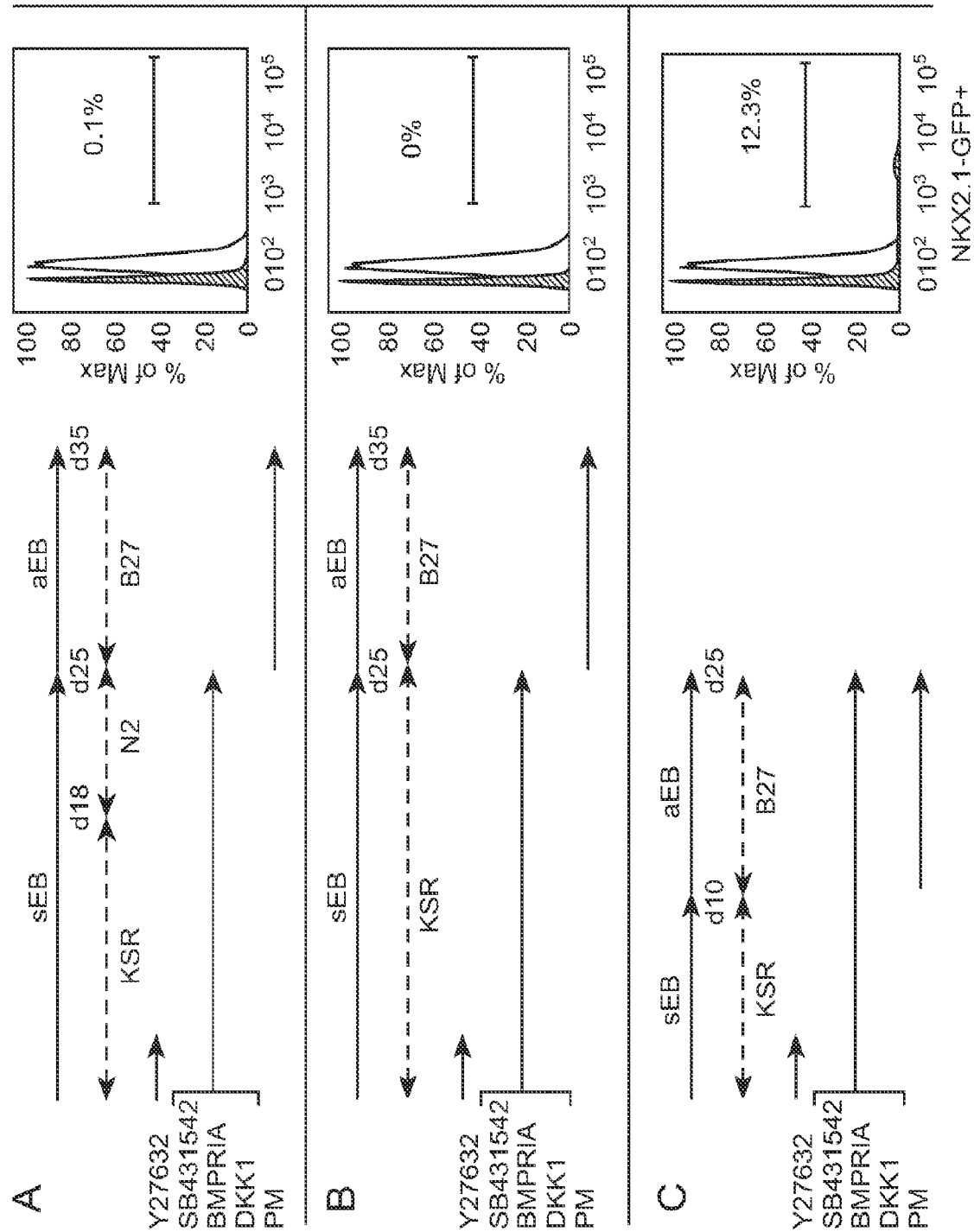
FIG. 8 (Panels A-F) provide a schematic of differentiation protocols and FACS analysis of differentiated hESCs.
Figure 8:
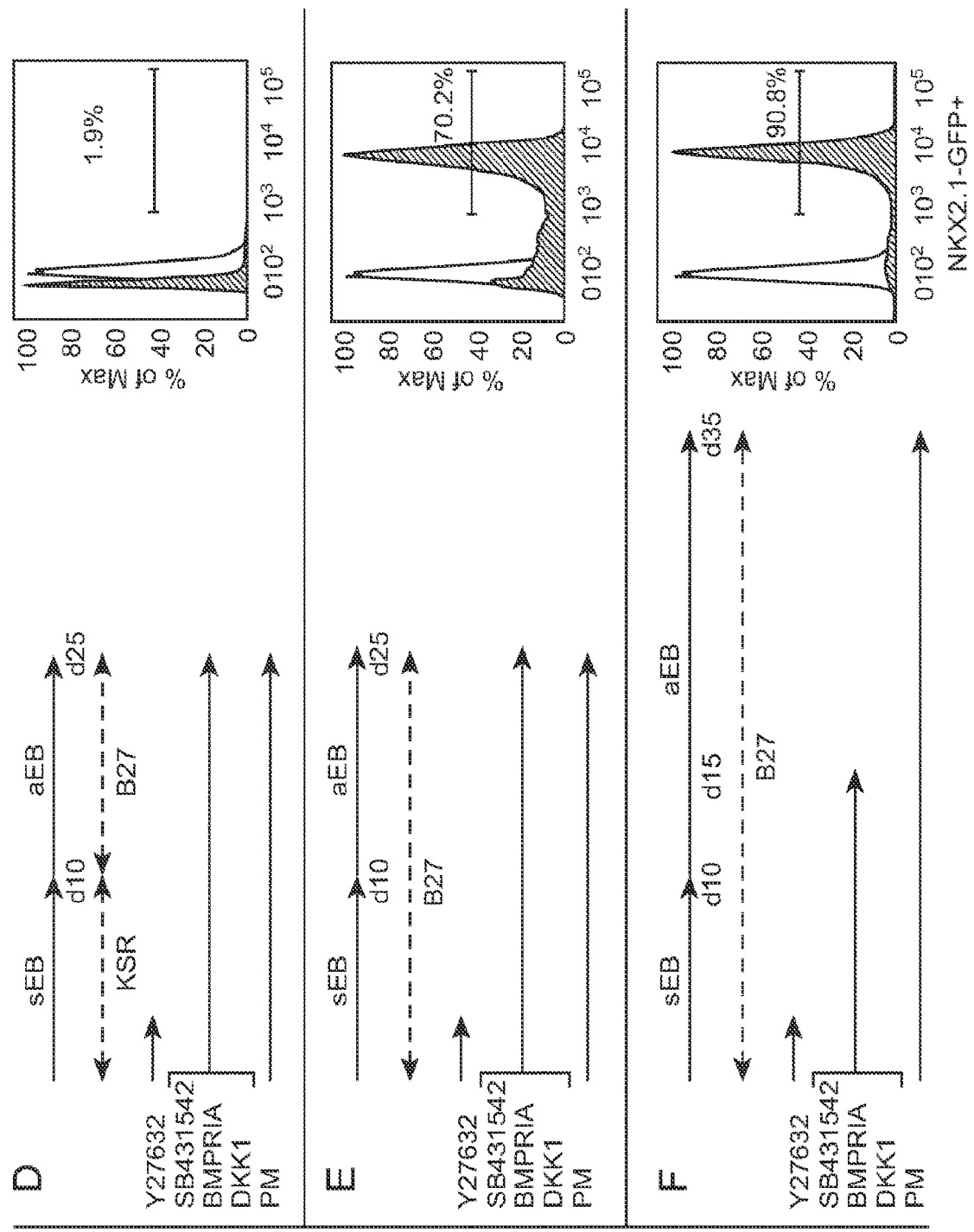

FIG. 8. FACS analysis of differentiated hESCs showing modifications to previously published protocols and the induction of NKX2.1-GFP+ cells by early SHH pathway activation combined with B27 media supplementation, related to FIG. 1. (A) Method #1a: KSR-N2-B27 supplemented media along with late (d25) PM. (B) Method #1b: KSR-B27 media with late (d25) PM treatment. (C) Method #½ hybrid: KSR-B27 media with mid (d10) PM treatment. (D) Similar to (C) but with early (d0) PM treatment. (E) Similar to (D) but with B27-B27 media to induce 70% GFP+ efficiency. (F) Similar to (E): B27-B27 media and early (d0) PM addition, but with inhibitor removal on d14 and PM treatment to d35 to induce up to 90% GFP+ efficiency. Tinted histograms=differentiated cultures. Empty histograms=undifferentiated culture controls.

FIG. 9. hESC-derived telencephalic MGE-like identity and GABAergic neuronal fate, related to FIG. 1 and FIG. 15. Additional immunostaining analysis of sEB sections showed induction of the ventral telencephalic markers OLIG2 and ASCL1 (early), ISLET1 (late), and mitotic marker KI67 (throughout). The migratory neuronal marker, DCX, and GABA were induced over time. In contrast, the hypothalamic marker, RAX, and the cholinergic neuronal marker, CHAT, were not detected after 50 days of differentiation. Blue=DAPI.

FIG. 15. A summary of marker expression during suspension embryoid body differentiation from hESCs, related to FIGS. 1 and 9.

Example 2: hESC-Derived MGE Precursor Cells Exhibited VZ and SVZ Radial Glial-Like Stem Cell Behaviors A defining feature of embryonic neural development is the acquisition of apico-basal polarity and development of radial glial neural stem cells (Kriegstein and Gotz, 2003). There is evidence that neuroepithelial progenitors in hESC-derived neural rosettes represent apico-basal-like polarity (Elkabetz, Y., et al (2008). Genes Dev 22, 152-165). When sEBs were plated en-bloc on day 4-7, the adherent EBs (aEBs) flattened and revealed the organization of NKX2.1-GFP+ cells in rosette structures (FIGS. 2A and 2B). N-cadherin expression was restricted to the rosette luminal surface, confirming polarity, and was consistent with localization to radial glial end feet on the apical ventricular surface in the embryonic brain. KI67 was expressed in many cells, particularly in those near the rosette lumen. In contrast, neuronal markers, ASCL1 and DCX, were detected away from the lumen (FIG. 2B).

Rosettes were labeled with RFP [UbiquitinC promoter-RFP (UbC-RFP) virus] and were monitored by live time-lapse imaging. We detected NKX2.1-GFP+ and UbC-RFP+ cells in rosette structures displaying ventricular zone (VZ) radial glia (vRG)-like interkinetic nuclear migration (INM) behavior prior to division (FIGS. 2C and 2E). VRG-like cell bodies translocated toward the rosette lumen and divided with a vertical cleavage plane (parallel to the fiber). Interestingly, daughter cells appeared to extend radial fibers, resembling the symmetrical divisions attributed to embryonic vRGs that divide with a vertical cleavage plane.

We next investigated whether recently described (Fietz, S. A., et al (2010). Nat Neurosci 13, 690-699) (Hansen, D. V., et al. (2010). Nature 464, 554-561) human-enriched outer sub-VZ (SVZ) radial glial (oRG)-like cells were present in our cultures. We focused on NKX2.1-GFP+ cells with unipolar fibers located away from the rosette clusters (FIGS. 2D and 2F). We discovered GFP+ oRG-like cells displaying mitotic somal translocation (MST) prior to division. These cell bodies translocated toward the unipolar fiber and divided with a horizontal cleavage plane (perpendicular to the fiber). In summary, hESC-derived MGE-like progenitors (also called MGE precursor cells) could recapitulate VZ and human-enriched SVZ radial glial-like stem cell behaviors.

Figure 2:
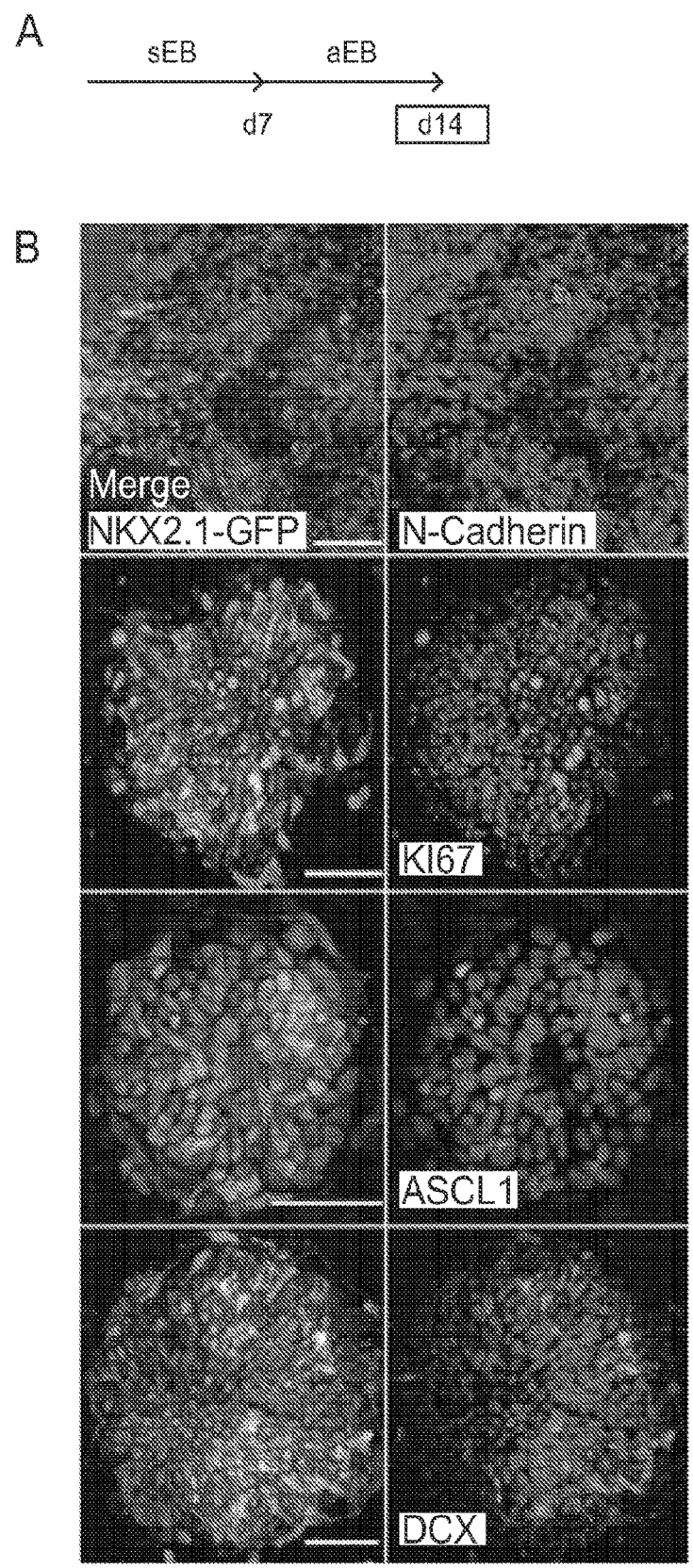
FIG. 2 (Panels A-F) illustrate hESC-MGE-like progenitors exhibit VZ and SVZ Radial Glial Stem Cell-like Divisions.
Figure 2:
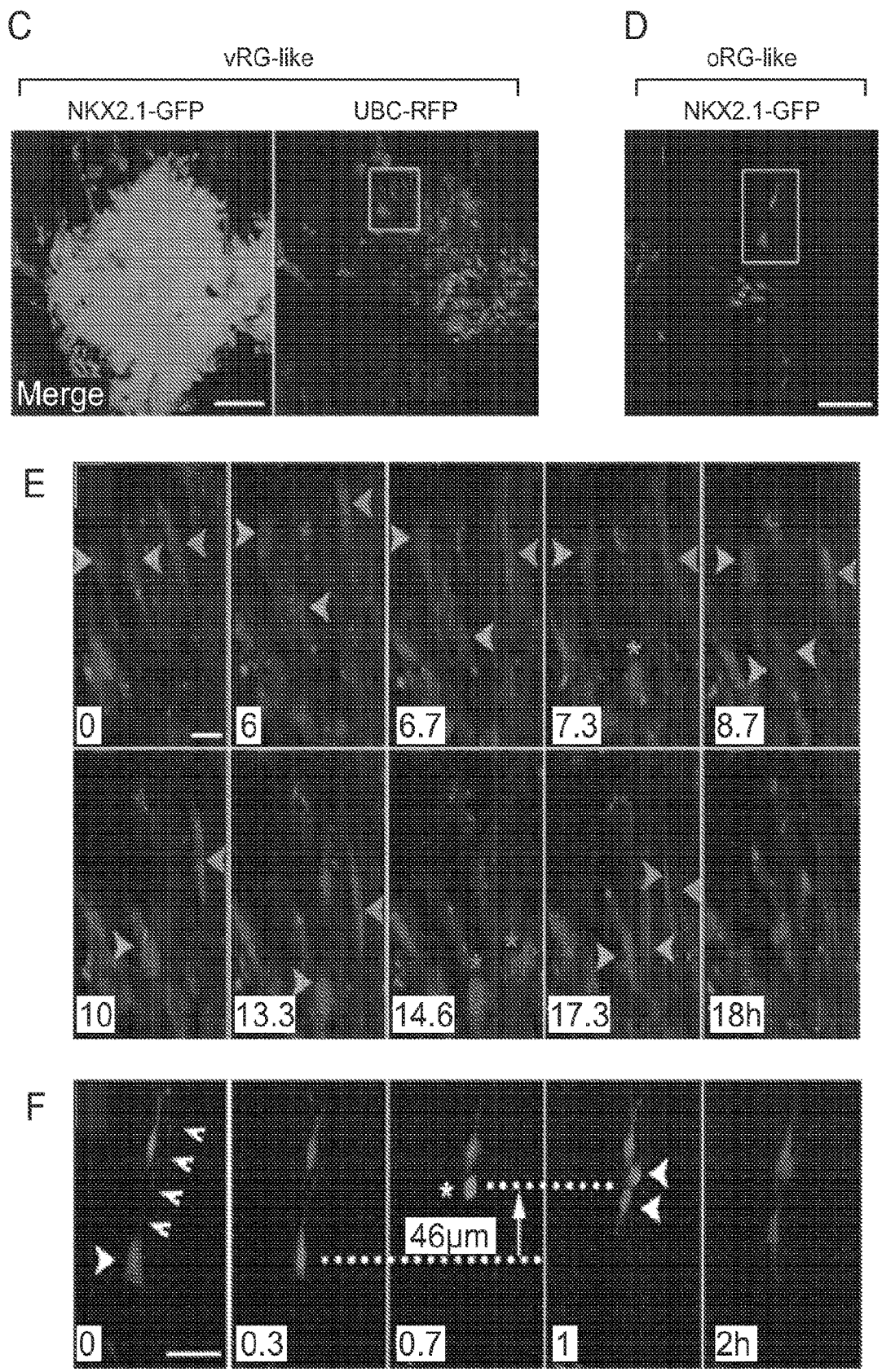

FIG. 2. hESC-MGE-like Progenitors (also referred to as MGE precursor cells) Exhibited VZ and SVZ Radial Glial Stem Cell-like Divisions. (A) sEBs plated en-bloc on day 4-7, and aEBs fixed on day 14 for analysis; or aEBs were infected with UbC-RFP virus and live cultures time-lapse imaged. (B) Day 14 NKX2.1-GFP expression and a panel of markers in red shown merged and separate: N-Cadherin, KI67, ASCL1, and DCX. Blue: DAPI. Scale Bar: 50 µm. (C) A cluster of rosettes with RFP fluorescence alone or merged with NKX2.1-GFP. (D) NKX2.1-GFP expressing cells outside of the clusters. C, D Scale Bar: 100 µm. (E) Time-lapse imaging series of boxed region (C) showing three RFP+ cells (blue, orange, and green arrowheads) that displayed vRG-like INM behavior: translocation toward the rosette lumen and division (star) with a vertical cleavage plane. Time: hours. Scale Bar: 20 µm. (F) Time-lapse series of boxed region (D). A GFP+ cell with characteristic unipolar morphology (white arrowhead and smaller arrowheads to mark fiber) exhibited oRG-like MST behavior: translocation toward the fiber (46 µm) and division (star) with a horizontal cleavage plane. Time: hours. Scale Bar: 50 µm.

Example 3: hESC-Derived MGE-Like Progenitors Generated GABAergic Interneurons

We further explored the identity and fate of the hESC-derived cultures. Immunostaining analysis was conducted on d25 aEBs (FIGS. 3A and 3B). Day 25 aEBs were also dissociated, cultured as a monolayer (ML), and immunostaining analysis was performed and quantified on day 35 (FIGS. 3C-3E). At both day 25 and day 35 stages, NKX2.1-GFP expression was specific to cells expressing endogenous NKX2.1 protein (91.3±1.7%) (FIG. 3E). On day 25, FOXG1 and OLIG were expressed in most of the NKX2.1-GFP+ cells, providing further evidence for ventral telencephalic-like identity (FIG. 3B). By day 35, most GFP+ cells continued to express FOXG1 (81.5±3.6%) but had downregulated OLIG2 (6.8±3%). The majority of GFP+ cells also expressed ASCL1 (79.9±6.5%) and DLX2 (79.8±3.7%) by day 35. Since OLIG2 marks GE progenitors while DLX2 marks GABAergic neuronal lineages, these results suggested that day 25 hESC-derived MGE-like progenitors (also referred to herein as MGE precursor cells) began to differentiate into GABAergic neurons by day 35. Indeed, neuronal identity was confirmed by TUJ1 (92±2.4%) staining (FIGS. 3D and 3E). Most of the GFP+/TUJ1+ cells co-expressed GABA (75.8±2.3%). The interneuron subtype marker Calbindin (CALB1 or CALB) was also expressed by day 35 (31.1±5.4%), but other interneuron subtype markers Calretinin (CALB2 or CALR), Somatostatin (SD), and Parvalbumin (PVALB or PV) were not detected at this stage, except in rare instances for SST or CALR.

A minority of GFP+ cells expressed the diencephalic/oligodendrocyte marker NKX2.2 (13.6±4.7%), neural progenitor/glial cell markers GFAP (3.9±3.9%) and KI67 (2.8±1.5%), LGE/POA-enriched marker ISLET1 (7.6±3.3%), or dopaminergic neuron marker TB (4.4±1.3%) (FIG. 3E). Virtually none of the GFP+ cells expressed the neocortical marker PAX6, caudal GE (CGE)/dorsal MGE marker COUPTFII, striatal medium spiny neuron marker DARPP32, globus pallidus projection neuron marker ER81/ETV1, cholinergic neuron marker CHAT, or glutamatergic neocortical projection neuron subtype marker TBR1 (FIG. 3E). Based on these results, hESC-derived MGE-like progenitors appeared to have differentiated into predominantly post-mitotic GABAergic interneurons.

Figure 3:
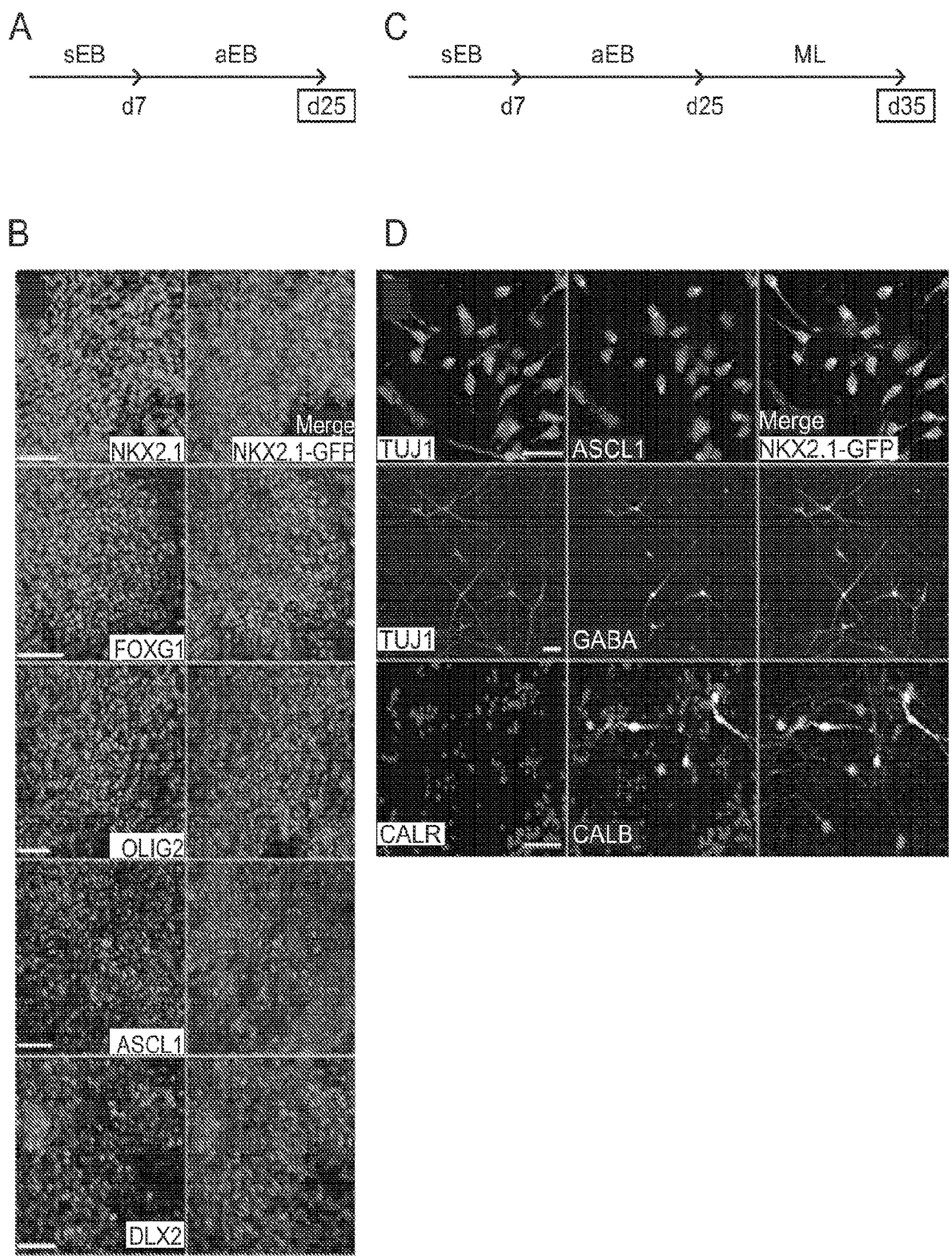
FIG. 3 (Panels A-E) illustrate hESC-MGE-like progenitors differentiate into neurons with properties of telencephalic GABAergic interneurons.
Figure 3:
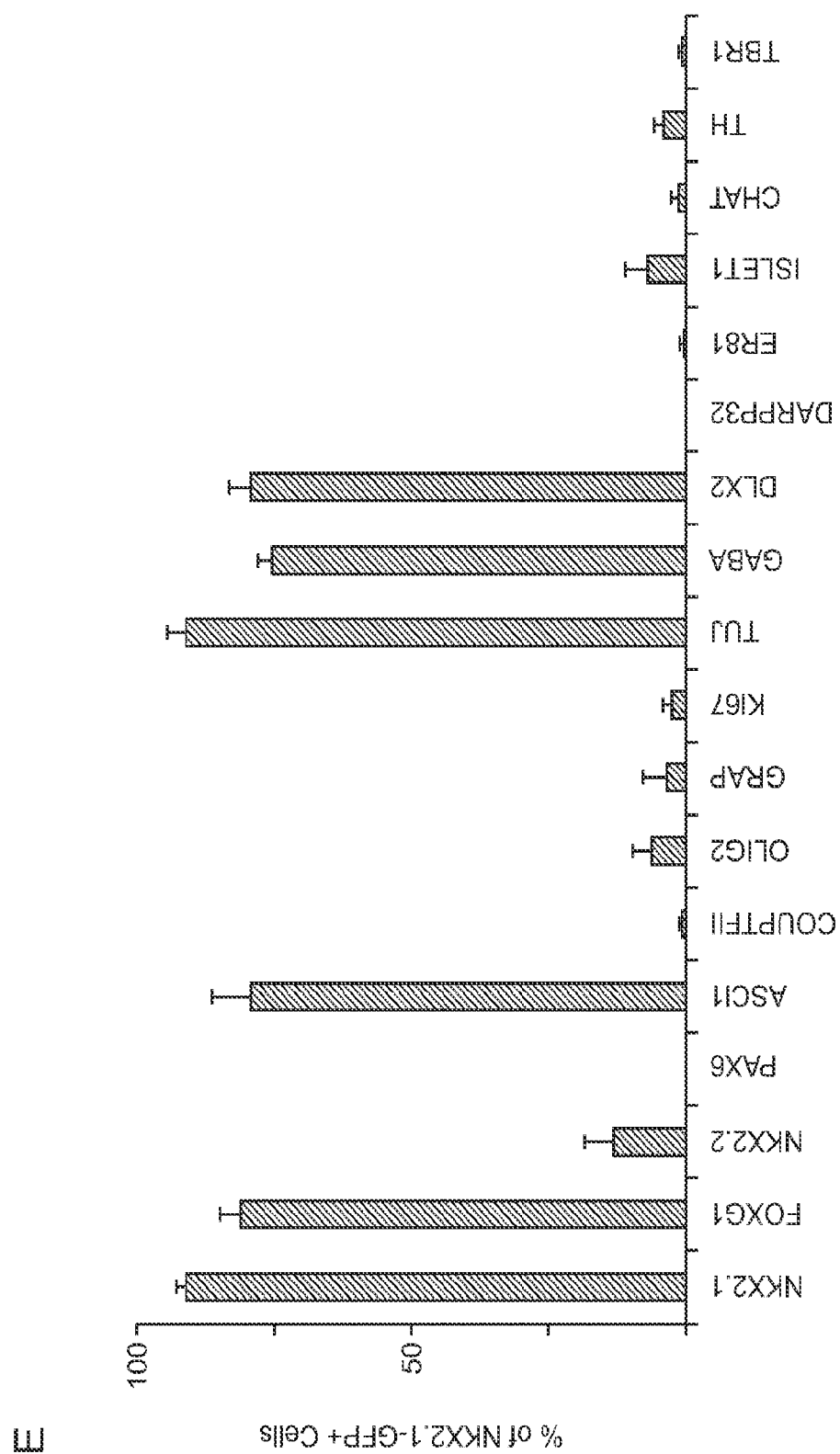

FIG. 3, hESC-MGE-like Progenitors Differentiated into Neurons with Properties of Telencephalic GABAergic Interneurons. (A) aEBs fixed for immunofluorescence staining on day 25. (B) Day 25 MGE-like progenitor cells expressed NKX2.1-GFP, NKX2.1, FOXG-1, OLIG2, ASCL1, and DLX2. Blue: DAPI. Scale Bar: 50 µm. (C) aEBs dissociated, replaced as a ML, and fixed for day 35 immunofluorescence. (D) Day 35 dissociated cells expressed NKX2.1-GFP, TUJ1, ASCL1, GABA, and CALB. Blue: DAPI. Scale Bar: 50 µm. (E) Quantification of day 35 immunostaining. The majority of NKX2.1-GFP+ cells expressed NKX2.1, FOXG-1, ASCL1, TUJ, GABA, and DLX2. Data represented as mean±SEM.

Example 4: hESC-Derived NKX2.1-GFP+ Microarray Profiling

We performed microarray profiling to obtain a global transcriptome comparison of undifferentiated hESCs and FACS-sorted NKX2.1-GFP+ populations over a 55-day time course of differentiation: from 20-day aEBs (blue bars) or 35-day adherent monolayers (orange bars), or from 55-day cultures (green bars) that had been previously labeled with UbC-RFP virus, sorted for GFP on day 35, and co-cultured with glial cells (FIG. 4A). The percentage of NKX2.1-GFP+ cells remained at a high level in dissociated monolayer culture (~81% on d35) or in co-culture (~94% of RFP+ cells on d55) (FIG. 4B). Dendrogram clustering analysis showed the differentiated GFP+ populations to be more closely related to each other than to undifferentiated hESCs (FIG. 10A). To inspect the identities of the hESC-derived GFP+ populations in greater detail, we selected panels of lineage-specific markers and assessed transcript hybridization intensities over the time course (FIGS. 4C-4H and 10C-10F). For a subset of markers, quantitative RTPCR. was performed and confirmed the array data (FIG. 10B). Markers of pluripotency were only detected in undifferentiated hESCs, whereas markers of a neural lineage (HES5, DCX, SYP, SYN1) were induced in differentiating GFP+ cells. Markers of glial cells, neural crest, or microglia were not detected. In contrast, GFP+ cells expressed neuronal markers (TUBB3, DCX, SYP, SYN1), and transcript levels increased over time. We then examined anterior-posterior central nervous system (CNS) patterning and detected expression of anterior CNS markers (FOXG1, SIX3, OTX2). In agreement with prior results, diencephalic (and more caudal) NKX2.2 was transiently expressed and then downregulated. Unexpectedly, FOXA2, a marker of CNS floor plate, was expressed in day 20 progenitors but was not detected at later time points.

We next investigated markers that identify sub-regions of the forebrain. Aside from temporary expression of NKX2.2, markers of diencephalic hypothalamus were not robustly expressed (FIG. 10C). Also, dorsal excitatory neuronal lineage markers were not detected (FIG. 10D). Instead, ventral telencephalic GABAergic neuronal lineage markers (ASCL1, DLX1, DLX5) were expressed along with MGE markers (NKX2.1, LHX6, LHX8, CXCR7), and their expression intensities generally increased over time (FIGS. 4F and 4H). Markers of non-MGE ventral telencephalon were not detected, nor were markers of NKX2.1+ POA/septum or globus pallidus (FIG. 10E). GABAergic markers (GAD1, SLC32A1, SLC6A1) were found, but glutamatergic or cholinergic neuronal markers were not expressed (FIG. 4G). We detected dopaminergic neuronal transcript (TH) but did not identify many neurons expressing TH protein (FIG. 3E). These results suggested that GFP+ cells were of a principally MGE-like GABAergic neuronal lineage.

In addition to cortical GABAergic interneurons, the MGE generates striatal GABAergic interneurons as well as GABAergic projection neurons of the globus pallidus. Since GFP+ cells did not express globus pallidus marker transcript or protein, we further assessed markers of cortical/striatal interneuron lineages.

Striatal interneurons maintain NKX2.1 and LHX8 expression, whereas migratory cortical interneurons extinguish these markers and express ZEB2, MAF, ARX, CXCR7, and CXCR4. In support of a cortical-like interneuron lineage, robust CXCR7 expression was detected in GFP+ cells. Although increased ZEB2, ARX, and CXCR4 transcript signals were found at later stages, overall levels were modest, and NKX2.1 and LHX8 continued to be expressed, suggesting a striatal interneuron-like lineage and/or a cortical-like lineage at an immature stage (FIGS. 4F and 4H). Lastly, of the neuropeptide and calcium binding proteins that mark subtypes of interneurons, only SST transcript was robustly detected by day 55 (FIG. 4H). In summary, the hESC-derived NKX2.1-GFP+ populations represented MGE-like neural progenitor cells and GABAergic cortical-and/or striatial-like interneurons.

Figure 4:
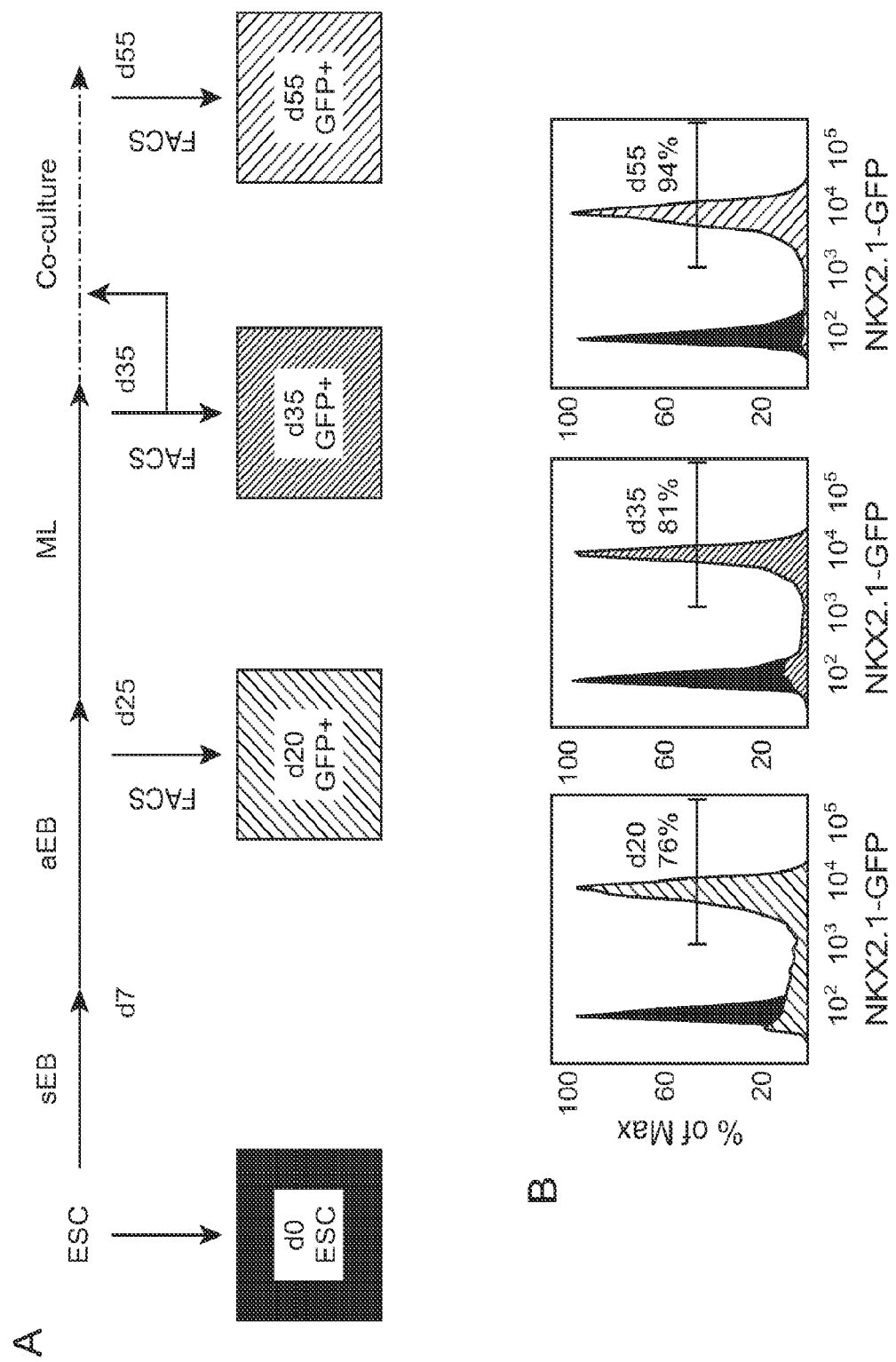
FIG. 4 (Panels A-H) depict microarray gene expression profiling of hESC-MGE-like NKX2.1-GFP+ Cell Populations.
Figure 4:
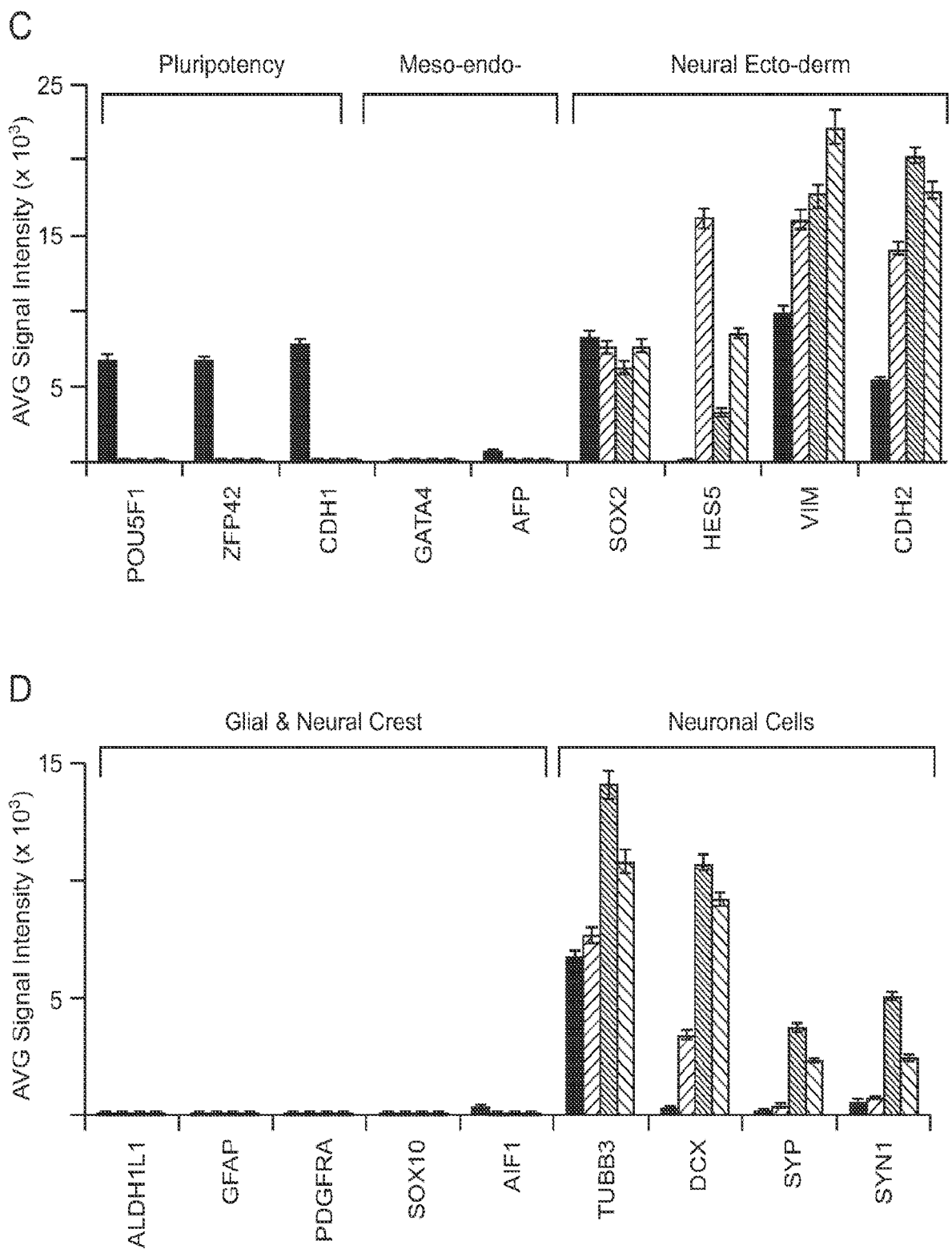
Figure 4:
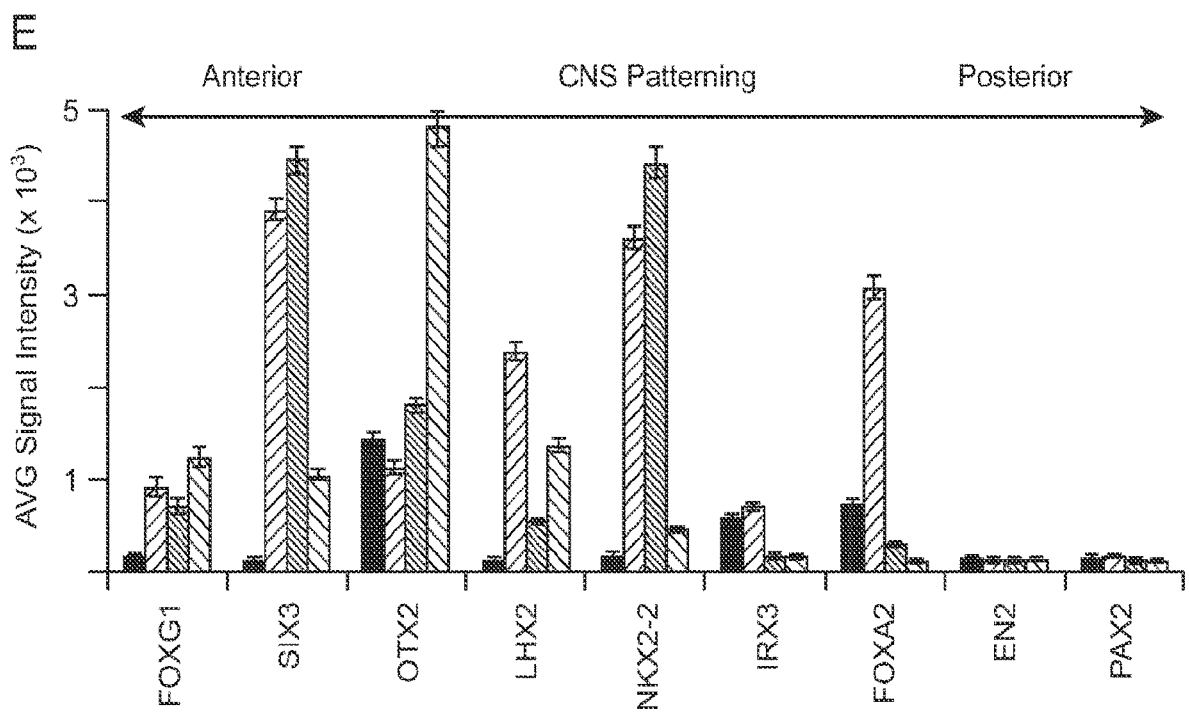
Figure 4:
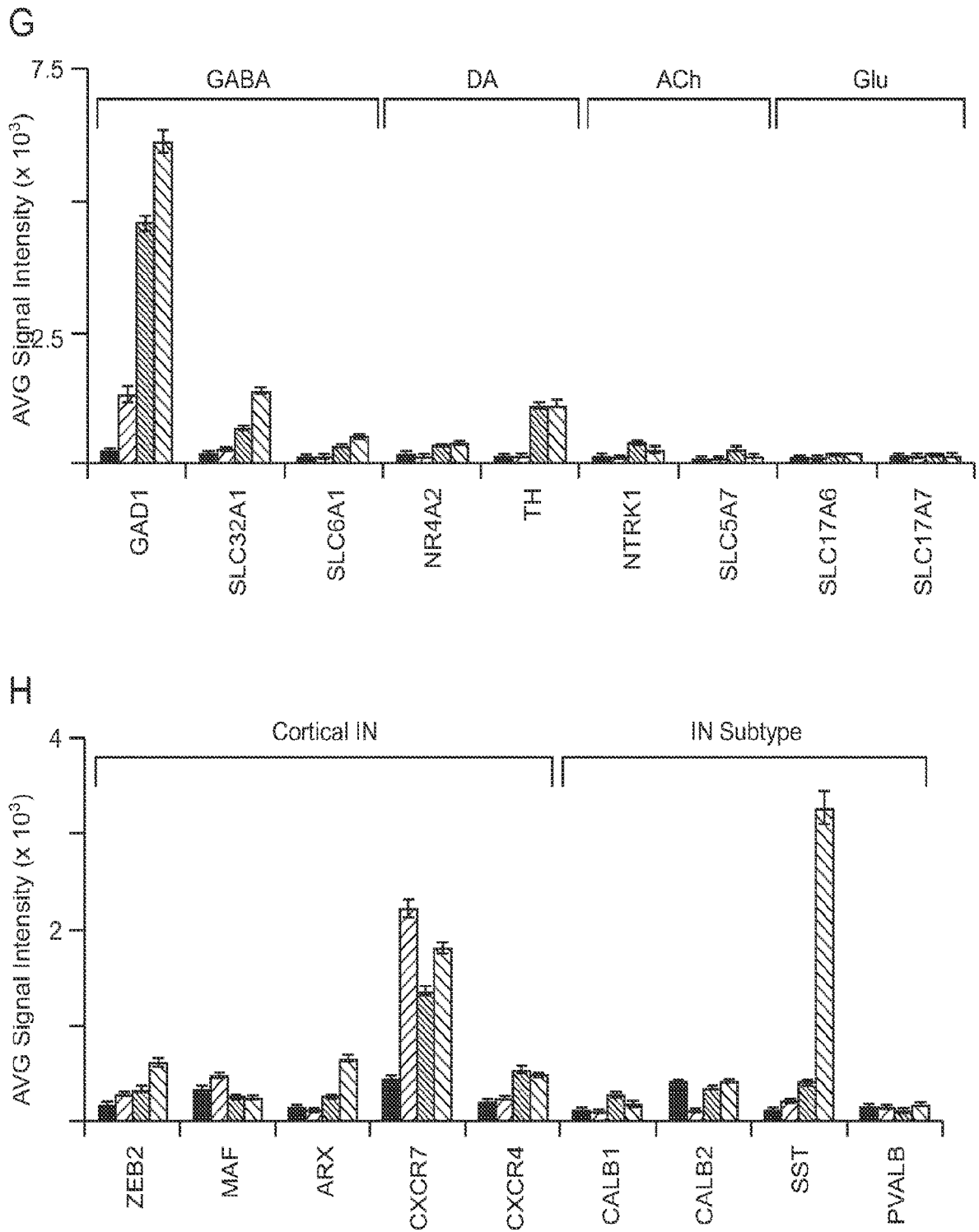

FIG. 4. Microarray Gene Expression Profiling of hESC-MGE-like NKX2.1-GFP+ Cell Populations. (A) Schematic and legend for microarray data. Undifferentiated hESCs (black); and FACS-sorted GFP+ cells from day 20 aEBs (blue), day 35 ML cultures (orange), and GFP+ cells from d35 co-cultured to day 55 (green). (B) Representative FACS histogram analysis of each differentiation stage and undifferentiated hESC controls (black). (C-H) Average transcript hybridization signal intensities for marker panels. IN=interneuron, DA=dopaminergic, ACh=cholinergic, Glu=glutamatergic. Data, represented as mean±SEM. See also FIG. 10.

Figure 10:
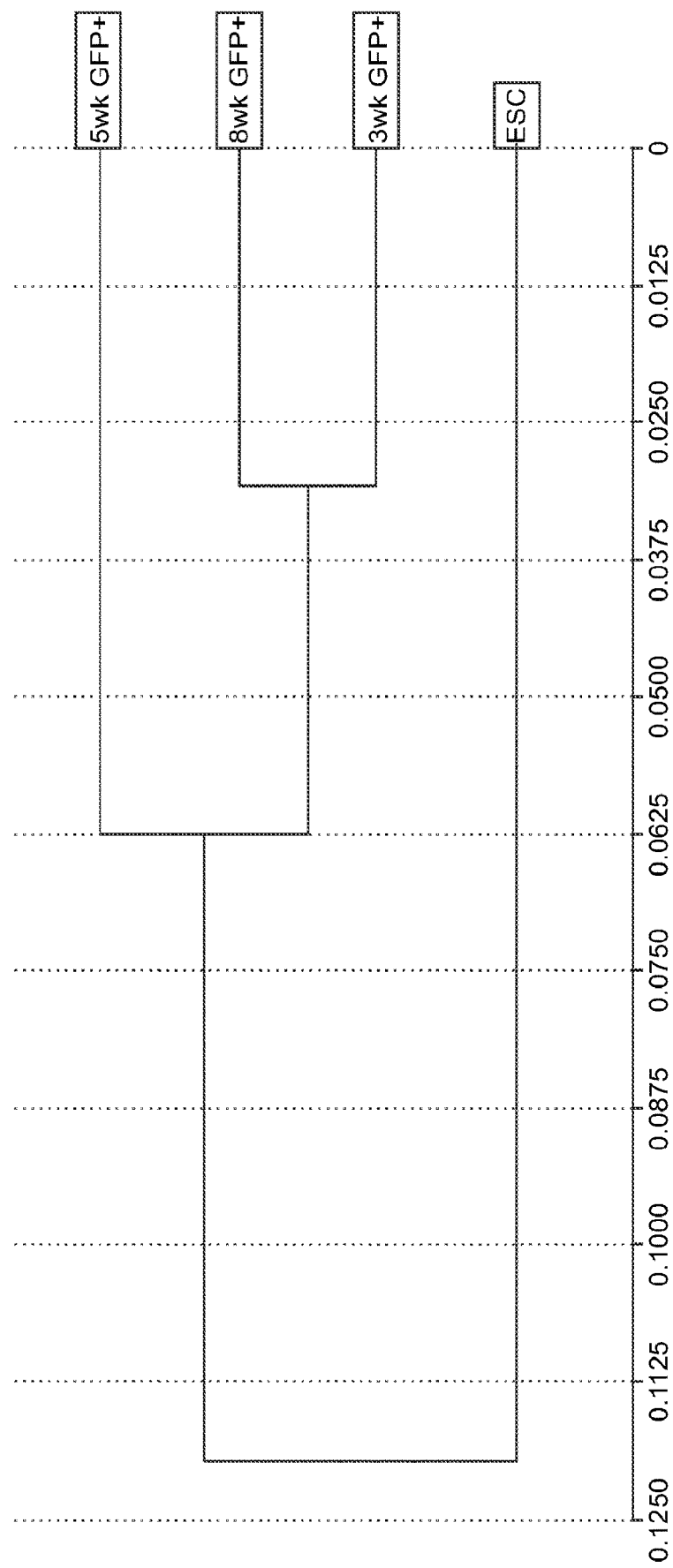
FIG. 10 (Panels A-F) depict transcript expression profiling of hESC-derived NKX2.1-GFP+ cells.
Figure 10:
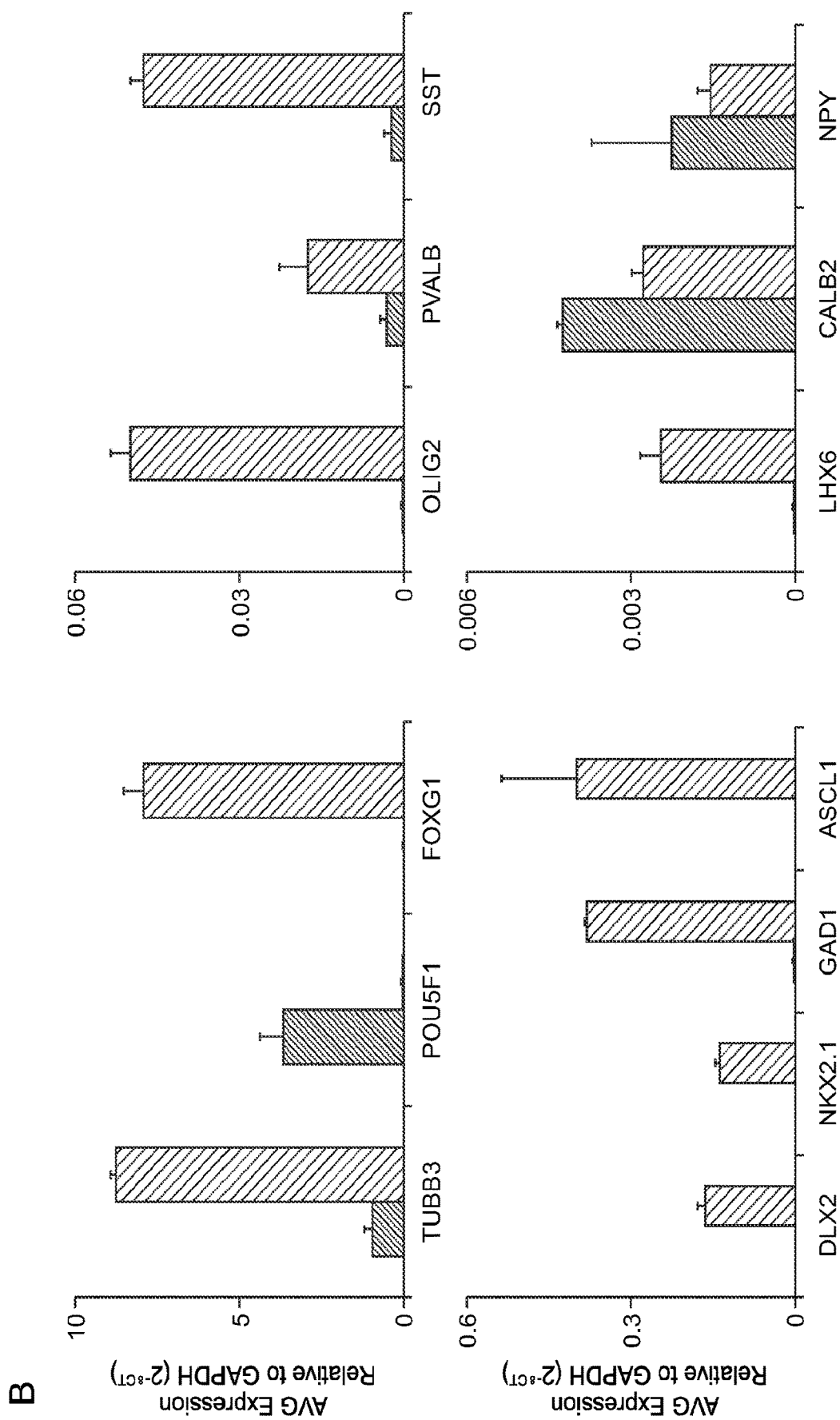
Figure 10:
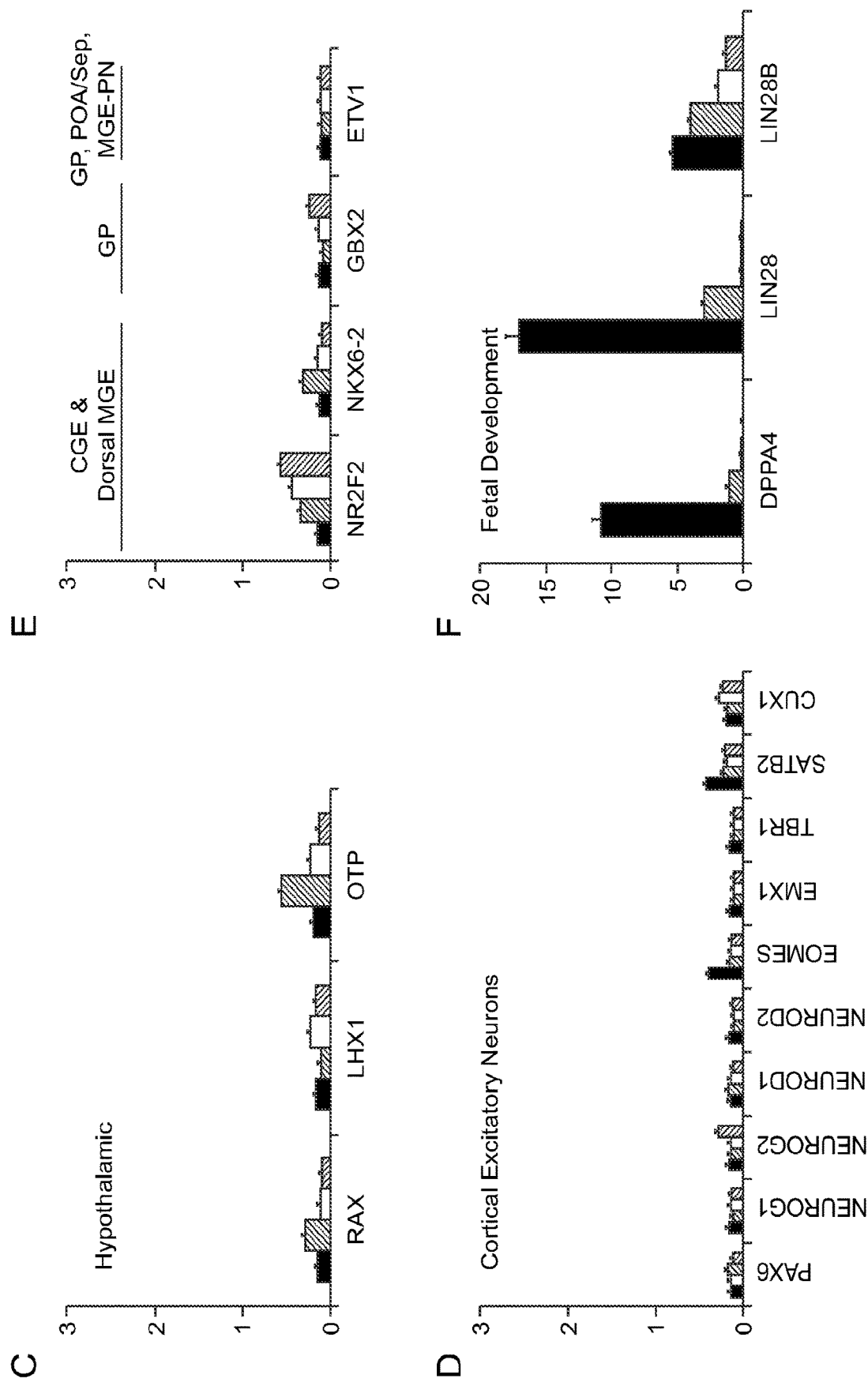

FIG. 10. Transcript expression profiling of hESC-derived NKX2.1-GFP+ cells, related to FIG. 4.

(A) Dendrogram clustering analysis of microarray data identified the d20, d35, and d55 GFP+ populations to be more closely related to each other than to the undifferentiated hESCs.

(B) Quantitative RTPCR analysis of undifferentiated hESCs (black bars) and 3-week GFP+ cells (blue bars) relative to GAPDH expression. Data represented as mean±SD.

(C-F) Additional markers from microarray analysis. Legend: undifferentiated hESC (black), d20 GFP+ (blue), d35 GFP+ (orange), and d55 GFP+ (green) samples. Panels show: hypothalamic (C), cortical excitatory neuronal lineage (D), ventral telencephalic (E), and general fetal developmental markers (F). GP=globus pallidus, POA=pre-optic area, Sep=septum, PN=projection neuron. Hypothalamic and cortical excitatory neuronal markers were not detected. The POA/Sep, GP, and MGE-derived PN markers, ETV1 and GBX2, were also not detected. The dorsal MG E and CGE marker, NR2F2 (COUPTFII), was identified at a low level, consistent with rare GFP+ cells expressing COUPTFII protein (FIG. 3E), and NKX6-2 was also weakly detected at d20. The early embryonic markers, DPPA4, LIN28, and LIN28B, have been used to estimate the developmental stage of neural cells derived from human pluripotent stem cells (Patterson, M., et al. (2012). Cell Res 22, 178-193). In human fetal spinal cord, LIN28 expression is downregulated by 7 gw, whereas DPPA4 and LIN28B are not reduced until 13 gw. In our cultures, DPPA4 and LIN28 were not detected by d35, and LIN28B expression persisted to d55. These results suggest d35-55 GFP+ cells may be similar to a 7-13 gw fetal developmental stage. Data represented as mean±SEM.

Figure 11:
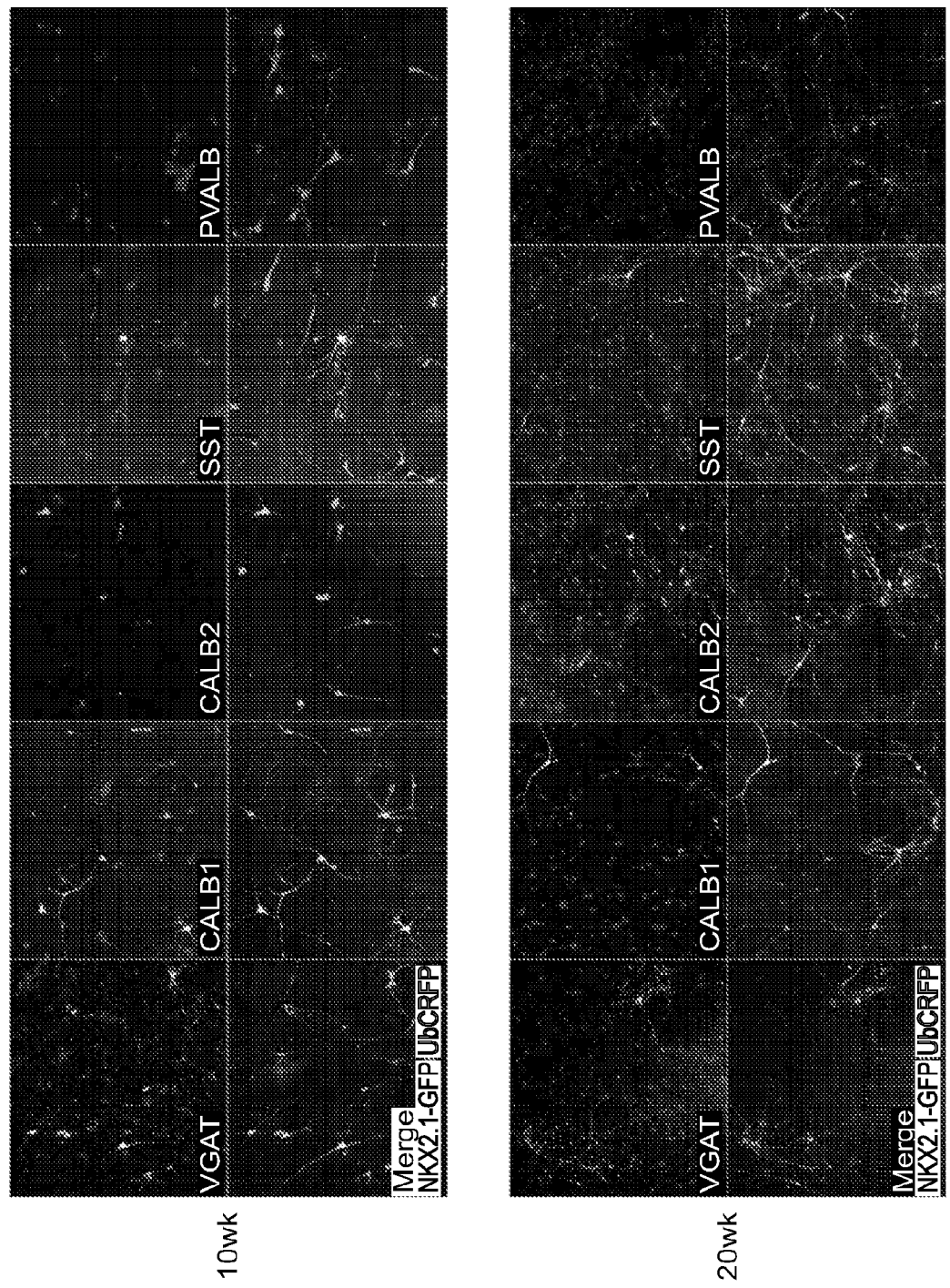
FIG. 11 depicts maturation of hESC-derived MGE-like cells into GABAergic interneuron subtypes.

Example 5: Protracted Maturation of hESC-Derived MGE-Like Cells into Subtypes of GABAergic Interneurons We next sought to more convincingly determine both the neuronal subtypes generated by the NKX2.1-GFP+ MGE-precursor like cells and the developmental timeline of subtype maturation. To study their maturation, day 35 FACS-sorted GFP+ cells were co-cultured with cortical glial cells (FIG. 5A), and some cells were labeled with UbC-RFP virus prior to co-culture. Cultures were fixed for analysis after five, 10, 20, and 30 weeks post-differentiation (WPD), and neuronal subtype marker expression was quantified (FIG. 5C). Following 30 WPD, RFP+ hESC-derived neurons were notably larger in somal size and expressed the GABAergic neuron-specific marker, VGAT, and interneuron subtype markers SST, CALB, and CALR (FIG. 5B). Images from 10-20-WPD cultures are shown in FIG. 11, Virtually all neurons at five WPD expressed NKX2.1-GFP, but, similar to cortical interneurons, the percentage of NKX2.1+ neurons significantly declined by 30 WPD (66.7±6.1%; p=0.03). Most of the neurons expressed GABA (75-86%) and VGAT (53-78%) from 5-30 WPD. Aside from rare cells (11 of 3,110 neurons), the excitatory neuronal marker TBR1 was not expressed. CALB was expressed in neurons throughout the time course (24-36%). In contrast, the percentage of SST+ and CALR+ neurons increased over time and were significantly induced from 10 to 20 WPD (SST: 2.8±1% to 12.8±9%; p=0.03, and CALR: 8.8±4.9% to 52.6±6.2%; p=0.004). By 30 WPD, the percentage of SST+ neurons increased to 40.6±8.6%, and CALR+ neurons increased to 77.7±14.9%. Conversely, PV+ neurons were not detected by 30 WPD (0 of 1,146 neurons), and NPY+ neurons were rare (6 of 819 neurons, not shown). Thus, NKX2.1-GFP+ MGE-like cells matured into NKX2.1+ and NKX2.1-negative GABAergic interneurons expressing CALB, CALR, and/or SST subtype markers, and pronounced SST and CALR subtype maturation occurred between 10 and 20 WPD.

It was surprising that our hESC-derived GABAergic interneurons required 20-30 weeks to show substantial expression of SST and CALK. However, this protracted timeline of differentiation is similar to human fetal and infant interneuron subtype development (Fertuzinhos, S., et al. (2009). Cereb Cortex 19, 2196-2207). We confirmed these findings with our own histological analysis of developing human cortex and MGE (FIGS. 12A and 12B). To further investigate human fetal MGE-derived fates, we dissected, labeled with UbC-RFP virus, and co-cultured 18 gestational-week (gw) human fetal MGE cells. By 12 weeks in culture, RFP+ human fetal MGE cells had matured into CUB+, CALR+, SST+, and GABA+ neurons, and they did not express TBR1 (FIG. 12C). Therefore, hESC-derived MGE-like cell maturation paralleled both endogenous and cultured human fetal MGE development: comparable interneuron subtypes were generated in a similar sequence and time frame.

Figure 5:
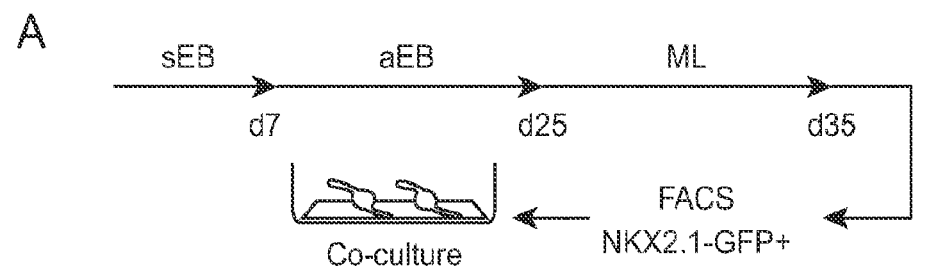
FIG. 5 (Panels A-J) illustrate hESC-MGE-like cell-derived GABAergic interneuron maturation and firing properties.
Figure 5:
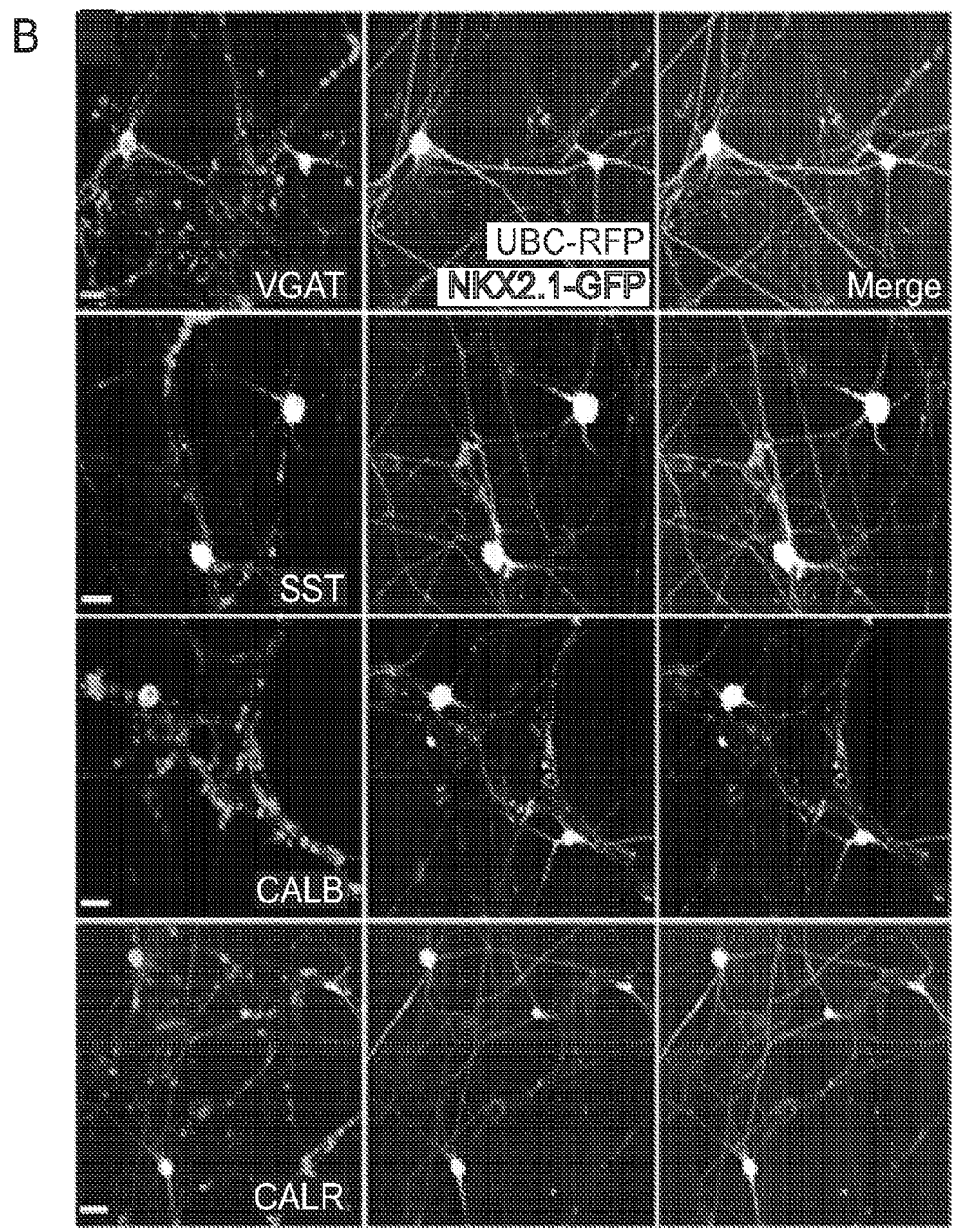
Figure 5:
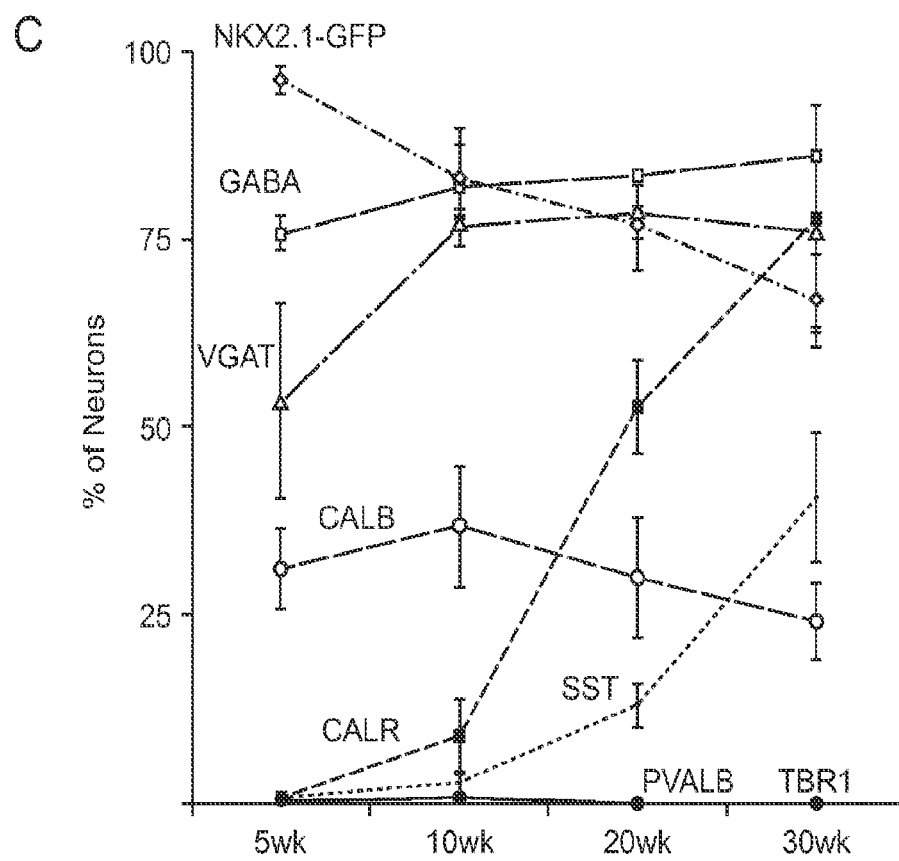
Figure 5:
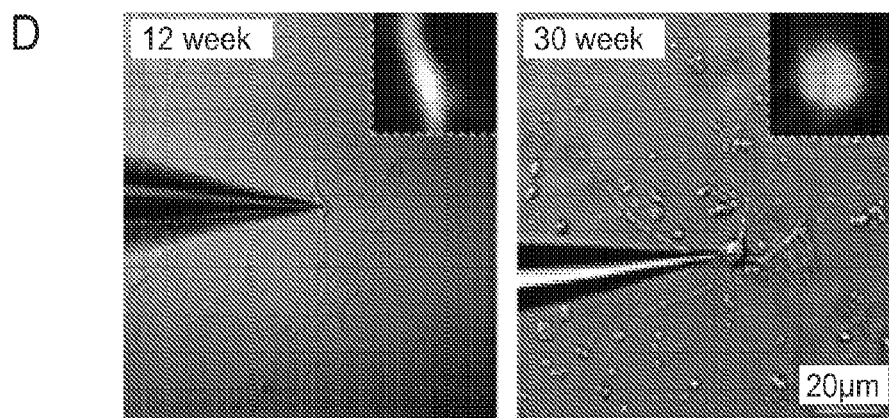
Figure 5:
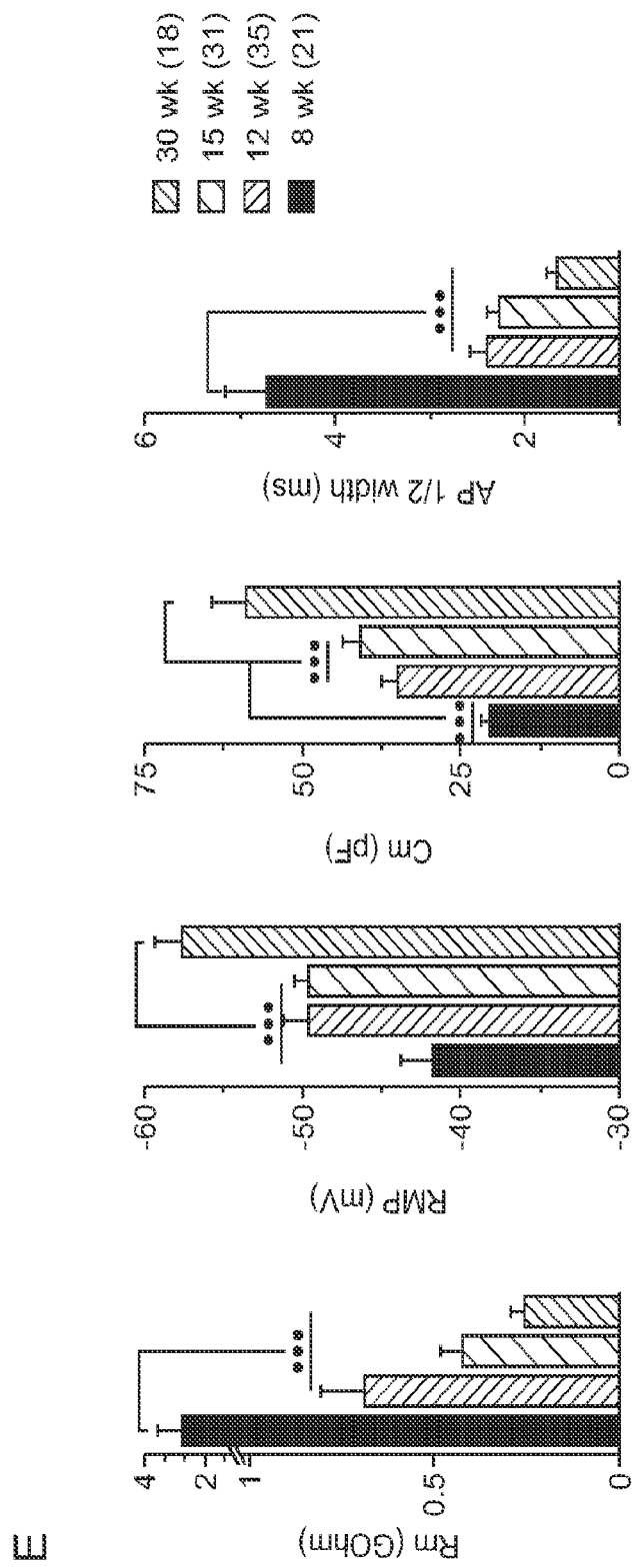
Figure 5:
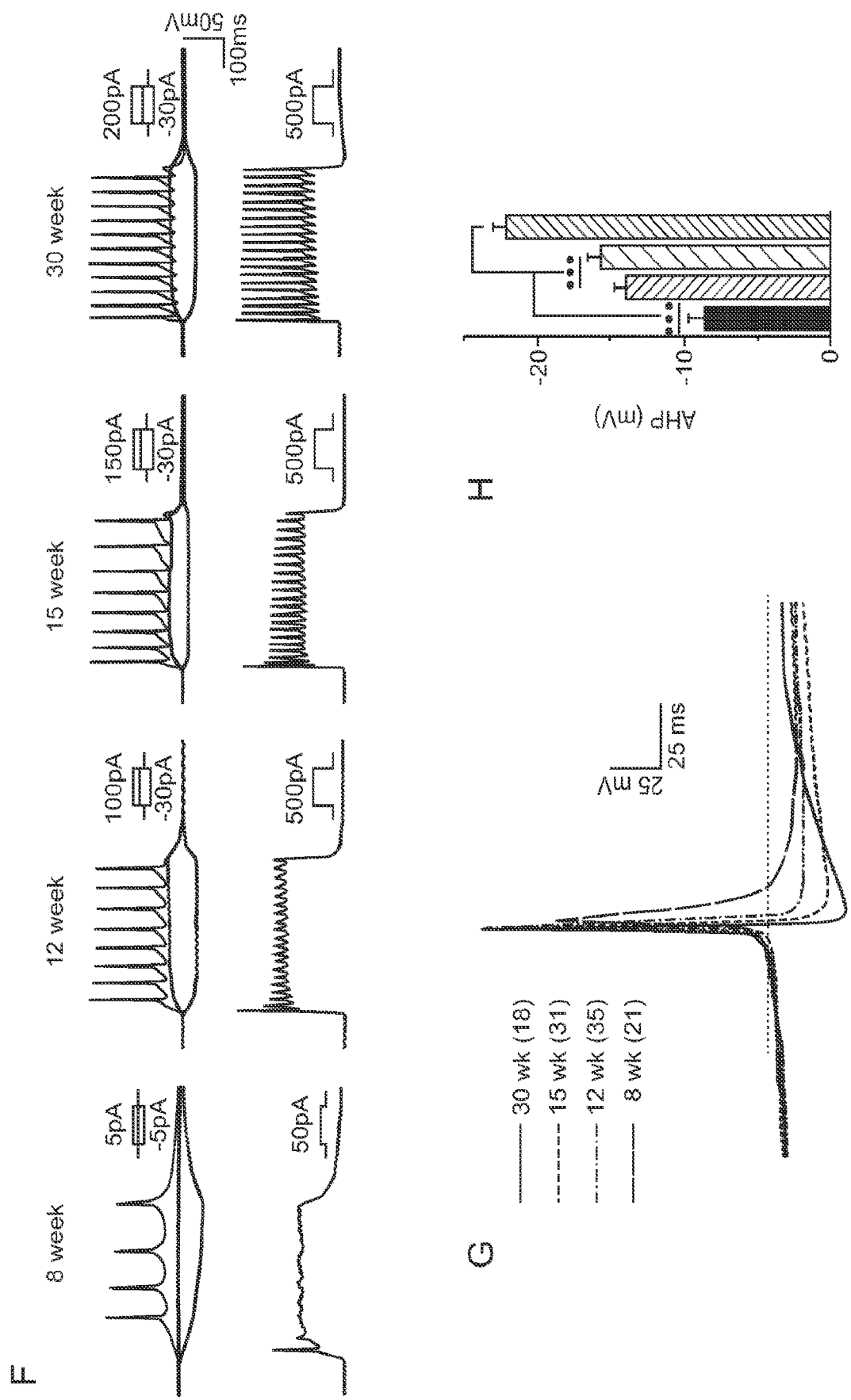
Figure 5:
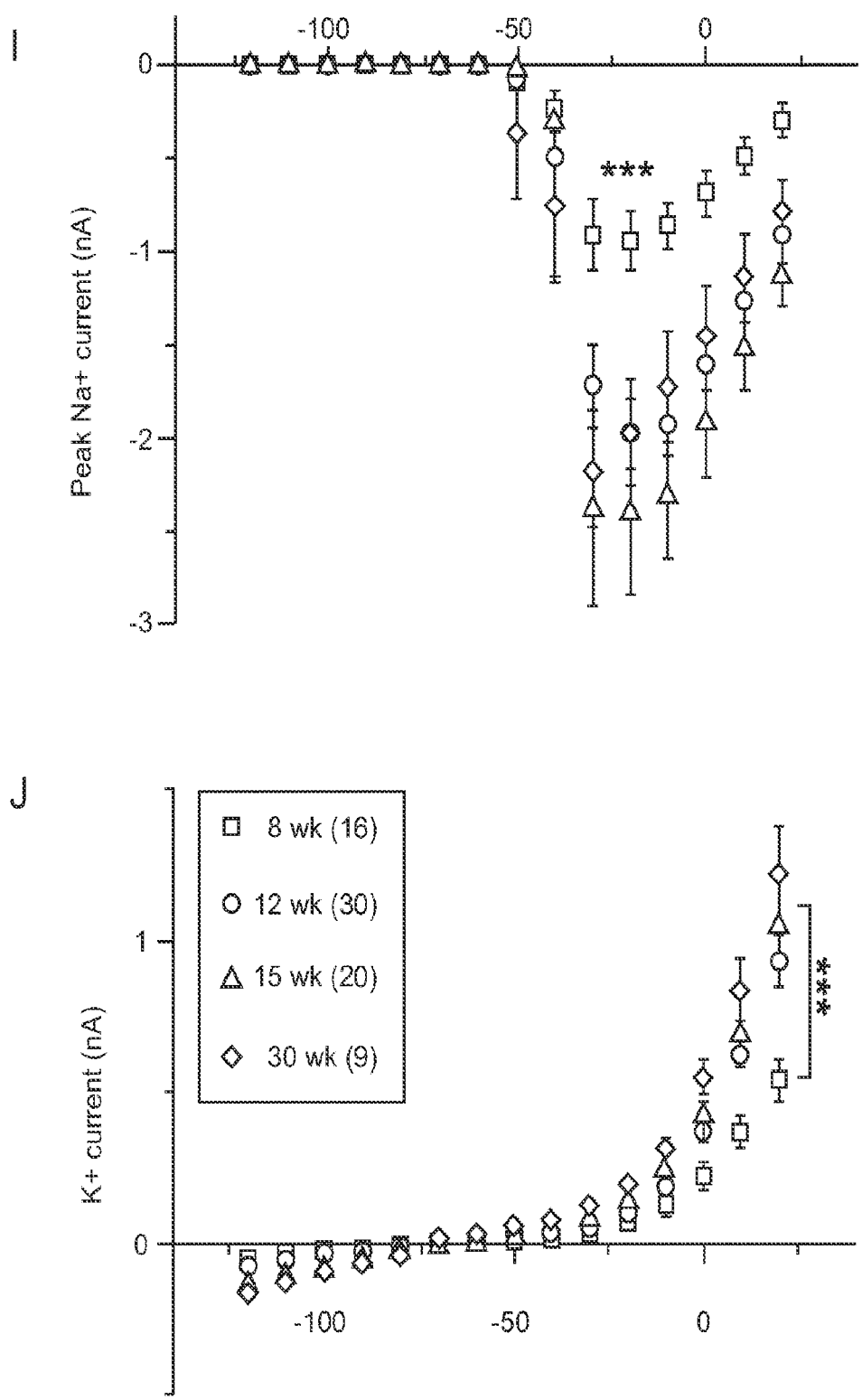

FIG. 5. hESC-MGE-precursor like Cell-derived GABAergic Interneuron Maturation and Firing Properties.
- (A) Dissociated ML cultures infected with UbC-RFP lentivirus, FACS-sorted on day 35 for GFP+ cells, and co-cultured.
- (B) Immunostaining of 30-week cultures showing highly branched RFP+ human neurons that expressed VGAT, SST, CALB, and CALR. Scale Bar: 50 µm.
- (C) Quantification of immunostaining analyses over 5, 10, 20, and 30 weeks. Data represented as mean±SEM. See also FIGS. 11 and 12.
- (D) DIC image of hESC-derived neurons at 12 and 30 WPD, insets show RFP expression of recorded neurons. Scale bar: 20 µm.
- (E) Statistical results showing membrane resistance (Rm), resting membrane potential (RMP), membrane capacitance (Cm), and action potential (AP) ½-width.
- (F) Representative AP firing patterns at each stage upon near threshold (upper) and superthreshold (lower) current injection. Scale bars: 50 mV and 100 ms. See also FIG. 13.
- (G) Average first AP traces upon threshold current injection. Scale bars: 25 mV and 25 ms.
- (H) Statistical results showing AHPs at each stage (dashed line=baseline).
- (I-J) I-V curve of Na$^+$ (I) and K$^+$ currents (J) at each stage, measured under stepped voltages (500 ms duration), E, H, I, J: Data represented as mean±SEM. *** represents p<0.001.

FIG. 11. Maturation of hESC-derived MGE precursor-like cells into GABAergic interneuron subtypes, related to FIG. 5.
- Immunostaining analysis of NKX2.1-GFP+ cells pre-labeled with UbC-RFP virus, FACS-sorted for GFP on d35, and co-cultured for 10 and 20 weeks postdifferentiation (WPD). By 10 WPD, hESC-derived neurons expressed VGAT and Calbindin (CALB1), and rare cells expressed Calretinin (CALB2) or SST. By 20 WPD, human neurons expressed VGAT, CALB1, CALB2, and SST. Parvalbumin (PVAL) was not detected at either time point. Blue=DAPI.

Figure 12:
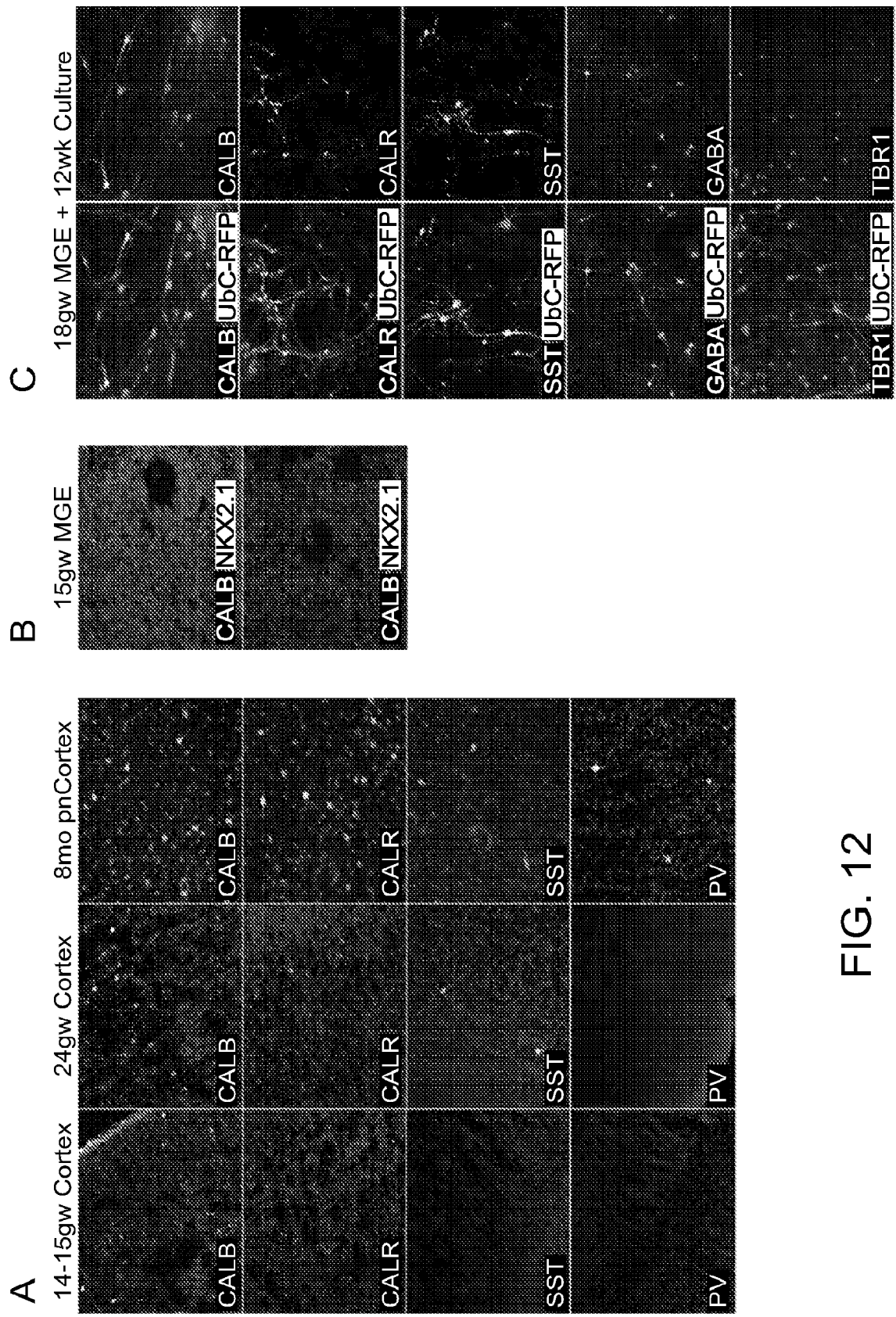
FIG. 12 (Panels A-C) show development of interneuron subtypes in human fetal cortex and MGE, and in cultures derived from human fetal MGE.

FIG. 12. Development of interneuron subtypes in human fetal cortex and MGE, and in cultures derived from human fetal MGE, related to FIG. 5.
- (A) Interneuron subtype marker expression in human fetal cortical sections from 14 15 gw, 24 gw, and 8 mo post-natal. (pn). CALB and CALR were expressed in all samples, but SST and PV were expressed in 24 gw and 8 mo, and 8 mo only samples, respectively. Blue=DAPI.
- (B) Subtype marker expression in 15 gw human fetal MGE sections. Both CALB and CALR were expressed and co-localized with NKX2.1. Blue=DAPI.
- (C) Human fetal MGE was dissociated, labeled with UbC-RFP, FACS-sorted for RFP+ cells, and co-cultured with dissociated human fetal cortical cells. RFP+ cells expressed CALB, CALR, SST, and GABA, but did not express TBR1. Blue=DAP1.

Example 6: Functional Maturation of hESC-Derived MGE-Like Interneuron-Like Firing Properties, Synapse Formation, and GABAergic Output To test whether the hESC-derived cells were functional neurons, we performed whole-cell patch recordings to examine their electrophysiological properties at different WPD (8 weeks, n=21; 12 weeks, n=35; 15 weeks, n=31; 30 weeks, n=18). We found that action potential (AP) firing patterns of hESC-derived neurons were quite immature at eight WPD, judged by the broad AP ½-width of the first AP, small after-hyperpolarization (AHP), and inability to fire repetitively upon high current injection (FIGS. 5E-5H). The peak voltage-gated Na+ and K+ channel currents increased significantly from eight to 12 WPD (FIGS. 5I and 5J), concomitant with a significant decrease in membrane resistance (Rm) (FIG. 5E). Many neurons showed more mature repetitive AP firing upon near threshold current injection at 12 and 15 WPD (FIGS. 5F, 13B and 13C). By 30 WPD, hESCderived neurons exhibited high-frequency repetitive AP firing upon superthreshold current injection (FIGS. 5F and 13D), along with a corresponding increase in membrane capacitance (Cm) and more hyperpolarized resting membrane potential (RMP) (FIG. 5E). In addition, 30-WPD neurons exhibited smaller AP ½-width (FIG. 5E) and larger AHPs (FIGS. 5G and 5H). Consistent with these more mature biophysical properties, we also noted more mature morphologies of the hESC-derived neurons with multiple long processes at 30 WPD compared to the earlier 12 WPD stage (FIG. 5D).

Next, we investigated whether the MGE-like cells were GABAergic neurons by studying their synaptic properties in co-culture with mouse glial cells. hESC-derived NKX2.1-GFP+ neuronal processes co-localized with punctate pre-synapatic VGAT expression, suggesting the formation of GABAergic synapses (FIG. 6A). Spontaneous post-synaptic currents (sPSC) were detected by eight weeks postdifferentiation and were fully blocked by the GABAA receptor inhibitor bicuculline methiodide (BMI, 20 µM), indicating functional GABAergic-specific synapse formation (FIG. 6B). The percentage of neurons receiving sPSCs increased from 33.3% at eight WPD (n=12) to 82.1% at 12 WPD (n=28, FIG. 6C). To confirm that GABAergic neurons were able to send outputs to neighboring neurons, we transfected half of the neurons with Synapsin promoter—Channelrhodopsin2-EYFP (ChR2-EYFP) by lentiviral infection. Blue light stimulation reliably induced action potential firing in EYFP-positive neurons (FIG. 13F) (Weick, J. P., et al. (2011), Proc Natl Acad Sci USA 108, 20189-20194), and evoked robust post-synaptic currents (PSCs) in neighboring neurons (FIGS. 6D and 6E). In addition, the PSCs showed a long decay time (31.4±1.9 ms, n=26), characteristic of GABAergic PSCs. This was further verified by reversible blockade of light-evoked PSCs by BMI (FIGS. 6D and 6E). The reversal potential of light-evoked PSCs was −32.7 mV (FIGS. 6F and 6G), close to the expected Cl-reversal potential under our recording conditions [−37.3 mV=−53.4 mV (by Nernst equation)±16.1 mV (junction potential)]. These results suggested that hESC-derived MGE-like interneurons produced exclusively GABAergic synaptic output.

To examine whether hESC-derived interneurons could form synapses onto primary human neurons, MGE-like cells were labeled at four WPD with ChR2-YFP and UbC-RFP virus, and RFP+ FACS-sorted cells were co-cultured for seven weeks with dissociated human fetal cortical cells from 20 gw. Whole-cell recordings were obtained from RFP-negative primary cortical neurons after co-culture (FIG. 6H). Blue light stimulation of hESC-derived neurons induced GABAergic-specific PSCs in recorded primary neurons that were completely blocked by BMI (FIGS. 6I and 6J). Furthermore, we found polysynaptic responses upon light stimulation (FIG. 6I), which were also blocked by BMI, indicating robust synaptic integration of hESCderived neurons into cultured human fetal neuronal circuits. Thus, hESC-derived neurons demonstrated functional neuronal properties, GABAergic-exclusive synaptic output, and slow 30-week maturation of interneuron firing properties, consistent with the slow pace of subtype marker expression.

Figure 6:
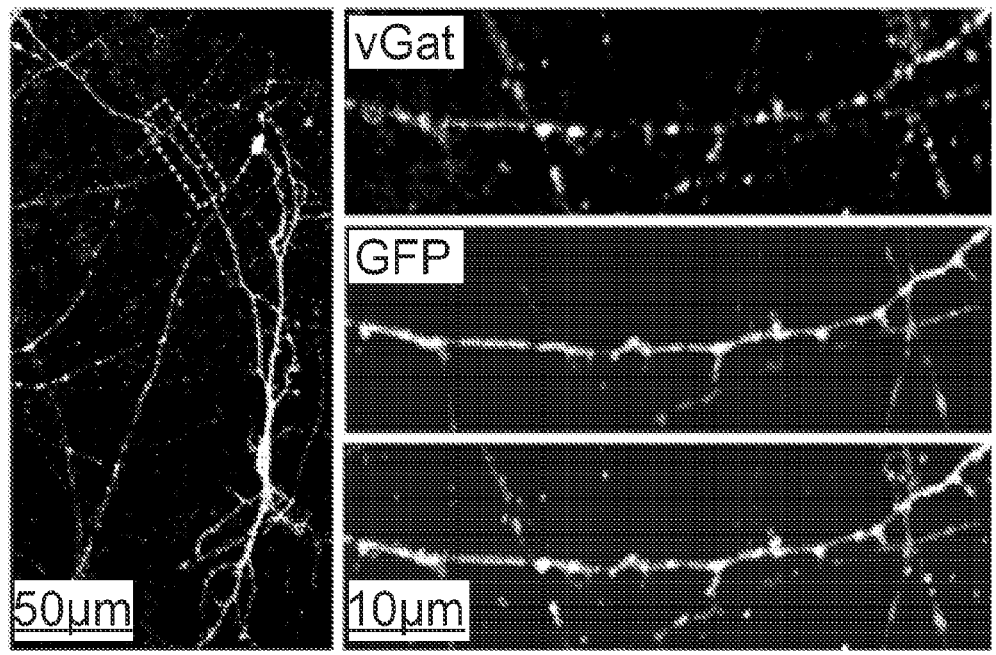
FIG. 6 (Panels A-J) illustrate GABAergic Synaptic Properties of hESC-derived Interneurons.
Figure 6:
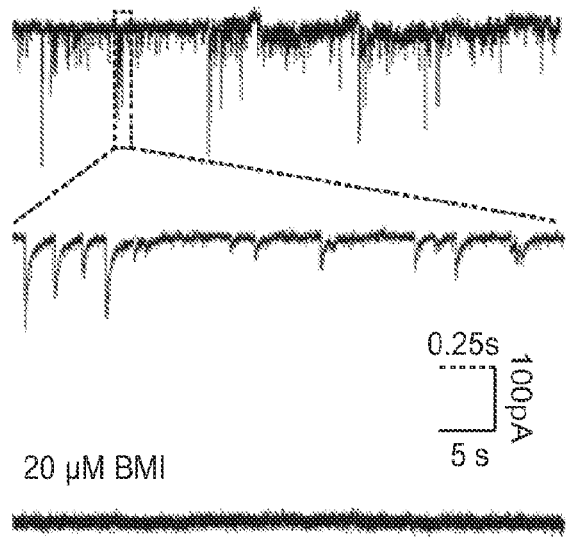
Figure 6:
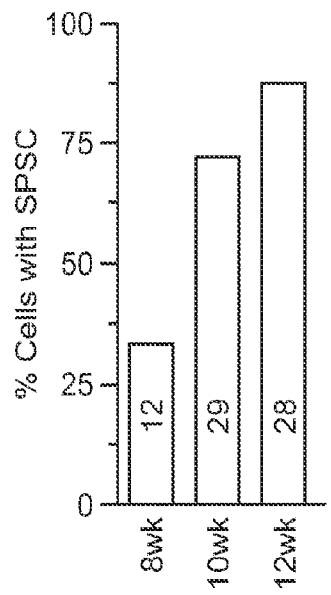
Figure 6:
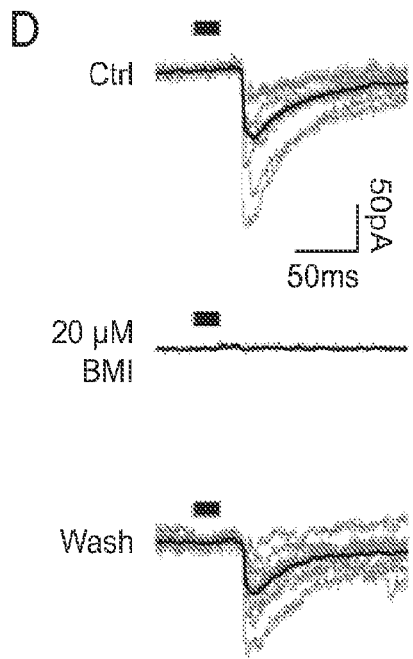
Figure 6:
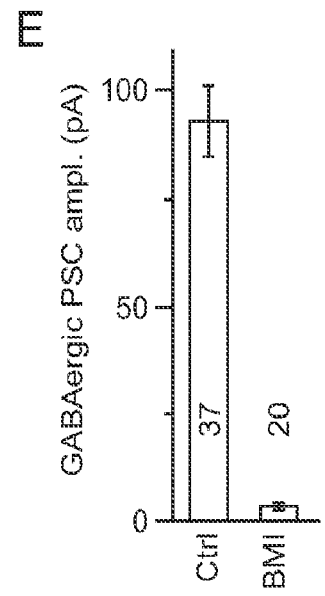
Figure 6:
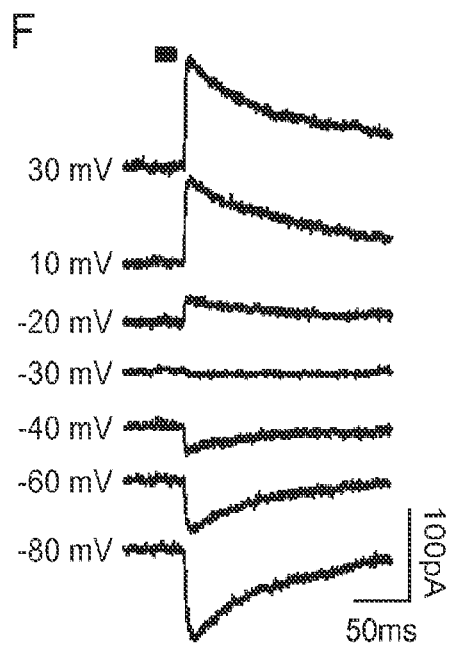
Figure 6:
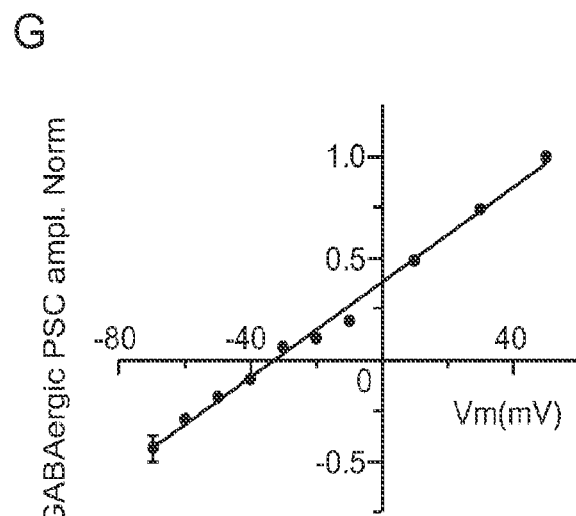
Figure 6:
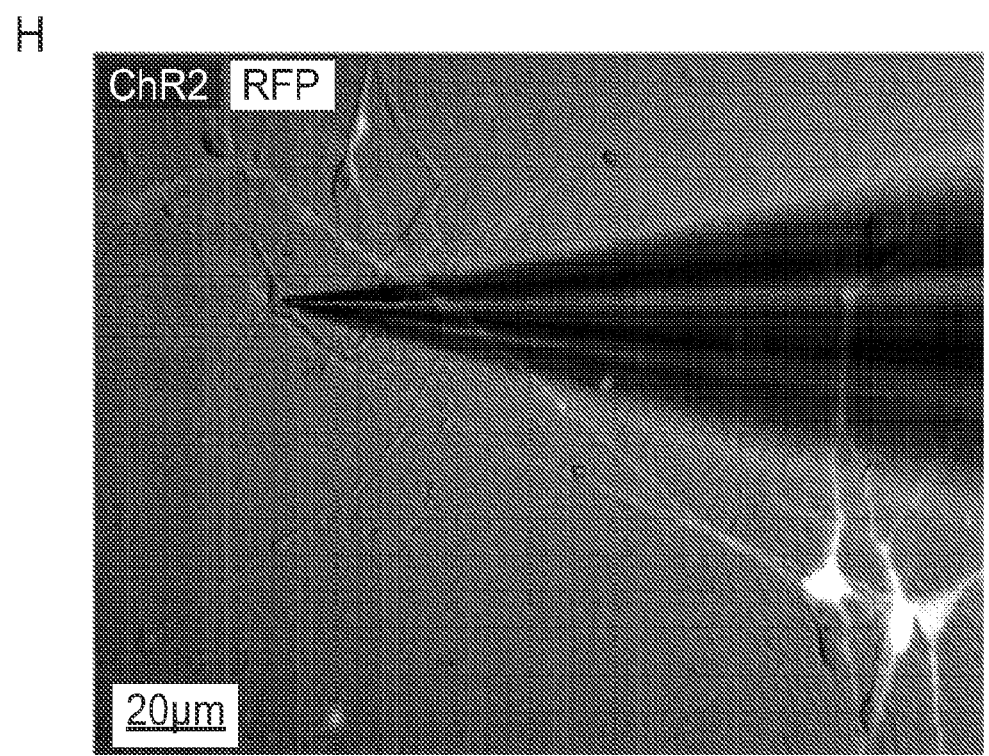
Figure 6:
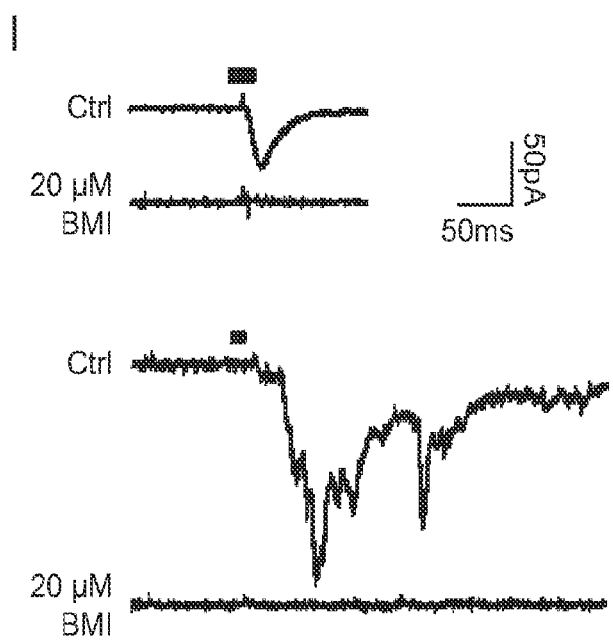
Figure 6:
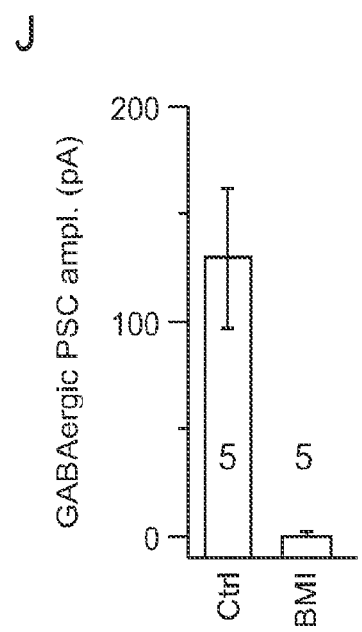

FIG. 6. GABAergic Synaptic Properties of hESC-derived Interneurons.
- (A) Images showing VGAT expression in hESC-derived NKX2.1-GFP+ neurons at 12 WPD. Right: zoom of dashed rectangle. Scale bar: left, 50 μm; right, 10 μm.
- (B) Traces showing spontaneous post-synaptic currents (PSCs) are hESC-derived neurons, bottom: PSCs were fully blocked by BMI. Scale bar: 100 pA, 5 s and 0.25 s (dashed line) for middle trace.
- (C) Percentage of neurons showing spontaneous PSCs at different stages.
- (D) hESC-derived neurons were transfected with ChR2-EYFP. Traces show pulses of blue light (blue bar) evoked PSCs in neighboring cells that were reversibly blocked by BMI, Scale bar: 50 pA and 50 ms. See also FIG. 13.
- (E) Average amplitudes of light-evoked GABAergic PSCs and application of BMI.
- (F-G) Traces showing light-evoked (blue bar) PSCs at different holding potentials. Summarized results (n=7) showing I-V curve of light-evoked GABAergic PSCs (G).
- (H) Merged image showing DIC of human fetal cortical cells co-cultured with sorted UbC-RFP+ and ChR2 transfected hESC-derived neurons. Scale bar: 20 μm.
- (I) Traces showing blue light (blue bar) stimulation of hESC-derived neuron-evoked PSCs in RFP-negative recorded human fetal cortical neurons. Upper panel shows PSC mono-synaptic response, lower panel shows PSC with poly-synaptic responses—both fully blocked by BMI. Scale bar: 50 pA and 50 ms.
- (J) Averaged amplitudes of light-evoked PSCs and application of BMI. E, J: Data represented as mean±SEM.

Figure 13:
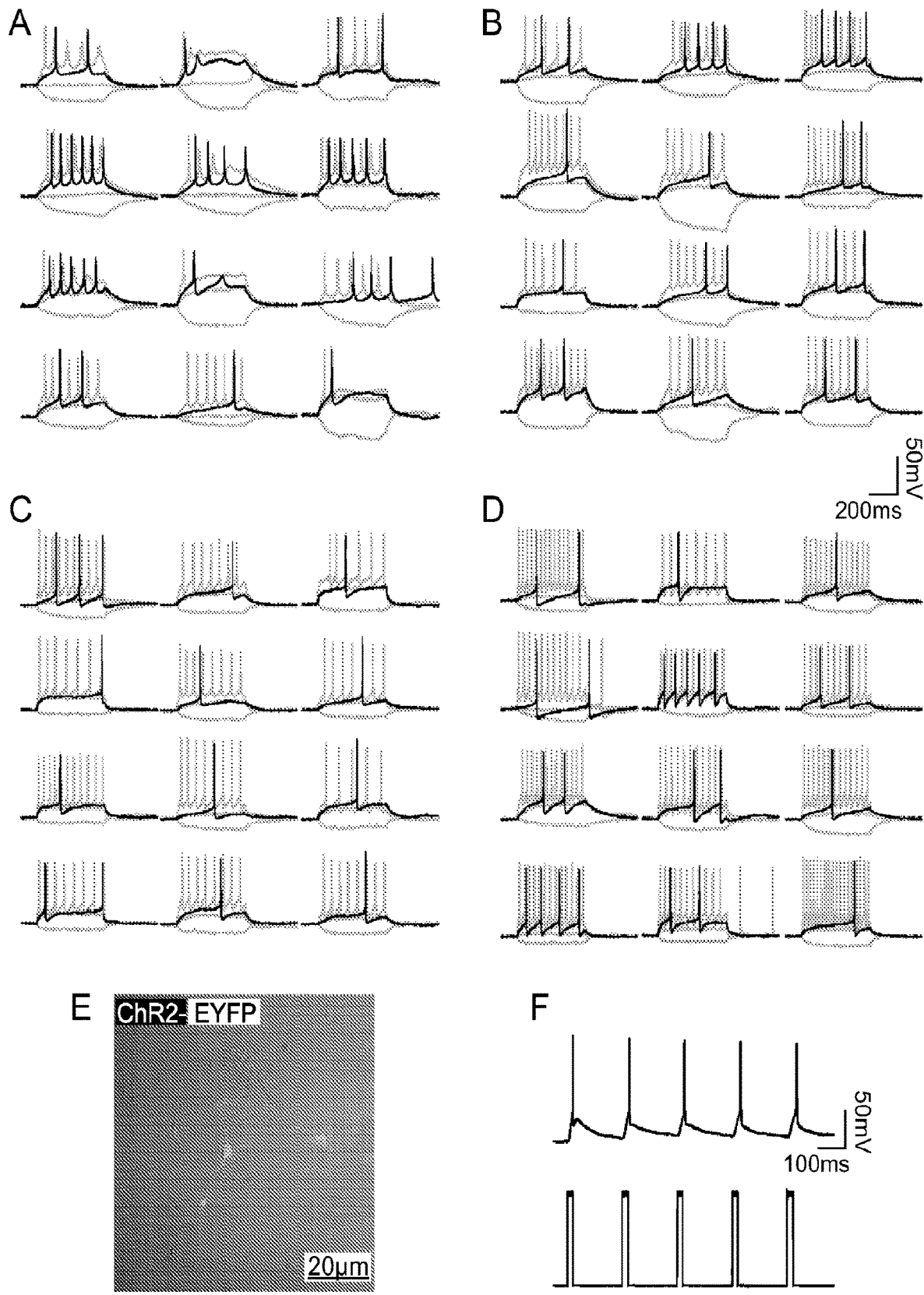
FIG. 13 (Panels A-F) show maturation of hESC-derived interneuron firing properties.

FIG. 13. Maturation of hESC-derived interneuron firing properties, related to FIGS. 5 and 6.
- (A-D) Example traces of action potentials (APs) at different stages post-differentiation. Stepped currents were injected into recorded neurons at $V_{hold}$ of –60 mV to –70 mV at different stages: (A) 8 WPD (B) 12 WPD (C) 15 WPD (D) 30 WPD. Red traces indicated APs upon threshold current injection. Black traces indicated APs upon two or three-fold times threshold current injection. Scale bars: 50 mV and 200 ms.
- (E-F) Blue light induced APs in ChR2-EYFP positive hESC-derived neurons. Merged image of EYFP fluorescence and DIC at 10 WPD (E). Scale bar: 20 μm. Pulses of blue light (blue trace) reliably induced APs (black trace) in ChR2-expressing neurons (F).

Example 7: hESC-Derived MGE-Like Interneuron Maturation and Functional Integration in the Mouse Brain To rigorously evaluate cell fate and function, hESC-derived MGE-like cells were transplanted into the mouse brain. We modified our protocol to avoid injection of undifferentiated NKX2.1+ neural stem cells (FIG. 16). Treatment with DAPT, a gamma secretase inhibitor of the Notch signaling pathway, was used to induce neuronal differentiation combined PSA-NCAM purification of neuronal precursors (Schmandt, T., et al. (2005). Stem Cells Dev 14, 55-64). An average of 75.7±5.2% (n=12) of NKX2.1-GFP+ cells were positive for high PSA-NCAM expression by FACS (FIG. 14A) NKX2.1-GFP+ and PSA-NCAM+ cells from day 35, enriched for GABAergic neuronal precursors (FIG. 3E), were injected into severe combined immuno-deficient (KID) newborn mouse cortex (FIG. 7A). The human-specific nuclear antigen (HNA) positive human cells survived for seven months post-injection (MPI) (the longest time point), and some human cells migrated more than 1 mm from the injection site (FIGS. 7B, 14B and 14C). Human cell survival rates (% of injected cells) after two, four, and seven MPI were 5.6±2.6%, 3.1±1.5%, and 8.6±3.1%, respectively. After two MPI, human cells expressing HNA and NKX2.1-GFP (67.8±1.6%), KI67 (25.5±1.7%), or DCX (79.8±3.8%) were mostly still located at the injection site (FIGS. 7B and 14B). But by four MPI, KI67 expression was significantly reduced (1.7±0.27%; p=0.04), and DCX expression was similarly reduced over time (5.9±4.9% by 7 MPI; p=0.008). Also, NKX2.1-GFP was detected in only 35.6±14% of human cells after seven MPI—a lower percentage than was found in 30 WPD co-cultures. A reverse trend was found for the post-mitotic neuronal marker, NEUN, which increased to 68.4±8.3% of human cells by seven MPI. In contrast, glial cell markers, GFAP and OLIG2, were expressed by a lower percentage of human cells at seven MPI (11.2±4.3% and 10.7±4.4%, respectively). Some hESC-derived cultures were labeled with UbC-RFP virus pre-injection. Following seven MPI in the mouse brain, RFP+ human cells with neuronal morphologies were found to express GABA, SST, CALB, and CALR (FIGS. 7C and 7E). PV+ human cells were not detected, except for rare cells with weak signal (4 of 1,829 cells). In summary, MGE-like GABAergic neuronal precursors injected into the mouse cortex primarily matured into neurons that expressed SST, CALR, and CALB interneuron subtype markers.

To examine whether hESC-derived MGE-like cells could develop into functional interneurons that synaptically integrate in vivo, we performed whole-cell recordings of RFP+ human cells in mouse brain slices seven MPI. Intracellular filling with neurobiotin and post-staining revealed the extensive process branching of recorded RFP+ neurons (FIG. 7F). Among 17 total human cells patched from three animals, 16 neurons exhibited the ability to fire action potentials with an average RMP of –64.8±4.0 mV. In addition, two groups of interneurons were identified, type I and type II, with different membrane properties and firing patterns. Type I interneurons had an average RMP of –67.3±2.9 mV, Rm of 257±78 MΩ, and Cm of 69.4±0.6 pF. The firing pattern of type I interneurons displayed a significant delay to spike at threshold, and little adaptation upon superthreshold, current injection (FIGS. 7G and 14D). Type II interneurons had more hyperpolarized RMP (–80.1±3.4 mV), smaller Rm (91±28 MΩ), and smaller Cm (27.75±4.6 pF). The firing pattern of type II interneurons showed rapid adaptation of initial spikes upon superthreshold current injection (FIGS. 7G and 14E). Furthermore, the transplanted hESC-derived interneurons received synaptic inputs (16 of 16) containing both BMI sensitive GABAergic and 6-Cyano-2,3-dihydroxy-7-nitroquinoxaline (CNQX) sensitive glutamatergic components (FIG. 7H), suggesting functional. integration into the host cortex.

Figure 7:
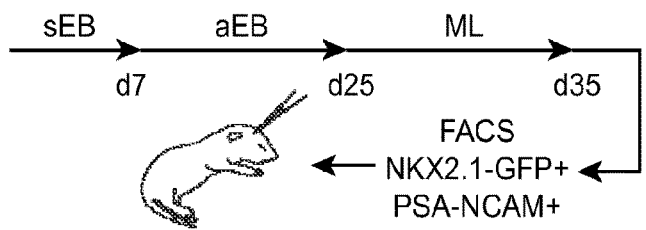
FIG. 7 (Panels A-H) show hESC-derived MGE-like interneuron precursor cell maturation and functional integration in the mouse brain.
Figure 7:
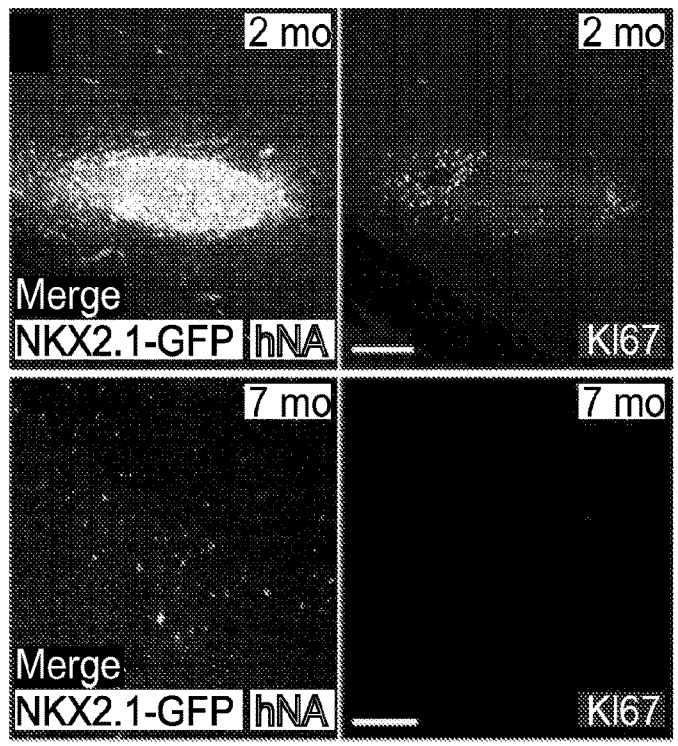
Figure 7:
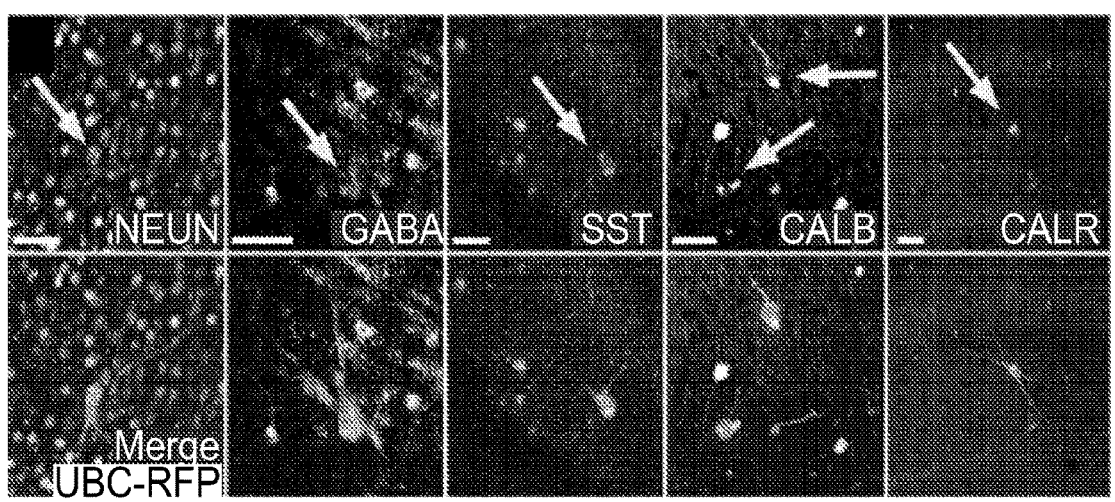
Figure 7:
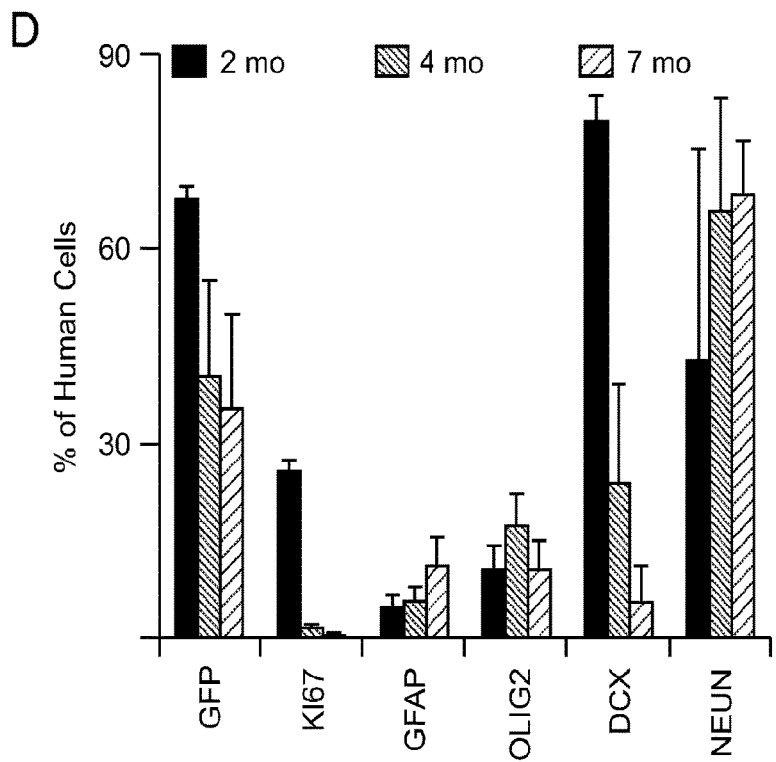
Figure 7:
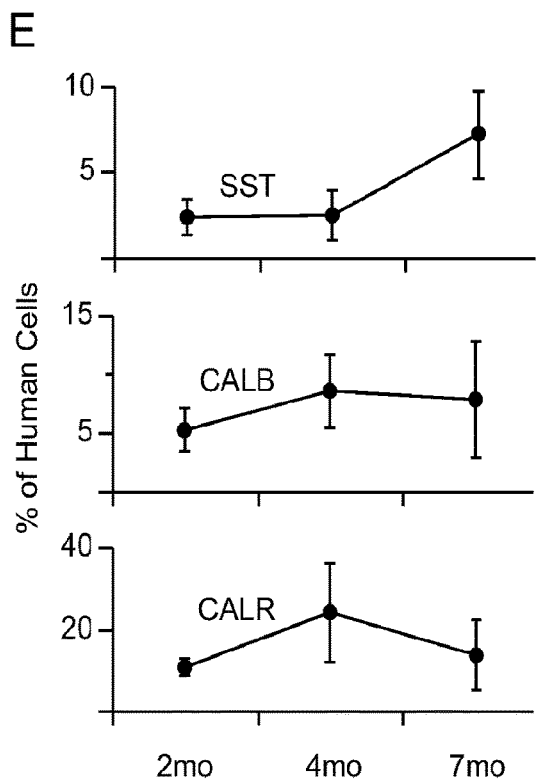
Figure 7:
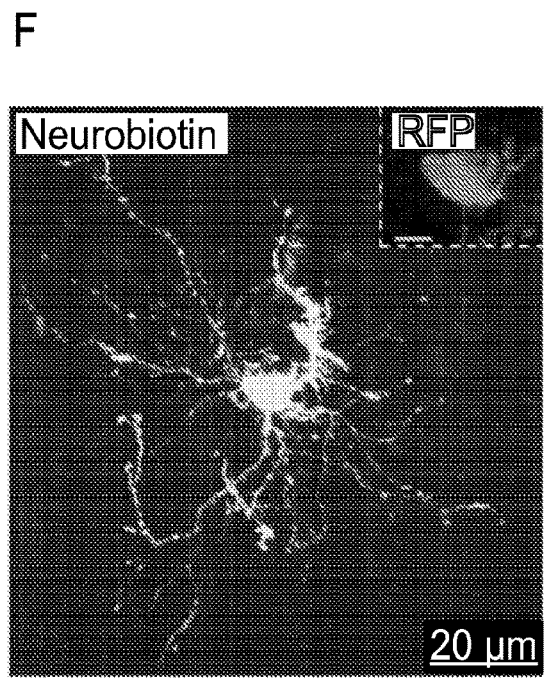
Figure 7:
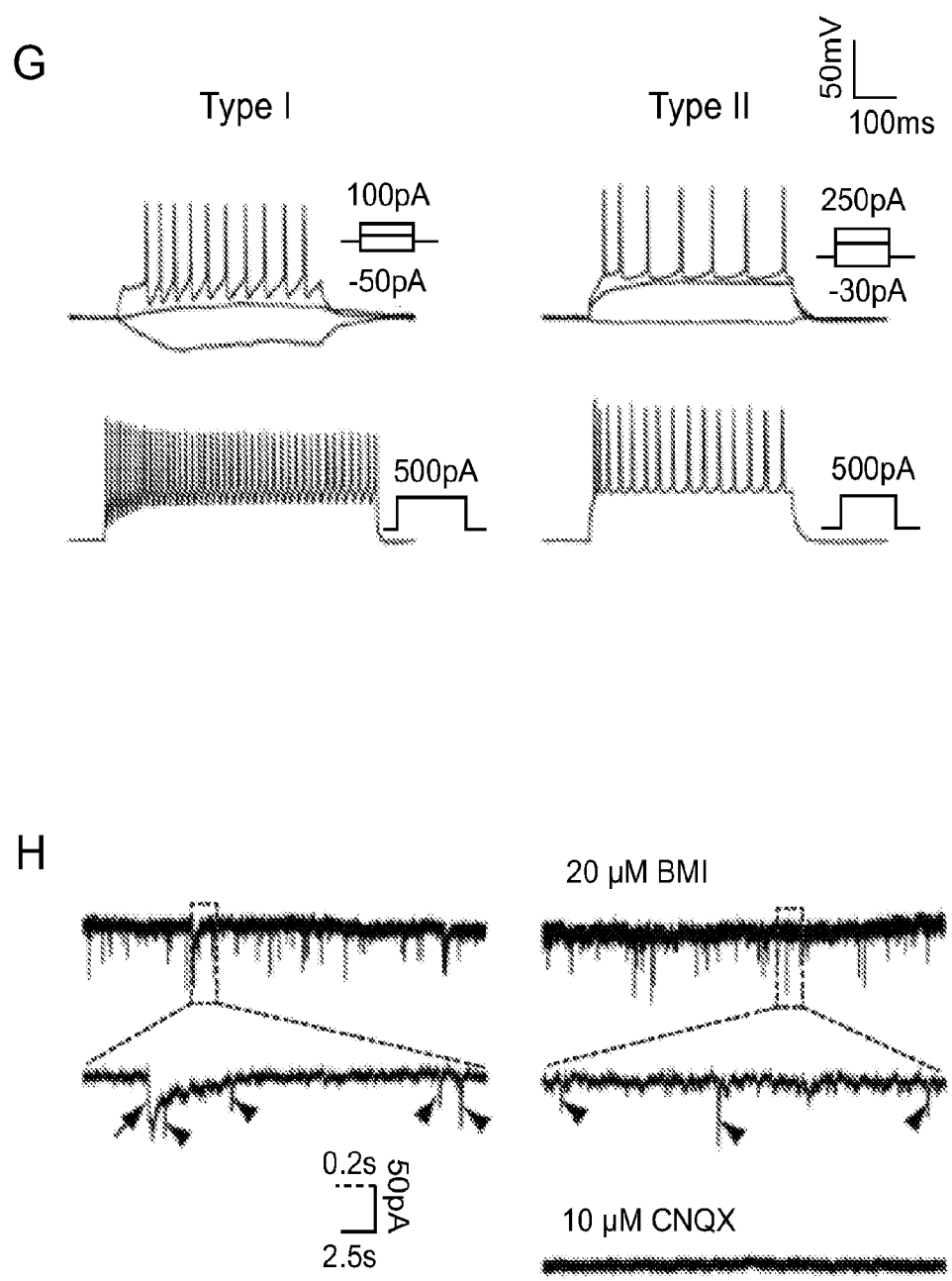

FIG. 7. hESC-derived MGE-like Interneuron Precursor Cell Maturation and Functional Integration in the Mouse Brain.
- (A) Day 35 ML cultures FACS-sorted for NKX2.1-GFP and PSA-NCAM, and injected into newborn mouse cortex. See also FIG. 16.
- (B) Mouse brain tissue sections at 2 and 7 MPI stained for human-specific hNA, GFP, and KI67. Blue: DAPI. Scale Bar: 200 µm. See also FIG. 14.
- (C) Histological analysis of human cells labeled with UbC-RFP that co-expressed (arrow) NEUN, GABA, SST, CALB, and CALR at 7 MPI. Blue: DAPI. Scale Bar: 50 µm.
- (D-E) Quantification of histology at 2 (black), 4 (orange), and 7 (blue) MPI, and of SST, CALB, and CALR (E). Data represented as mean±SEM.
- (F) hESC-derived neuron labeled by intracellular filling of neurobiotin (NB, green). Inset: RFP fluorescence of filled neuron 7 MPI. Scale bar: 20 µm; inset 5 µm.
- (G) Traces of AP firing patterns of type I (left) and type II (right) hESC-derived neurons upon near threshold (top) and superthreshold (bottom) current injection at 7 MPI. Scale bars: 50 mV and 100 ms.
- (H) Left panel: traces of spontaneous PSCs recorded from hESC-derived neurons post-injection: upper right: BMI blocked PSCs with slow decay-time (arrow), and the remaining PSCs with fast decay-time (arrow head) were blocked by subsequent application of CNQX (lower right panel). Scale bars: 50 pA, 2.5 s and 0.2 s (dashed line) for zoomed traces. See also FIG. 14.

Figure 14:
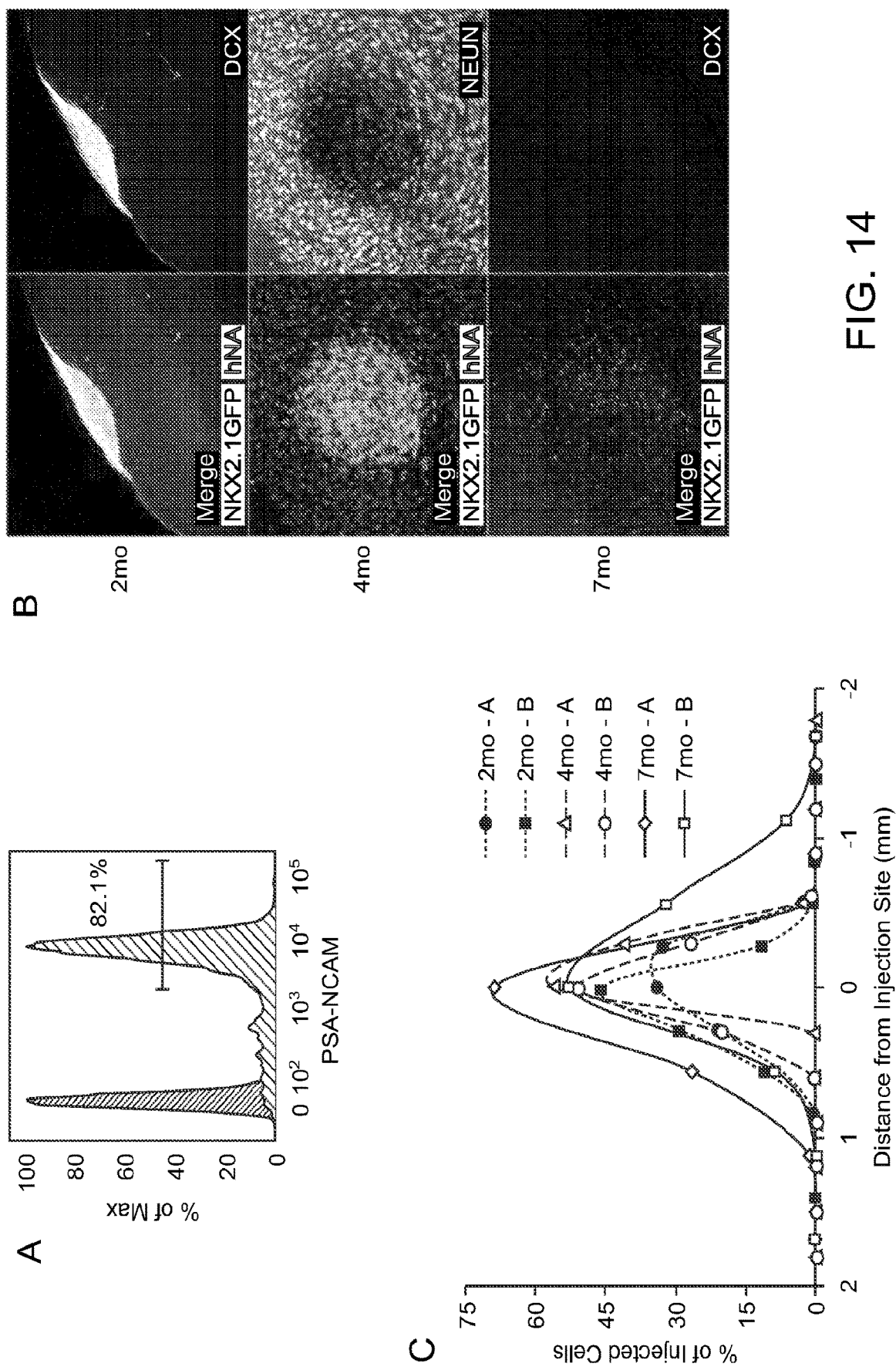
FIG. 14 (Panels A-G) depict maturation of hESC-derived MGE-like interneurons and subtype firing properties in the mouse brain.
Figure 14:
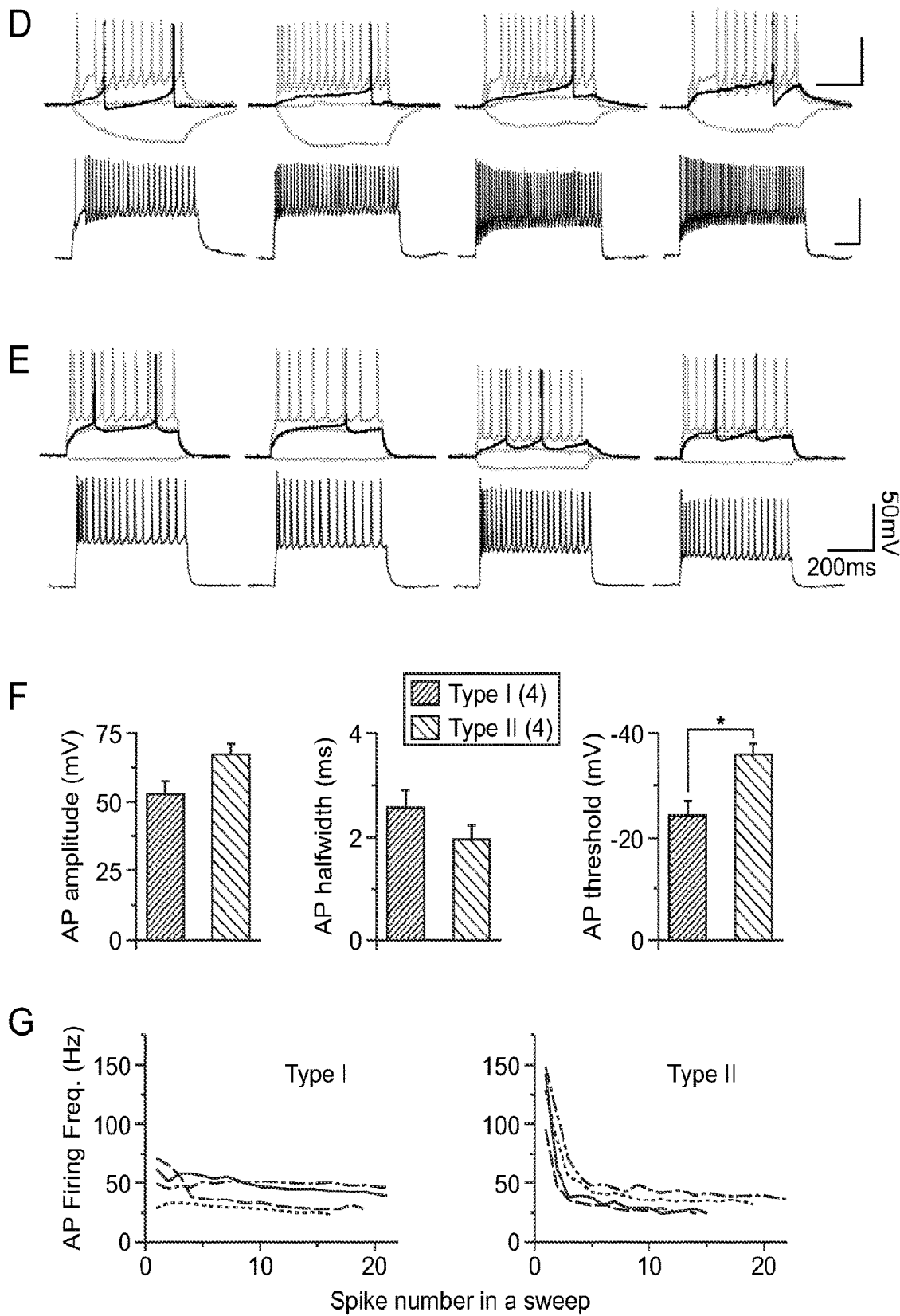

FIG. 14, Maturation of hESC-derived MGE-like interneurons and subtype firing properties in the mouse brain, related to FIG. 7 and FIG. 16.
- (A) FACS analysis histogram on d35 showing high expression of PSA-NCAM by most GIFT+ cells (red) compared to isotype antibody control (grey).
- (B) Immunostaining analysis of migration and maturation of NKX2.1-GFP+ and PSANCAM+ hESC-derived MGE-like cells 2, 4, and 7 months post-injection (MPI). By 7 MPI, human-specific nuclear antigen (HNA)+ human cells could migrate, downregulate GFP and DCX, and upregulate NEUN, a marker of neuronal maturation. Blue=DAPI.
- (C) hESC-derived MGE-like cell migration in 6 mice. Human cells were counted in rostral and caudal cortical sections flanking a single injection site at 2, 4, and 7 MPI. Some migration was detected by 7 MPI. Plotted as the percentage of injected cells.
- (D-G) Firing properties of type I and type ii hESC-derived interneurons at 7 MPI. AP firing patterns upon near threshold (top) and superthreshold (400-500 pA, bottom) current injection of type I (D) and type II (E) neurons. Each column (top trace and bottom trace) represents AP firing patterns of one neuron. Top panels: red trace represents threshold AP firing pattern; black trace is 2-fold threshold AP firing pattern. Scale bars: 50 mV and 200 ms. (F) Statistical results showing the differences in AP characteristics between type I and type II neurons. Data represented as mean±SEM, and students' t-test was used for statistical comparisons. * represents p<0.05. (G) Analysis of AP firing frequency upon superthreshold current injection. The type II neurons exhibited rapid adaptation firing properties.

FIG. 16. A summary of hESC differentiation protocol optimization, animal transplantation, and tumor incidence, related to FIGS. 7 and 14.

Example 8: hESC-Derived MGE-Precursor Like Cells

Figure 18:
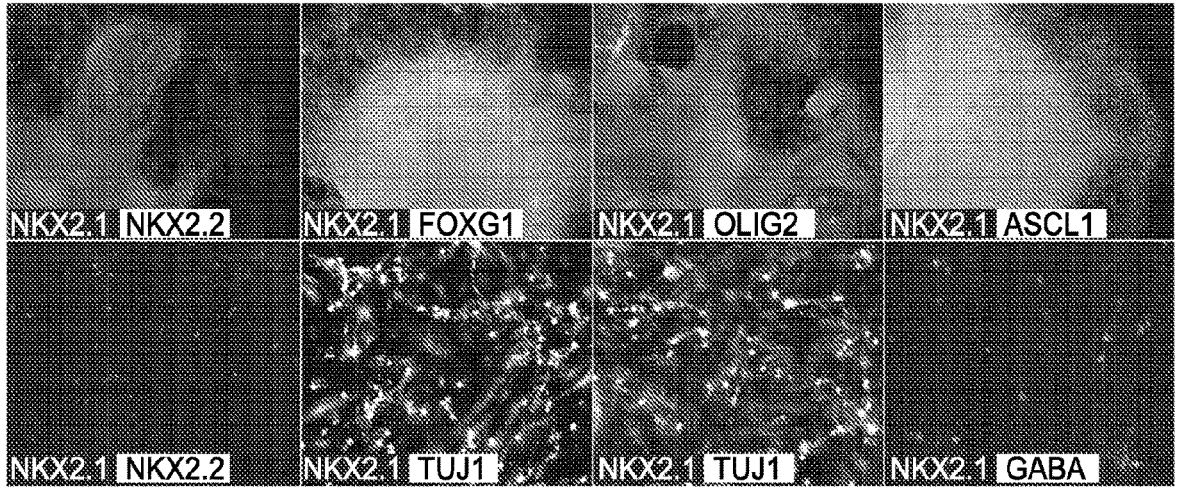
FIG. 18 depicts MGE precursor cells differentiated in vitro from hESC line ESI35.
Figure 19:
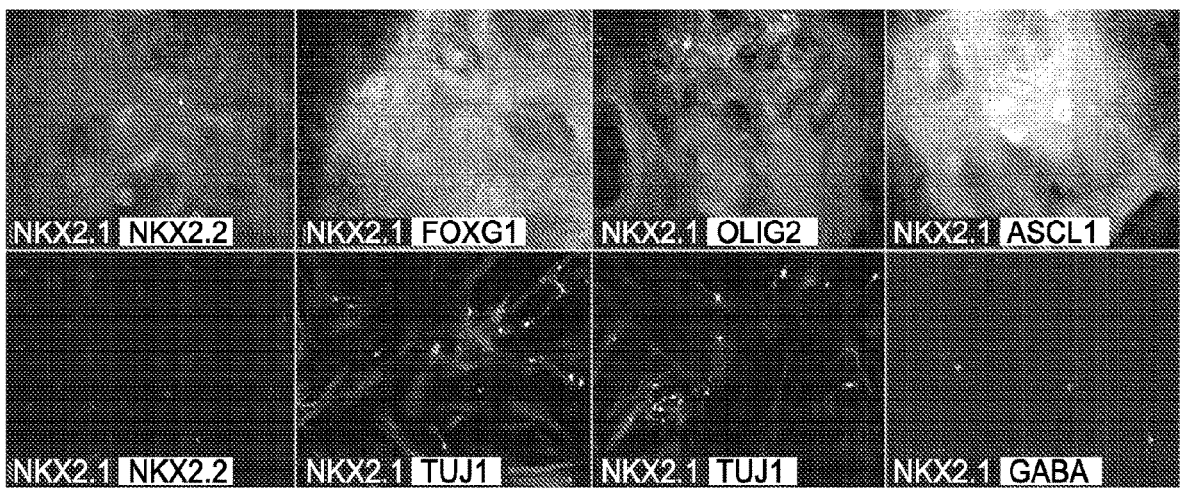
FIG. 19 depicts MGE precursor cells differentiated in vitro from hESC line ESI51.
Figure 20:
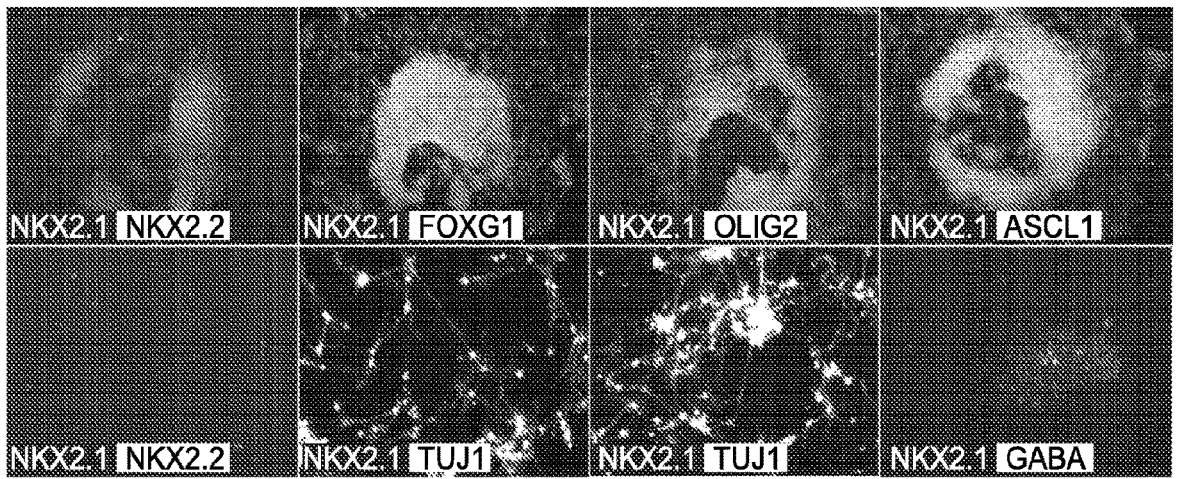
FIG. 20 depicts MGE precursor cells differentiated in vitro from hESC line H9.

Clinical grade GMP-matched hESC lines ESI17 (FIG. 17), ESI35 (FIG. 18), ESI51 (FIG. 19), and H9 (FIG. 20) were differentiated into MGE precursor like cells (top row) and further into interneurons (bottom row).

FIGS. 17-20, Top Row: hESC lines were differentiated with the B27+5F method as suspension embryoid bodies (sEB's) to day 7 followed by adherent EB (aEB) culture to day 28. Cultures were fixed for immunofluorescence staining, Most of the cells in the adherent EBs exhibited high expression of markers of MGE (NKX2.1), telencephalon (FOXG1), and neuronal specification (ASCL1). The minority of cells expressed markers of ventral hypothalamus (NKX2.2) and oligodendrocyte progenitor cells (OLIG2).

FIGS. 17-20, Bottom Row: Day 28 aEB cultures were dissociated to single cells, replaced as a monolayer, cultured for an additional 2 weeks in neurobasal media with B27 supplement with or without BDNF, DAPT, SHH and fixed for similar analysis. These day 42 monolayer cultures expressed NKX2.1, neuronal marker (TUJ), and began to express inhibitory neuron marker (GABA). OLIG2 expression was not detected, and NKX2.2 was only found in rare cells.

Figure 21:
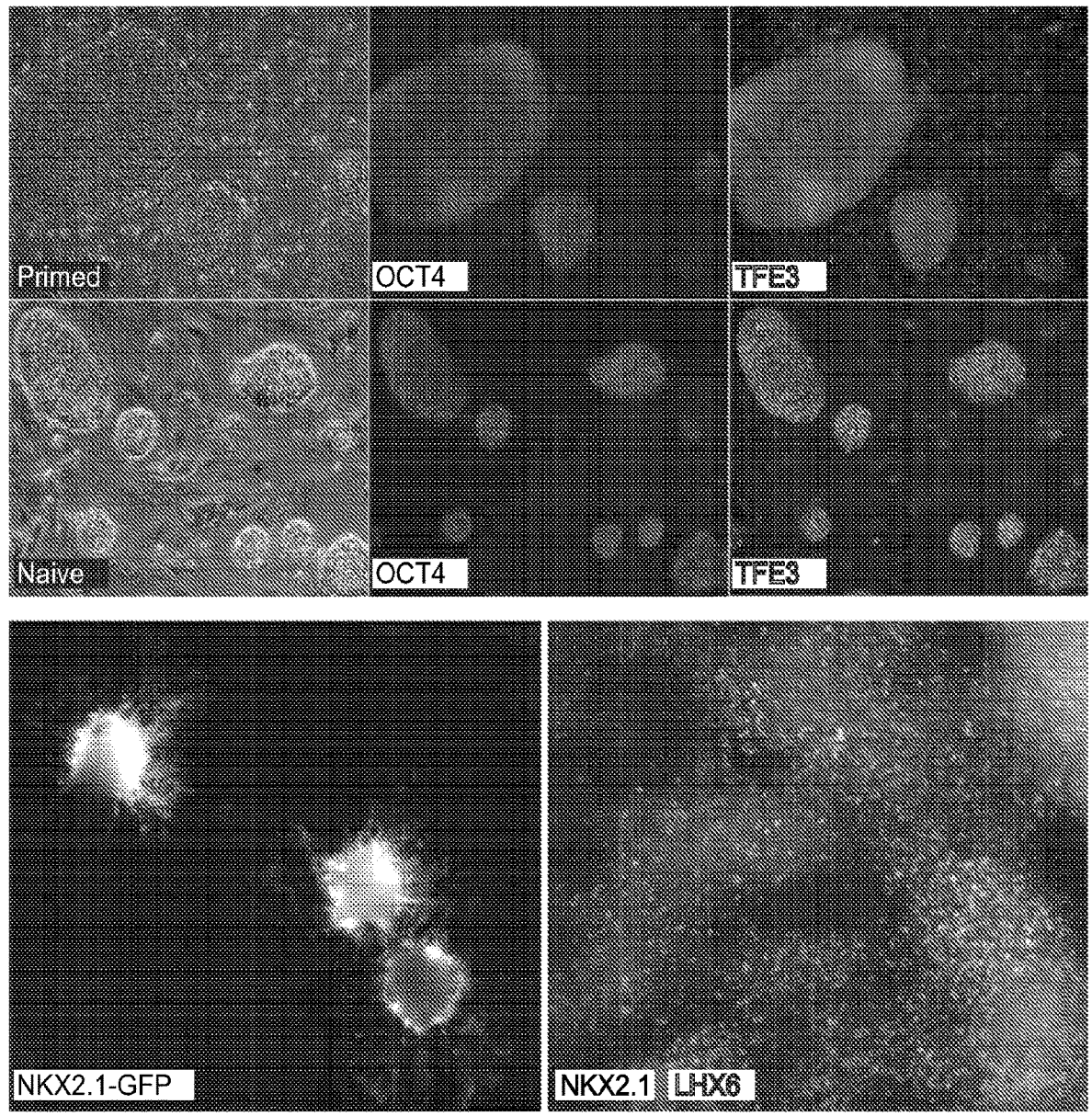
FIG. 21 illustrates generation of MGE precursor cells by differentiation of naïve human pluripotent stem cells.

Example 9: Derivation of MGE Precursor Cells from Naïve Human Pluripotent Stem Cells Typical primed HES3 (NKX2.1-GFP) hESCs express homogeneous OCT4 but do not express naïve stem cell marker TFE3 homogeneously in the nucleus (FIG. 21, top row). Primed HES3 (NKX2.1.-GFP) hESCs were converted into naïve HES3 stem cells using published methods (Gafni and Hanna et al, Nature 2013). Naïve hESCs expressed TFE3 in the nucleus of virtually every cell (FIG. 21, middle row). Differentiation of naïve stem cells using the B27+5F method resulted in differentiation of the HES3 hESCs into cells that expressed MGE markers NKX2.1-GFP, NKX2.1, and LHX6 by 2 to 6 weeks of adherent EB culture (FIG. 21, bottom row).

Naïve ES cells are more undifferentiated than traditional human ES/iPS cells grown in typical media with bFGF only. Traditional hPSCs are more equivalent to the later-stage post-implantation embryo epiblast than mouse mPSCs, which are more similar to the earlier-stage pre-implantation inner cell mass. Naïve human ES and iPS cells are therefore more similar to mouse ES cells. Their properties (gene expression and epigenetics) are equivalent to the pre-implantation embryo. They can be identified by the expression and nuclear localization of the transcription factor TFE3, and by colony morphology. These properties distinguish naïve cells from traditional primed hPSCs.

Figure 22:
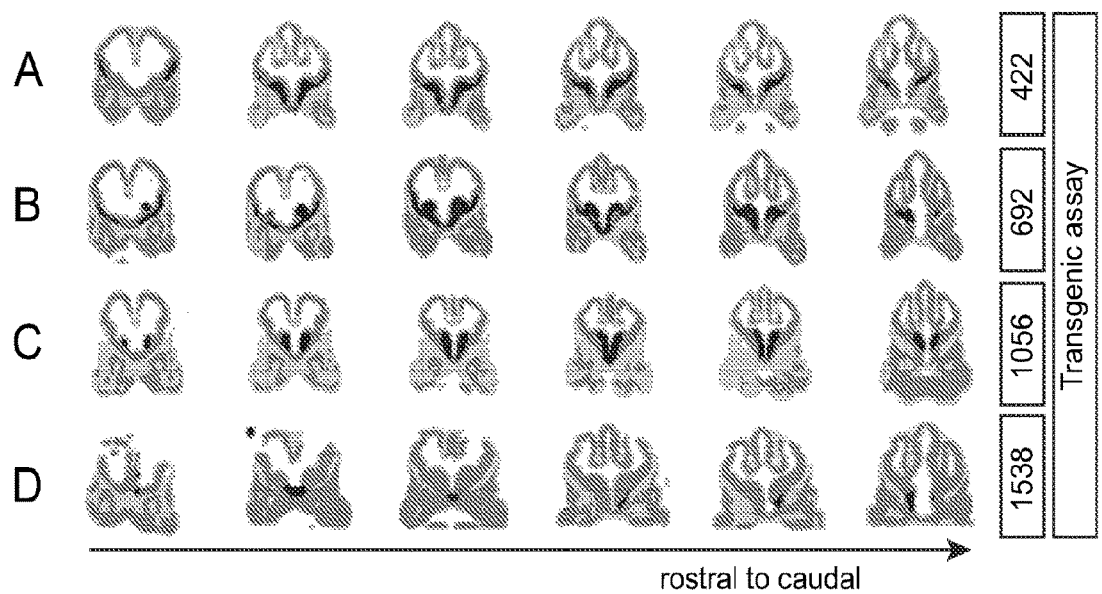
FIG. 22 (Panels A-N) illustrates utilization of an MGE-enriched enhancer sequence for the selection and purification of interneurons derived from MGE precursor cells generated by differentiation of hPSC.
Figure 22:
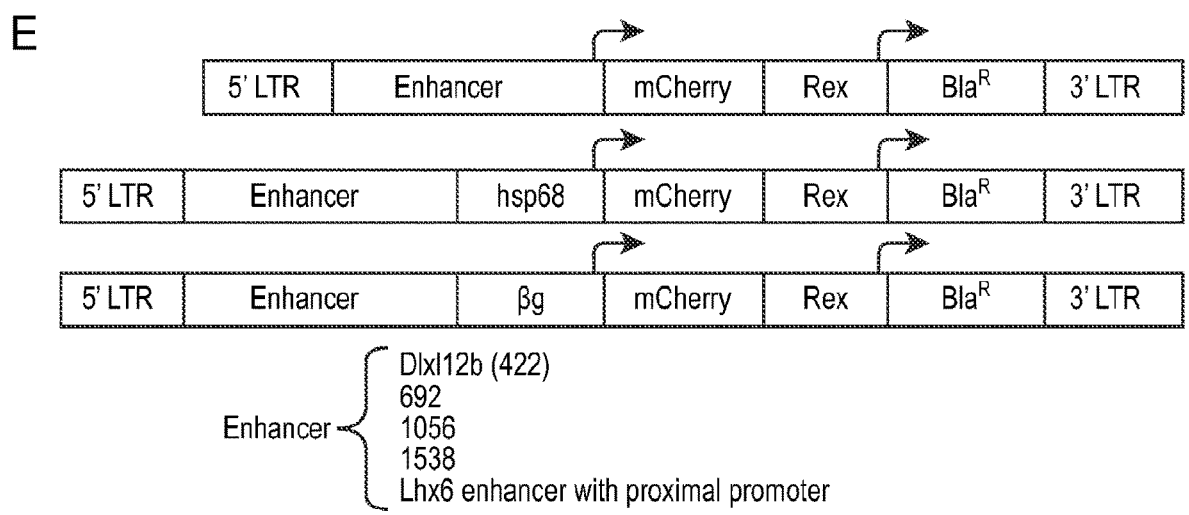
Figure 22:
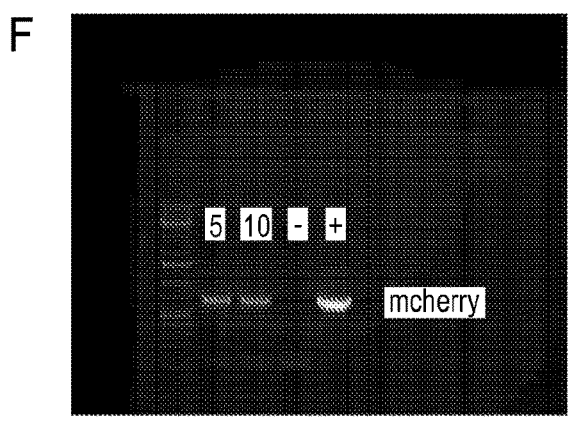
Figure 22:
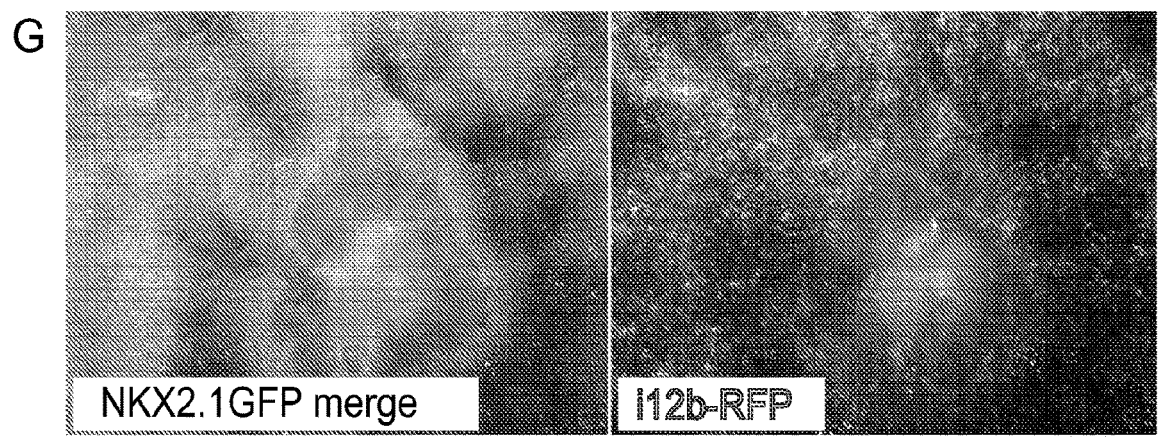
Figure 22:
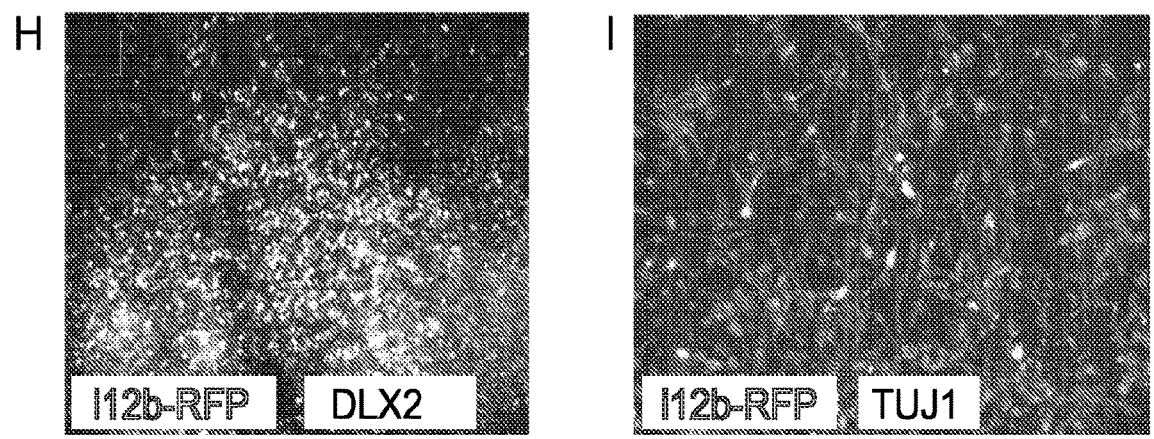
Figure 22:
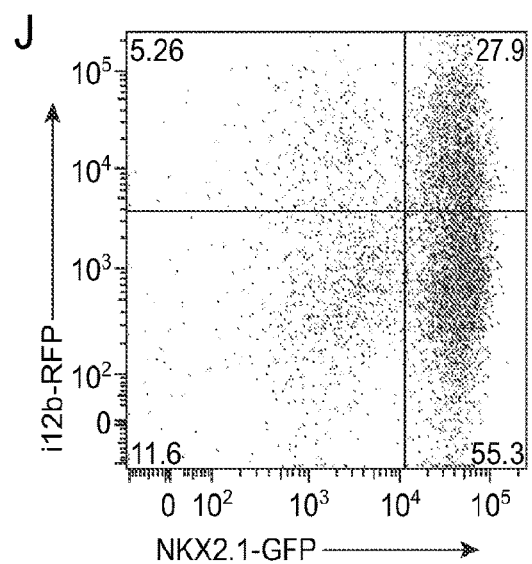
Figure 22:
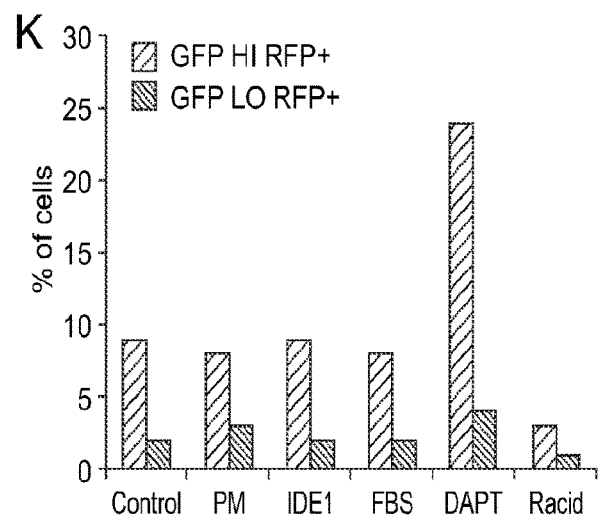
Figure 22:
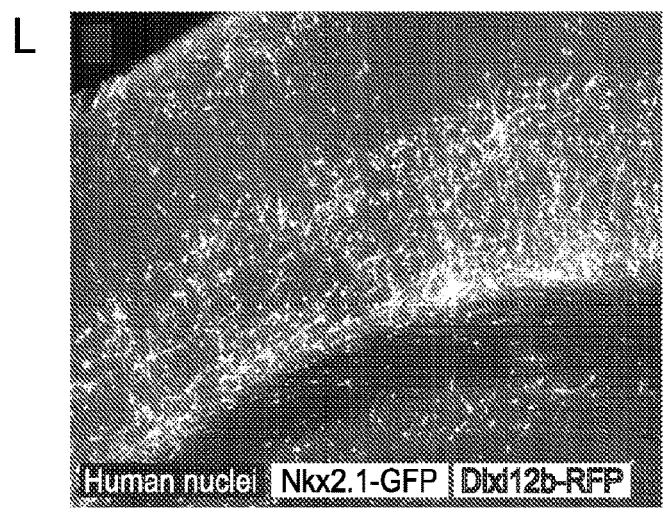
Figure 22:
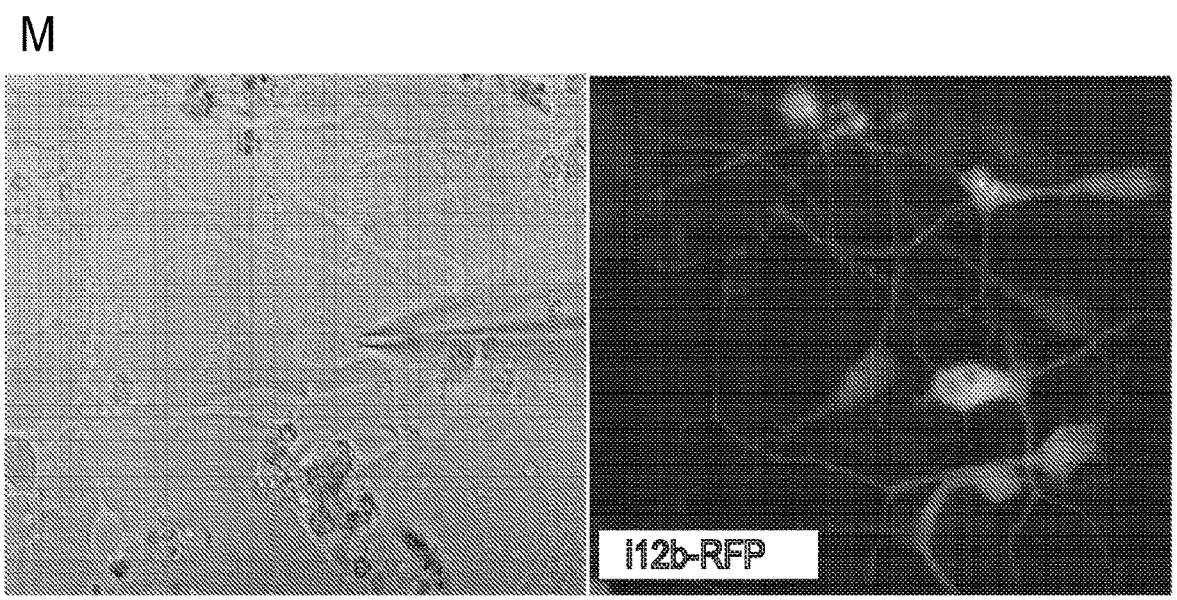
Figure 22:
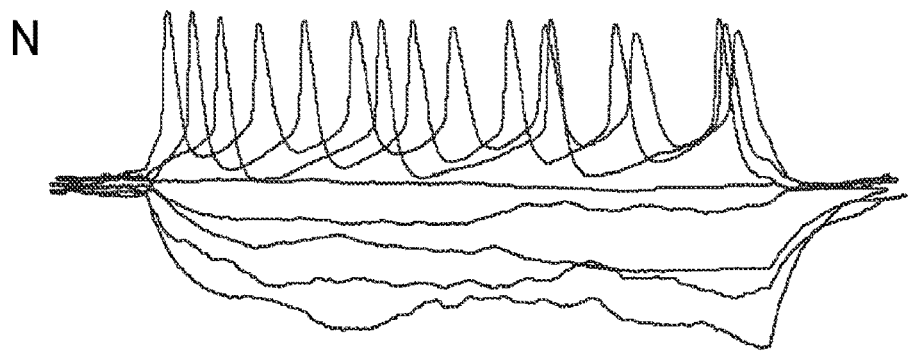

Example 10: Utilization of an MGE-Enriched Enhancer Sequence for the Selection and Purification of Interneurons Derived from MGE Precursor Cells Differentiated In Vitro from hPSC Transgenic mice that contain various enhancer-reporter transgenes are available. In these mice, the reporter gene is expressed with different patterns and lineage specificities in the forebrain depending on the DNA sequence of the enhancer (FIGS. 22 A-D).

Based on their expression pattern in the forebrain of the transgenic mice, MGE-enriched enhancer sequences were cloned into viral vectors to drive the expression of fluorescent reporter genes and/or antibiotic resistance genes in an MGE-selective manner. The constructs also contained a Rex1-antibiotic resistance cassette to enable the selection and expansion of stable transgenic hPSCs. (FIG. 22, E).

The intergenic DLX½i12b (422) enhancer driving the mCherry RFP reporter gene (i12b-RFP) was delivered into the HES3 NKX2.1-GFP hESC line using lentivirus, and two stable cell lines were generated (#5 and #10) as confirmed by genomic DNA PCR for mCherry. (FIG. 22, F).

The modified lines were differentiated using the B27±5F method, and i12b-RFP expression was detected after three weeks of differentiation, along with NKX2.1. (FIG. 22, G). i12b-RFP+ cells in EBs co-expressed GABAergic neuron marker DLX2 and neuronal marker TUJ1. (FIGS. 22, H and I).

Flow cytometry analysis confirmed that many cells derived with the B27+5F method co-expressed both NKX2.1-GFP and i12b-RFP (FIG. 22, J). Treatment of these cultures with NOTCH pathway inhibitor, DAPT, resulted in a marked increase in this double positive population of MGE derived interneurons (FIG. 22, K).

Double positive (NKX2.1-GFP+ and i12b-RFP+) MGE precursor cells were purified by FACS and transplanted into the SCID mouse cortex. Several months post-injection, human cells expressing both NKX2.1-GFP and i12b-RFP were found to disperse from the injection. site and to integrate into the surrounding rodent grey matter, consistent with hallmark properties of differentiation into MGE derived interneurons. (FIG. 22, L).

Cultured hPSC-derived MGE derived interneurons expressing i12b-RFP (FIG. 22, M) were also analyzed using electrophysiology. Recorded RFP+ interneurons fired repetitive trains of action potentials, confirming their neuronal fate (FIG. 22, N).

Figure 23:
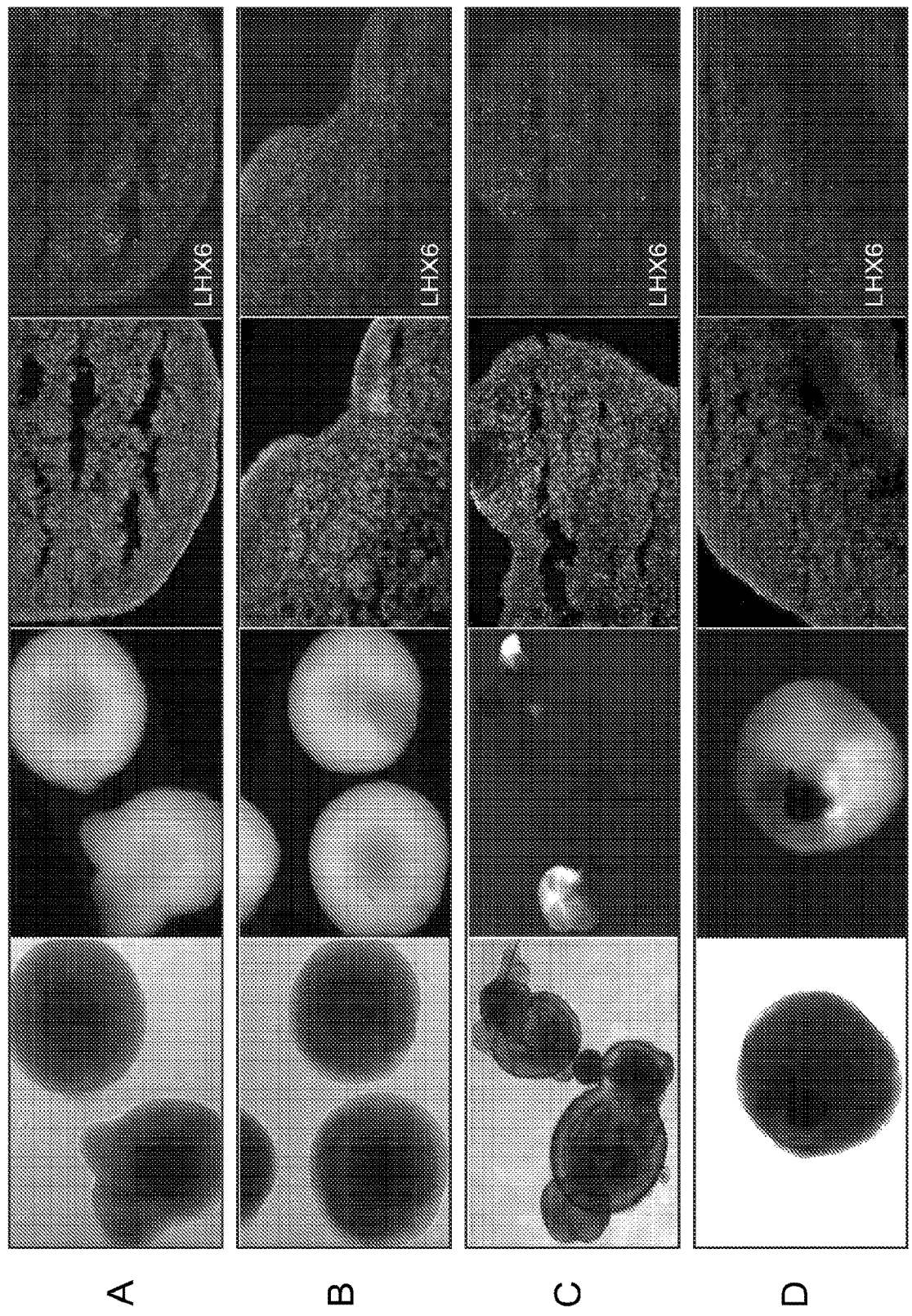
FIG. 23 (Rows A-D) depict generation of MGE derived interneurons using long-term suspension culture.

Example 11: Generation of MGE Derived Interneurons Using Long-Term Suspension Culture HES3 hESCs differentiated using B27+5F conditions as sEB's in normoxic gas (20% oxygen tension) produced MGE interneurons expressing NKX2.1-GFP and LHX6. The cells were analyzed on day 35 of culture (FIG. 23, row A)

HES3 hESCs differentiated using B27+5F conditions as sEBs in normoxic gas produced MGE interneurons expressing NKX2.1-GFP and LEX6. In this differentiation protocol, SHH agonist (purmorphamine) was removed on day 21 (in contrast to FIG. 23, row A, above, where SHH agonist (purmorphamine) was present throughout the culture period). The cells were analyzed on day 35 of culture (FIG. 23, row B).

HES3 hESCs were cultured in GMEM and DMEM/F12 media with KSR, N2, and B27 supplements (added sequentially) and ROCK, WNT, and SMAD inhibitors and SHH agonist in hyperoxic gas (40% oxygen tension). The cells were analyzed on day 35 of culture, (FIG. 23, row C).

HES3 hESCs were cultured in GMEM and DMEM/F12 media with KSR, N2, and B27 supplements (added sequentially) and ROCK, WNT, and SMAD inhibitors and SHH agonist with matrigel added to the media (1-2%). sEBs were maintained for more than 50 days in culture in hyperoxic gas. The cells were analyzed on day 60 of culture. (FIG. 23, row D).

Example 12: Generation of MGE Precursor Cells Using Small Molecule Inhibitors of BMP and WNT Signaling Pathways The following are further examples of small molecule inhibitors of BMP and WNT signaling pathways that are useful for generation of MGE precursor cells. The differentiation protocol was as described in Example 1.

Figure 24:
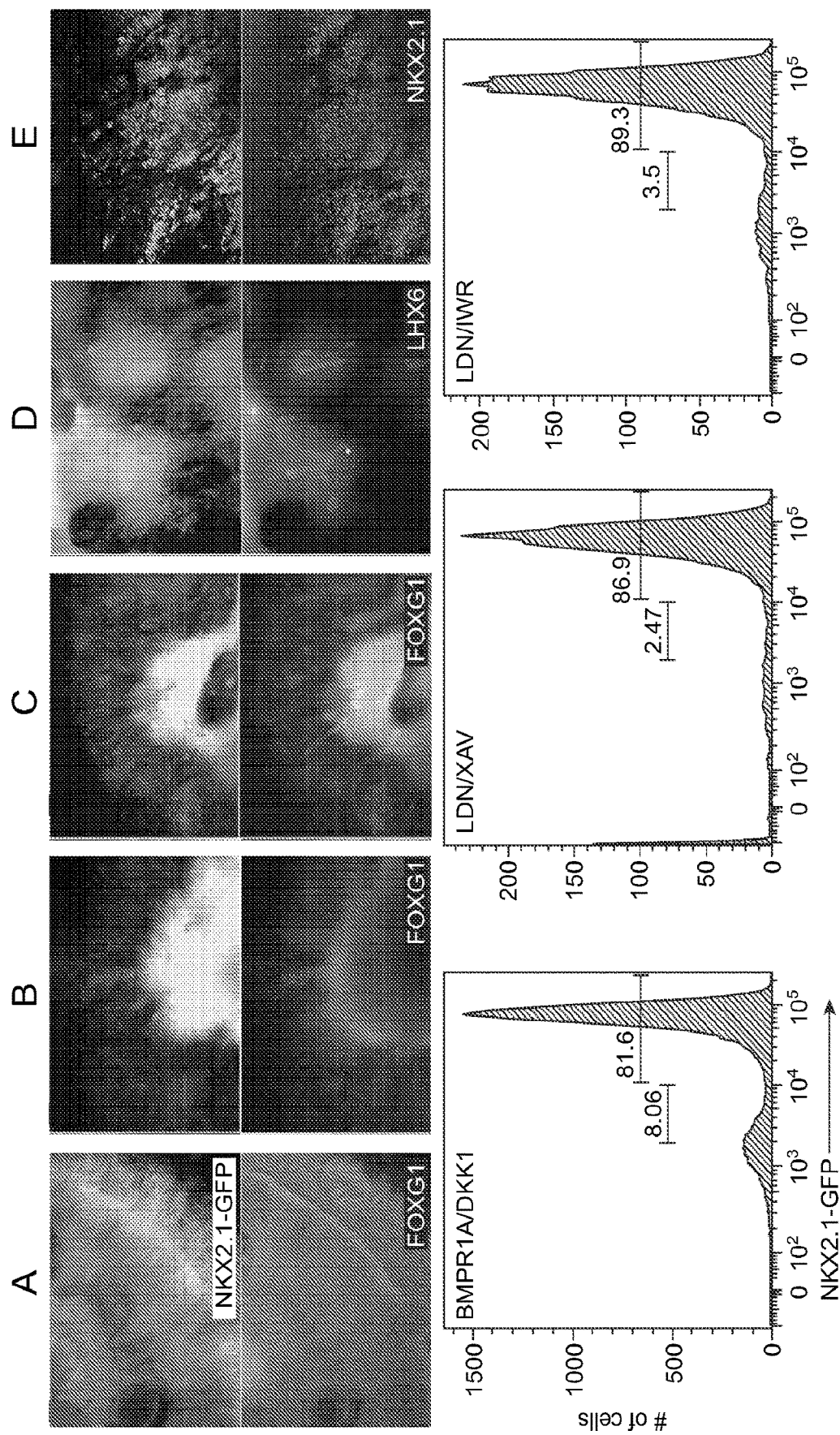
FIG. 24 (Panels A-E) illustrates that numerous small molecule inhibitors of BMP and WNT signaling pathways are effective in inducing differentiation of hESCs into MGE precursor cells.

FIG. 24, A: B27+5F differentiation protocol with BMPR1A and DKK1 as inhibitors of BMP and WNT signaling pathways, respectively, induced differentiation of hESCs into MGE precursor cells that co-express NKX2.1GFP (top) and FOXG1 (bottom). (see also, Example 1 for details).

FIG. 24, B: B27+5F differentiation protocol with LDN193189 (0.1 µM, Catalog #04-0019 (Stemgent)) and XAV939 (2 µM, Catalog #3748 (Tocris)) as inhibitors of BMP and WNT signaling pathways, respectively, induced differentiation of hESCs into MGE precursor cells that co-express NKX2.1GFP (top) and FOXG1 (bottom).

FIG. 24, C: B27+5F differentiation protocol with LDN193189 (0.1 µM, Catalog #04-0019 (Stemgent)) and IWIR1e (3 µM, Cayman Chemical Catalog #13659) as inhibitors of BMP and WNT signaling pathways, respectively, induced differentiation of hESCs into MGE precursor cells that co-express NKX2.1GFP (top) and FOXG1 (bottom).

FIG. 24, D: B27+5F differentiation protocol with LDN193189 (0.1 µM, Catalog #04-0019 (Stemgent)) and IWP2 (5 µM, Stemgent Catalog #04-0034) as inhibitors of BMP and WNT signaling pathways, respectively, induced differentiation of hESCs into MGE precursor cells that co-express NKX2.1GFP (top) and LHX6 (bottom).

FIG. 24, E: B27+5F differentiation protocol with Dorsamorphin (1 µM, Sigma Catalog #P5499) and (CKI)-7 (1 µM, Sigma Catalog #D0742) as inhibitors of BMP and WNT signaling pathways, respectively, induced differentiation of hESCs into MGE precursor cells that co-express NKX2.1GFP and NKX2.1.

The timing of addition of the inhibitors of BMP and WNT signaling pathways was as depicted in FIG. 1A.

FIG. 24, Bottom Panel: Flow cytometry was used to determine the efficiency of generation of NKX2.1GFP+ MGE precursor cells using the small molecule inhibitors. The efficiency of generation of NKX2.1GFP+ MGE precursor cells was determined as what percent of cells of the cells analyzed were NKX2.1GFP+ MGE precursor cells.

For the B27+5F differentiation protocol with BMPR1A and DKK1 as inhibitors of BMP and WNT signaling pathways, respectively, efficiency of generation of was 81.6%. When LDN193189 and XAV939 were substituted for BMPR1A and DKK1, the efficiency of generation of NKX2.1GFP+ MGE was 86.9%. Substitution of BMPR1A and DKK1 with LDN193189 and IWR resulted in generation of NKX2.1GFP+ MGE at an efficiency of 89.3%. (FIG. 24, bottom panel). 30,000 to 100,000 cells were analyzed.

What is claimed is:

1. A method comprising:
   a) providing primate pluripotent stem (pPS) cells in a culture medium;
   b) introducing to the culture medium, factors comprising:
      i) an activator of the sonic hedgehog (shh) pathway,
      ii) a SMAD inhibitor, and
      iii) a wnt pathway inhibitor,
   to produce a cell culture enriched in MGE precursor cells;
   c) culturing the MGE precursor cells to produce PSA-NCAM-negative or DLX2-negative cells; and
   d) enriching for the PSA-NCAM-negative or DLX2-negative cells.

2. The method of claim 1, wherein step c) comprises culturing the MGE precursor cells in absence of a Notch pathway inhibitor.

3. The method of claim 1, wherein the MGE precursor cells express Nkx2.1.

4. The method of claim 1, wherein the MGE precursor cells express OLIG2.

5. The method of claim 1, wherein the human pluripotent stem cells comprise human induced pluripotent stem cells.

6. The method of claim 1, wherein the human pluripotent stem cells comprise human embryonic stem cells.

7. The method of claim 1, wherein the MGE precursor cells are genetically modified.

8. The method of claim 7, wherein the MGE precursor cells express a fluorescent protein.

9. The method of claim 1, wherein the primate pluripotent stem cells are cultured in the absence of a feeder layer.

10. The method of claim 1, wherein the primate pluripotent stem cells are cultured in suspension.

11. The method of claim 1, wherein the culture medium comprises two or more inhibitors of SMAD.

12. The method of claim 1, wherein the culture medium further comprises an apoptosis inhibitor.

13. The method of claim 1, wherein the inhibitor of apoptosis is an inhibitor of Rho-associated kinase (ROCK).

14. The method of claim 1, wherein a neural supplement is added to the culture medium.

15. The method of claim 1, wherein a neurotrophic factor is added to the culture medium.

16. The method of claim 1, wherein a growth factor is added to the culture medium.

17. The method of claim 1, wherein enriching for the PSA-NCAM negative cells comprises isolating PSA-NCAM-negative cells.

18. The method of claim 1, comprising enriching for the PSA-NCAM-negative cells by removing PSA-NCAM-positive cells.

19. The method of claim 1, comprising enriching for DLX2-negative cells by isolating DLX2-negative cells.

20. The method of claim 1, comprising enriching for the DLX2-negative cells by removing DLX2-positive cells.

21. The method of claim 1, comprising enriching for the DLX2-negative cells.

22. The method of claim 1, wherein the PSA-NCAM-negative cells are progenitor cells.

23. The method of claim 1, further comprising transplanting the PSA-NCAM-negative cells into nervous system of a mammal.

24. The method of claim 1, wherein step c) comprises culturing the MGE precursor cells to produce PSA-NCAM-negative cells.

25. The method of claim 24, comprising enriching for the PSA-NCAM-negative cells by removing PSA-NCAM-positive cells.

26. The method of claim 24, wherein the culture medium comprises two or more inhibitors of SMAD.

27. The method of claim 26, wherein the enriching comprises isolating PSA-NCAM-negative cells.

* * * * *